(12) United States Patent
Crabtree et al.

(10) Patent No.: US 12,373,600 B1
(45) Date of Patent: Jul. 29, 2025

(54) DISCRETE COMPATIBILITY FILTERING USING GENOMIC DATA

(71) Applicant: QOMPLX LLC, Reston, VA (US)

(72) Inventors: Jason Crabtree, Vienna, VA (US); Richard Kelley, Woodbridge, VA (US); Jason Hopper, Halifax (CA); David Park, Fairfax, VA (US)

(73) Assignee: QOMPLX LLC, Reston, VA (US)

( * ) Notice: Subject to any disclaimer, the term of this patent is extended or adjusted under 35 U.S.C. 154(b) by 0 days.

(21) Appl. No.: 18/662,988

(22) Filed: May 13, 2024

(51) Int. Cl.
| | |
|---|---|
| *H04L 9/00* | (2022.01) |
| *G06F 21/62* | (2013.01) |
| *G16H 10/60* | (2018.01) |
| *H04L 9/06* | (2006.01) |

(52) U.S. Cl.
CPC .......... *G06F 21/6245* (2013.01); *G06F 21/62* (2013.01); *G16H 10/60* (2018.01); *H04L 9/008* (2013.01); *H04L 9/0618* (2013.01)

(58) Field of Classification Search
CPC ..... G06F 21/6245; G16H 10/60; H04L 9/008; H04L 9/0618
USPC ........................................................ 713/193
See application file for complete search history.

(56) References Cited

U.S. PATENT DOCUMENTS

| | | | |
|---|---|---|---|
| 7,251,610 B2 | 7/2007 | Alban et al. | |
| 7,275,220 B2 | 9/2007 | Brummel et al. | |
| 7,337,123 B2 | 2/2008 | Dvorak et al. | |
| 7,979,294 B2 | 7/2011 | Larsen et al. | |
| 7,992,780 B2 | 8/2011 | Larsen | |
| 8,050,944 B2 | 11/2011 | Brummel et al. | |
| 8,140,370 B2 | 3/2012 | Larsen et al. | |
| 8,165,900 B2 | 4/2012 | Larsen | |
| 8,249,895 B2 | 8/2012 | Faulkner et al. | |
| 8,364,501 B2 | 1/2013 | Rana et al. | |
| 8,428,968 B2 | 4/2013 | Bellam et al. | |
| 8,521,565 B2 | 8/2013 | Faulkner et al. | |
| 8,615,403 B2 | 12/2013 | Lipsky et al. | |
| D703,690 S | 4/2014 | MacCubbin et al. | |
| 8,688,474 B2 | 4/2014 | Walter et al. | |
| 8,725,547 B2 | 5/2014 | Fuhrmann et al. | |

(Continued)

OTHER PUBLICATIONS

Amitay, Yael, et al., CellSighter: a neural network to classify cells in highly multiplexed images. Nat Commun 14, 4302 (2023) United States.

(Continued)

*Primary Examiner* — Catherine Thiaw
*Assistant Examiner* — Nega Woldemariam
(74) *Attorney, Agent, or Firm* — Galvin Patent Law LLC; Brian R Galvin

(57) ABSTRACT

A system is disclosed for discreetly assessing the compatibility of two or more human genomes across diverse elements, activities, and engagement platforms relevant to potential mating scenarios. The genomic data is subjected to encryption, with the option of employing homomorphic encryption to safeguard user privacy and security. Processing of the data is facilitated through a personal health database processing system, which may be cloud-based or edge-based. The application of homomorphic encryption ensures that the genomic information of individual users remains encrypted during processing, with the outcome limited to the display of progeny compatibility to the respective end users.

24 Claims, 35 Drawing Sheets

(56) References Cited

U.S. PATENT DOCUMENTS

| | | |
|---|---|---|
| 8,731,969 B1 | 5/2014 | Bellam et al. |
| 8,732,795 B2 | 5/2014 | Skeel et al. |
| 8,768,720 B2 | 7/2014 | Larsen |
| 8,812,599 B2 | 8/2014 | Fuhrmann |
| 8,825,502 B2 | 9/2014 | Bormann et al. |
| 8,843,505 B2 | 9/2014 | Campbell et al. |
| 8,909,660 B2 | 12/2014 | Campbell et al. |
| 8,972,272 B1 | 3/2015 | Dvorak et al. |
| 9,147,039 B2 | 9/2015 | Rana et al. |
| 9,208,285 B1 | 12/2015 | Campbell et al. |
| 9,750,408 B1 | 9/2017 | Martin et al. |
| 9,836,579 B1 | 12/2017 | Rana et al. |
| 10,096,075 B2 | 10/2018 | Dvorak et al. |
| 10,242,158 B2 | 3/2019 | Lipsky et al. |
| 10,282,799 B2 | 5/2019 | Buttner et al. |
| 10,431,339 B1 | 10/2019 | Cornelius et al. |
| 10,446,267 B2 | 10/2019 | Fuhrmann |
| 10,674,910 B1 | 6/2020 | Martin et al. |
| 10,698,922 B2 | 6/2020 | Bormann et al. |
| 10,854,320 B2 | 12/2020 | Fuhrmann |
| 10,910,114 B2 | 2/2021 | Dvorak et al. |
| 11,424,010 B2 | 8/2022 | Hamill et al. |
| 2007/0243537 A1* | 10/2007 | Tuck ............... C12Q 1/6881 435/6.16 |
| 2010/0145903 A1* | 6/2010 | Tuck ............... C11D 3/50 707/769 |
| 2013/0090979 A1* | 4/2013 | Tuck ............... G06Q 30/02 705/7.29 |
| 2013/0226949 A1* | 8/2013 | Ogilvie ............ G06Q 10/06 707/758 |
| 2014/0172498 A1* | 6/2014 | Tuck ............... G06Q 30/0201 705/7.29 |
| 2014/0289536 A1* | 9/2014 | MacCarthy ....... G06F 21/6245 713/189 |
| 2015/0213079 A1* | 7/2015 | Shukla ............. G06F 21/6263 707/687 |
| 2017/0005787 A1* | 1/2017 | Weaver ............ G16B 50/40 |
| 2017/0041132 A1* | 2/2017 | Nicholls .......... H04L 9/0825 |
| 2017/0242961 A1* | 8/2017 | Shukla ............. G16B 50/00 |
| 2018/0350144 A1* | 12/2018 | Rathod ............ G06Q 20/3224 |
| 2020/0175611 A1* | 6/2020 | Gelfand ........... G06F 16/27 |
| 2022/0094520 A1* | 3/2022 | Thumparthy ..... G06F 16/2468 |
| 2023/0207128 A1* | 6/2023 | Chang ............. G16H 40/67 713/189 |
| 2024/0160771 A1* | 5/2024 | Hansen ............ H04L 9/008 |

OTHER PUBLICATIONS

Ananthaswamy, Anil, Hyperdimensional Computing Reimagines Artificial Intelligence, Wired, Jun. 11, 2023, United States.

Baysoy, Alev, The technological landscape and applications of single-cell multi-omics. Nat Rev Mol Cell Biol 24, 695-713 (2023), United States.

Blatt, Marcelo et al., Secure large-scale genome-wide association studies using homomorphic encryption, May 26, 2020, pp. 1-6, vol. 117, No. 21., PNAS, United States.

Carney, Abby, Fed Up With Dating Apps, This Woman Turned to Strava to Find Dates, RunnersWorld, Dec. 16, 2023, pp. 1-6, United States.

Conroy, Gemma, Largest Map of Human Brain yet Reveals Cells Unknown to Science, Nature, Oct. 26, 2023, United States.

Flynn, Meagan, A Harvard Scientist is developing a DNA-based dating app to reduce genetic disease. Critics callled it eugenics., The Washington Post, Dec. 13, 2019, United States.

Heumos, Lukas, et al., Best practices for single-cell analysis across modalities. Nat Rev Genet 24, 550-572 (2023) United States.

Hu, Yuxuan, et al., Unsupervised and supervised discovery of tissue cellular neighborhoods from cell phenotypes. Nat Methods 21, 267-278 (2024) United States.

Huggett, Brady, Joseph LeDoux, the split brain and a traveling magic show, The Transmitter, Jan. 1, 2024, pp. 1-31, United States.

Kim, Miran and Lauter Kristin, Private genome analysis through homomorphic encryption, BMC Medical Informatics and Decision Making, Mar. 16, 2015, San Diego, CA, USA.

Klitzman, Robert L, et al., "In Sickness and in Health"? Disclosures of Genetic Risks in Dating, National Institutes of Health, 2011, pp. 1-23, National Society of Genetic Counselors Inc., United States.

Litwin, David W., Sorry Midjourney, but Image Guidance by Leonardo AI has no Equal . . . Yet., Medium. Nov. 23, 2023, pp. 1-12, United States.

Liu, Mingjie et al., ChipNeMo: Domain Adapted LLMs for Chip Design, NVIDIA, 2023, pp. 1-17, United States.

Lopez Lloreda, Claudia, Wi-Fi for Neurons: First Map of Wireless Nerve Signals Unveiled, Nature, vol. 623, United States.

Lotfollahi, Mohammad et al.,Biologically informed deep learning to query gene programs in single-cell atlases. Nat Cell Biol 25, 337-350 (2023), United States.

Loyfer, Netanel, et al., A DNA methylation atlas of normal human cell types. Nature 613, 355-364 (2023) United States.

Macenski, Steven et al., Robot Operating System 2: Design, architecture, and uses in the wild, Science Robotics, May 11, 2022, pp. 1-20, vol. 7, Issue 66, United States.

Mansky, Jackie, The Dubious Science of Genetics-Based Dating, Smithsonian Magazine, Feb. 14, 2018, pp. 1-10, United States.

Merritt, Rick, Silicon Volley: Designers Tap Generative AI for a Chip Assist, NVIDIA, Oct. 30, 2023, pp. 1-11, United States.

Momin Al Aziz MD, et al., Secure and Efficient Multiparty Computation on Genomic Data, IDEAS, 2016, pp. 1-6, Montreal, QC, Canada.

Nguyen, Eric, et al., HyenaDNA: Long-Range Genomic Sequence Modeling at Single Nucleotide Resolution, Advances in neural information processing systems 36 (2024).

Noor, Poppy, Dating app based on genetic matching not eugenics, scientist says, The Guardian, Dec. 16, 2019, pp. 1-3, United States.

Romera-Paredes, Bernardino et al.,Mathematical discoveries from program search with large language models. Nature 625, 468-475 (2024).

Sarkar, Esha et al., Privacy-preserving cancer type prediction with homomorphic encryption, Scientific Reports, pp. 1-13, United States.

Sim, Jun Jie, et al., Achieving GWAS with homomorphic encryption, 7th iDASH Privacy and Security Workshop, 2018, pp. 1-12, BMC, San Diego, CA, USA.

Stevens, Jan A. et al., Molecular dynamics simulation of an entire cell, Frontiers in Chemistry, Jan. 18, 2023, pp. 1-9, United States.

Sussner, K.M. et al., Ethnic, Racial and Cultural Identity and Perceived Benefits and Barriers Related to Genetic Testing for Breast Cancer among At-Risk Women of African Descent in New York City, Public Health Genomics, 2011, 356-370, Karger, Basel, Switzerland.

Tezduyar, Tayfun E. et al., Fluid-structure interaction modeling of ringsail parachutes,, Springer, Feb. 17, 2008, pp. 1-10, United States.

Voyles Askham, Angie, What 'drifting representations' reveal about the brain, The Transmitter, Dec. 13, 2023, pp. 1-9, United States.

Welle, Elissa, Cortical interneurons derive differently in human brains, The Transmitter, Dec. 20, 2023, pp. 1-8, Simons Foundation, United States.

\* cited by examiner

DISCRETE COMPATIBILITY FILTERING USING GENOMIC DATA

CROSS-REFERENCE TO RELATED APPLICATIONS

Priority is claimed in the application data sheet to the following patents or patent applications, each of which is expressly incorporated herein by reference in its entirety:
None.

BACKGROUND OF THE INVENTION

Field of the Art

The present invention is in the field of genomic data analysis, and more particularly is directed to the problem of discreetly filtering two or more human genomes for compatibility.

Discussion of the State of the Art

Today's computer aided biology endeavors are rapidly seeking to incorporate omics data including genomics, proteomics, metabolomics, metagenomics, phonemics, and transcriptomics. This is particularly true when viewed from the most pragmatic lens, functional genomics, that focuses on describing gene and protein interactions beyond just static DNA sequences or structures inclusive of concepts such as gene translation and transcription, gene expression, protein-protein interactions. One of the tremendous challenges with linking such work at scale is the practical challenges with security, privacy and regulatory compliance efforts associated with such data and the practical elements of considering not just basic bioinformatics workflows around observation, collection, persistence, aggregation, correlation, queries, statistical modeling, and machine learning but also more advanced simulation modeling and artificial intelligence (AI) enabled planning efforts. This is not only important because this broader definition of bioinformatics not only encompasses the current state of data analytics and computational biology concepts but extends them to look at more elements of potential temporal, environmental, and experiential elements impacting functional understanding of omics data and its inclusion in practical wellness and healthcare.

Genetic carrier screening is a relevant exemplary diagnostic procedure that delves into an individual's DNA to ascertain whether they bear an elevated risk of having offspring afflicted with specific genetic disorders, often this is evaluated given the individual's data as well as a prospective mate's DNA profile. Within our genetic makeup, we harbor alterations referred to as variants that possess the potential to trigger genetic conditions and a proactive understanding of such predispositions can aid in personal and medical decision-making. Fortunately, most potentially problematic variants which increase likelihood of disease remain dormant, avoiding significant impact on our personal health or the well-being of our progeny. When they do manifest, awareness of genetic predispositions to disease can speed up diagnosis, treatment, and resolution—with the advent of CRISPR/Cas9 based gene editing therapies such knowledge may also be the gateway for genetic alteration via in vivo, in vitro or ex vivo processes targeting Deoxyribonucleic Acid (DNA) or as demonstrated more recently, Ribonucleic Acid (RNA) and mitochondrial DNA (mtDNA). Genetic carrier screening at present is often primarily concerned with conditions that are hereditary in either an autosomal recessive or X-linked fashion or other potential screening approaches.

In the case of autosomal recessive disorders, both the person who contributes the egg and the one who provides the sperm must carry variants within the same gene to give rise to a child afflicted by that particular condition. Notable instances of autosomal recessive conditions include cystic fibrosis, spinal muscular atrophy, sickle cell disease, and Tay-Sachs disease. For X-linked conditions, carriers contributing their eggs are more likely to have children affected by the condition. It is noteworthy that individuals with XY chromosomes, such as most cisgender males and transgender females, are typically not predisposed to having offspring affected by X-linked conditions. Consequently, many laboratories do not routinely conduct screening for X-linked genes in such cases. Prominent examples of X-linked conditions encompass Fragile X syndrome and Duchenne muscular dystrophy. With the vast reduction in whole genome sequencing costs, we note that whole genome sequencing and democratized access to associated bioinformatics files such as BAM, VCF, FASTA, FASTQ, or SAM files, is rapidly changing the potential for consumer, community, and medical professional access to genomics information. Since our phones, watches, wearables, instrumented homes and offices also provide data, there is now potential for consideration of gene expression and response to environmental and lifestyle factors that can further aid in our understanding of gene and protein interactions at scale and over time.

Best practices for science-driven couples wishing to have children now includes genetic carrier screening. For couples undergoing in-vitro fertilization (IVF) or other fertility assistance, this is often mandatory. Additional preimplantation genetic testing, very recently including whole genome sequencing, can also aid in reproductive, life, and medical decision-making processes. Unfortunately, prior to being ready for children, very few couples understand the degree to which a prospective progeny would be susceptible to material genetically based disease risks and costs. In cases where a couple has progressed from initially meeting, through dating, to serious involvement including possibly marriage, to the point of considering having children, it can be very tragic to learn that some genetic issue raises the prospect of serious risk of fatal birth defects or even the impossibility of having children together. Clearly, if it were technically and socially feasible for couples to understand their genetic compatibility earlier in the process, such difficult situations might be avoided or better managed. In fact, performing genetic screening when initially dating rather than waiting until years later when planning to have children offers several important advantages such as:

Early Awareness: Genetic screening at the beginning of a relationship allows couples to gain awareness of their genetic compatibility and any potential risks long before they decide to have children. This early awareness can help them make informed decisions about their future together or apart-especially when different risk factors may impact the nature, timing or potential for reproduction of a potential partner.

Informed Decision-Making: Knowing their genetic status enables couples to make informed decisions about their relationship and family planning. If both individuals are carriers for a specific genetic condition, they can discuss their options and potential challenges from the outset. Since cost is a leading factor in reproductive decision-making, probabilistic weightings of disease expression, treatments and outcomes may also aid couples or broader families in their consideration of starting a "next" generation.

Emotional Preparation: Genetic screening early in a relationship provides couples with the opportunity to emotionally prepare for any potential challenges related to their genetic compatibility. This can reduce the shock and stress that may occur when discovering genetic risks later on. It may also help avoid statistically improbable, but potentially devastating, issues like determining shared genetic lineage whether through natural or assisted reproduction since some extreme cases indicate upwards of 550 offspring from single individuals.

Time for Evaluation and Counseling: Couples who undergo genetic screening during dating have more time to seek genetic and medical counseling, consult with healthcare professionals, and explore their reproductive options or discuss potential challenges with family or spiritual support systems that may be impacted. This allows for a comprehensive understanding of the implications of their genetic status in major personal, family, community, and financial decisions.

Potential Alternatives: Early screening may reveal that one or both partners are carriers of certain genetic conditions. This knowledge can prompt discussions about alternative family planning methods, such as adoption or assisted reproductive technologies (including more advanced screening of potential embryos during IVF or offspring in vivo), which may be preferable for some couples.

Relationship Planning: Genetic screening results can also influence long-term relationship planning. Couples can consider whether they are prepared to navigate potential challenges associated with genetic risks and whether they want to invest in the necessary support and care needed.

Reduced Stress: Couples who have already addressed potential genetic concerns can experience reduced stress and anxiety when they eventually decide to have children, as they have already taken steps to understand and manage any risks or costs.

Supportive Environment: Openly discussing genetic screening early in a relationship fosters an environment of trust and communication. Couples can work together to make decisions that align with their values and goals. Additionally, genetic information might be optionally persisted for the availability of any future offspring to aid them in their own healthcare decisions if needed.

Potential Reduced Fertility Treatment Costs: Reducing the potential for infertility, miscarriage or complications and better leverage and incorporate preimplantation genetic testing (PGT; a screening test that can be performed on embryos created via in vitro fertilization IVF to genetically analyze the embryos prior to transfer) or in vivo genetic sampling and testing.

Genetic screening during the early stages of dating allows couples to make informed choices about their future, consider alternatives, and emotionally prepare for any challenges related to their genetic compatibility. It promotes open communication and proactive decision-making, ultimately leading to a healthier and more supportive relationship dynamic and mitigating or potentially avoiding painful situations like an inability to have children without catastrophic risks or costs after years of investment in a relationship. In a much more pedestrian example, it may also be used to aid in refining things as mundane as grocery shopping, suggested recipes, or travel planning (e.g., for a date or a trip) by noting potential indicators of allergies, lactose intolerance, or other factors that might necessitate or encourage alternate decisions. For example, not going to fondue and ice cream if lactose intolerance is likely based on genetic indicators around LCT gene for lactase enzyme production.

What is needed are methods and systems for discretely filtering two or more genomes for compatibility and risk factors. In order to achieve this, what is also needed is a scalable platform for creating and using personal health databases (PHDBs) in support of discretely filtering two or more genomes for compatibility and evaluate potential health risks to the prospective individuals or their offspring.

SUMMARY OF THE INVENTION

Accordingly, the inventor has conceived and reduced to practice methods and systems for evaluating characteristics of two or more human genomes for compatibility, potential risk factors, gene expression and probabilistic future health outcomes.

According to a preferred embodiment, a computer-implemented method executed on a platform for discretely filtering and evaluating two or more human genomes for compatibility and risk scoring, the computer-implemented method comprising: upon receiving a filtering request from a device associated with a user, filter across multiple elements, activities, and platforms to connect with a prospective mate; providing selective opt-in screening accommodating user-specific preferences, facilitating engagement with multiple applications using common omics, environmental, and lifestyle data; implementing cloud-based or edge-based processing, making the invention robust to periodic or sporadic connectivity and data processing needs and types; adapting analysis and visibility conditions based on user preferences, regulations, laws, or application/community rules, with configurable alerts for positive or negative matches; incorporating a secure and privacy preserving homomorphic or regular encrypted omics data and personal lifestyle, activity, and environmental exposure into a personal health database cloud or edge-based processing system; utilizing a plurality of encrypted genomic and omics data within the cloud or edge-based processing system to perform screening on human omics datasets using a homomorphically encrypted algorithm, employing suitable approximations for isolated, semi-parallel, or parallel Genome Wide Association Study (GWAS); leveraging the complex space of homomorphic encryption methods enabling direct computations on the encrypted data, increasing the number of single nucleotide polymorphisms (SNPs), mutations, or other modifications in DNA, RNA, mtDNA of people or microbiome elements that can be packed within a ciphertext; calculating the genetic compatibility scores for the individuals determining susceptibility of hereditary conditions in future offspring, assessing potential genetic risks and associated life impacts, costs, and longevity considerations in progeny or prospective partner; and uploading the calculated results, displaying the genetic compatibility, through results or suggestions, to the end user while limiting disclosed data to user authorized information.

According to another preferred embodiment, a computing system for discretely filtering and evaluating two or more human genomes for compatibility and risk scoring, the computing system comprising: one or more hardware processors configured for: upon receiving a filtering request from a device associated with a user, filter across multiple elements, activities, and platforms to connect with a prospective mate; providing selective opt-in screening accommodating user-specific preferences, facilitating engagement with multiple applications using common omics, environmental, and lifestyle data; implementing cloud-based or edge-based processing, making the invention robust to periodic or sporadic connectivity and data processing needs and types; adapting analysis and visibility conditions based on user preferences, regulations, laws, or application/community rules, with configurable alerts for positive or negative matches; incorporating a secure and privacy preserving homomorphic or regular encrypted omics data and personal lifestyle, activity, and environmental exposure into a personal health database cloud or edge-based processing system; utilizing a plurality of encrypted genomic and omics data within the cloud or edge-based processing system to perform screening on human omics datasets using a homomorphically encrypted algorithm, employing suitable approximations for isolated, semi-parallel, or parallel Genome Wide Association Study (GWAS); leveraging the complex space of homomorphic encryption methods enabling direct computations on the encrypted data, increasing the number of single nucleotide polymorphisms (SNPs), mutations, or other modifications in DNA, RNA, mtDNA of people or microbiome elements that can be packed within a ciphertext; calculating the genetic compatibility scores for the individuals determining susceptibility of hereditary conditions in future offspring, assessing potential genetic risks and associated life impacts, costs, and longevity considerations in progeny or prospective partner; and uploading the calculated results, displaying the genetic compatibility, through results or suggestions, to the end user while limiting disclosed data to user authorized information.

According to another preferred embodiment, a system for discretely filtering and evaluating two or more human genomes for compatibility and risk scoring, comprising one or more computers with executable instructions that, when executed, cause the system to: upon receiving a filtering request from a device associated with a user, filter across multiple elements, activities, and platforms to connect with a prospective mate; provide selective opt-in screening accommodating user-specific preferences, facilitating engagement with multiple applications using common omics, environmental, and lifestyle data; implement cloud-based or edge-based processing, making the invention robust to periodic or sporadic connectivity and data processing needs and types; adapt analysis and visibility conditions based on user preferences, regulations, laws, or application/community rules, with configurable alerts for positive or negative matches; incorporate a secure and privacy preserving homomorphic or regular encrypted omics data and personal lifestyle, activity, and environmental exposure into a personal health database cloud or edge-based processing system; utilize a plurality of encrypted genomic and omics data within the cloud or edge-based processing system to perform screening on human omics datasets using a homomorphically encrypted algorithm, employing suitable approximations for isolated, semi-parallel, or parallel Genome Wide Association Study (GWAS); leverage the complex space of homomorphic encryption methods enabling direct computations on the encrypted data, increasing the number of single nucleotide polymorphisms (SNPs), mutations, or other modifications in DNA, RNA, mtDNA of people or microbiome elements that can be packed within a ciphertext; calculate the genetic compatibility scores for the individuals determining susceptibility of hereditary conditions in future offspring, assessing potential genetic risks and associated life impacts, costs, and longevity considerations in progeny or prospective partner; and upload the calculated results, displaying the genetic compatibility, through results or suggestions, to the end user while limiting disclosed data to user authorized information.

According to another preferred embodiment, non-transitory, computer-readable storage media having computer instructions embodied thereon that, when executed by one or more processors of a computing system employing platform for discretely filtering and evaluating two or more human genomes for compatibility and risk scoring, cause the computing system to: upon receiving a filtering request from a device associated with a user, filter across multiple elements, activities, and platforms to connect with a prospective mate; provide selective opt-in screening accommodating user-specific preferences, facilitating engagement with multiple applications using common omics, environmental, and lifestyle data; implement cloud-based or edge-based processing, making the invention robust to periodic or sporadic connectivity and data processing needs and types; adapt analysis and visibility conditions based on user preferences, regulations, laws, or application/community rules, with configurable alerts for positive or negative matches; incorporate a secure and privacy preserving homomorphic or regular encrypted omics data and personal lifestyle, activity, and environmental exposure into a personal health database cloud or edge-based processing system; utilize a plurality of encrypted genomic and omics data within the cloud or edge-based processing system to perform screening on human omics datasets using a homomorphically encrypted algorithm, employing suitable approximations for isolated, semi-parallel, or parallel Genome Wide Association Study (GWAS); leverage the complex space of homomorphic encryption methods enabling direct computations on the encrypted data, increasing the number of single nucleotide polymorphisms (SNPs), mutations, or other modifications in DNA, RNA, mtDNA of people or microbiome elements that can be packed within a ciphertext; calculate the genetic compatibility scores for the individuals determining susceptibility of hereditary conditions in future offspring, assessing potential genetic risks and associated life impacts, costs, and longevity considerations in progeny or prospective partner; and upload the calculated results, displaying the genetic compatibility, through results or suggestions, to the end user while limiting disclosed data to user authorized information.

According to an aspect of the embodiment, at least a portion of genetic screening allows for user opt in prior to sharing a subset of data.

According to an aspect of the embodiment, at least a portion of the dataset sensitive data is removed, obfuscated, anonymized, or otherwise limited.

According to an aspect of the embodiment, at least a portion of screening process allows users to declare preferences including genetic factors prior to sharing data.

According to an aspect of the embodiment, at least a portion of screening process allows users to declare preferences including emotional factors, health concerns, medical treatment, or reproductive assistance preferences prior to sharing data.

According to an aspect of the embodiment, at least a portion of screening process allows users to declare medical or lifestyle preferences including religious factors prior to sharing data.

According to an aspect of the embodiment, at least a portion of screening process allows users to declare medical or lifestyle preferences including religious factors prior to sharing data.

According to an aspect of the embodiment, at least a portion of the ability for multiple applications, such as mobile sensors, third party applications, biometrics, and similar applications to engage with common data.

According to an aspect of the embodiment, at least a portion of the data includes single-nucleotide polymorphism (SNP), DNA, RNA, mtDNA, and microbiome data.

According to an aspect of the embodiment, at least a portion of the display is comprised of wearable devices, mobile devices, videoconferencing or holograph devices, computers, Internet-of-Things devices, gaming platforms or devices, and augmented reality or virtual reality systems.

BRIEF DESCRIPTION OF THE DRAWING FIGURES

DETAILED DESCRIPTION OF THE INVENTION

Figure 1:
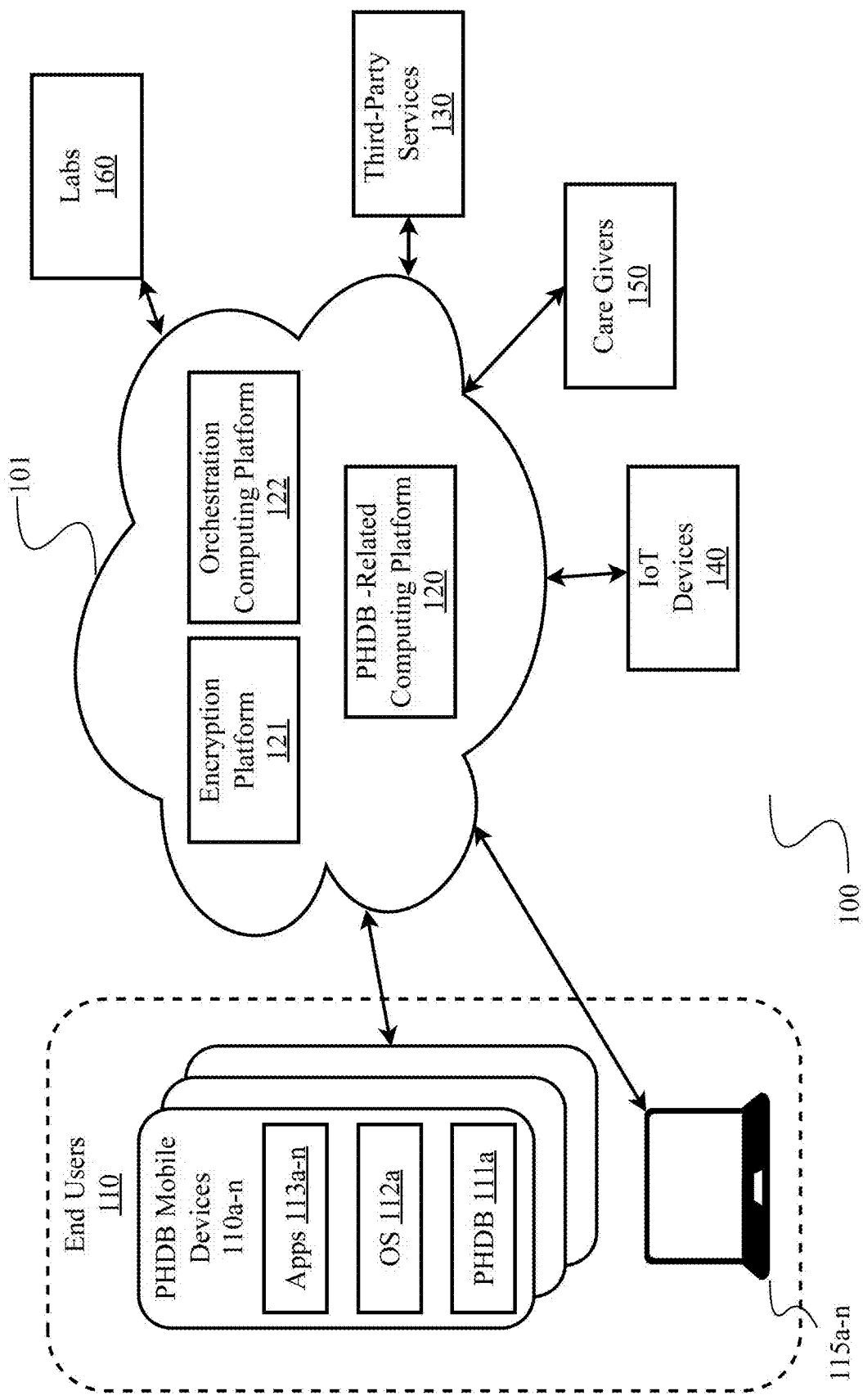
FIG. 1 is a high-level architecture diagram of an exemplary system for discretely filtering two or more human genomes for compatibility and risk using personal health databases (PHDBs), according to an aspect of the invention.

The inventor has conceived, and reduced to practice, methods, and systems for discretely filtering two or more human genomes for compatibility, which enable users to engage in proactive filtering across multiple elements/activities/platforms where they may engage with a prospective mate. Such systems and methods need to be able to accommodate selective degrees of "opting in" to screening processes and the ability for multiple applications to engage with common data. Setting and enforcing of user-specific preferences should also be available (e.g., specific kinds of "deal breaker" criteria or scores or preferences for either party if "screening mode" is enabled). The invention may use cloud-based or edge-based processing (e.g. on a local mobile device). The invention is robust to periodic or sporadic connectivity (e.g., available during a remote hike), and to the complexity of the issues associated with identifying a given counterparty both digitally and physically linking them to a specific persona and health record. The invention may enable both attempts at automated recognition or identification of potential mates with probabilistic confidence (i.e., suggest a partner and "silently" screen) as well as proactive use cases (i.e., "can we check compatibility").

According to various aspects of the invention, user declarations of preferences about genetic, emotional, religious, or behavioral kinds of preferences or constraints can be stored and leveraged by computer-enabled processes to aid users in real-world interactions as well as in augmented reality and/or metaverse engagement (i.e. simulated worlds or gaming). This may be through reports, suggestions regarding prospective interactions, in-app or "anti-app" dynamically generated user interface (UI) prompts, device feedback (e.g. haptics that buzz when close to a prospect that is compatible), or engagement with other applications, services, wearables, or hardware. It is worth noting that user preferences, regulations, laws, or application/community rules may also set conditions for different "visibility" conditions and how such identified matches may be presented to the user (for example, a "negative match" warning may be preferred in some settings as opposed to a positive match encouragement. For example, a negative only warning configuration could avert a future "incompatibility" disaster (e.g. common parent or unknown cousin status) behind the scenes without otherwise shaping/encouraging prospective relationship development.

The ability to change the nature, location, and specificity of potential alerts (positive or negative) is also based on the degree to which data sharing is enabled directly from others (e.g. mobile devices), intermediaries (e.g. MATCH.COM, BUMBLE, TINDER, or LINKEDIN or Peloton or Reddit), but also from public data (e.g. public writings, persona, photos, etc.). According to an aspect, direct disclosure (e.g. of medical condition or ethnicity or toxic exposure) might also be estimated by some statistical or artificial intelligence or machine learning (AI/ML) methods. For example, generative AI (GenAI) might "guess" at prospective profiles (even genetic ones) based on indicators (e.g. specific ethnic background, food eaten, activities, localities, etc.) that may be available to the system from private or public sources (including web scraping). This can be used to probabilistically profile others, even if they are not opting into such a system to aid at least one user. This can be further enhanced by incorporating other models or data sets or other research publications that might be available for licensure in some fashion (e.g., 23ANDME or ANCESTRY.COM or proprietary datasets such as from drug companies doing studies on specific drugs or molecules) for genotyping or whole genome processing/guessing about a whole genome, or elements including but not limited to SNPs, STRs, mtDNA, RAW data. Various aspects might also generate profiles that are more limited (e.g. genotype guesses vs whole genome) based on cost or on the stage of a relationship. Systems and methods of the invention might also be used for identification of prospective organ donors or blood donors during normal human interactions. This could enable much more efficient search processes within "normal" community interactions for bone marrow, organs, and so forth, or for potential "directed" organ donation options for families/friends. This could also enable opt-in solicitation for organ and tissue donations as this may vastly improve potential for either direct use in medical procedures or may serve as a basis or seed for other advanced treatments that rely on emerging technologies like 3d printing of cellular tissue.

According to an aspect of the invention, the secure and privacy-preserving genetic compatibility assessment may be optionally enhanced with partial or full homomorphic encryption. In such aspects, the system can leverage collected genetic information to calculate encrypted compatibility scores for groups or pairs of individuals without revealing sensitive details. These scores, reflecting the predicted compatibility based on analyzed genetic factors, provide users with an additional data point to guide their decision. These scores (or suggestions, reports, dashboards, risk factors or predictions) based on analyzed genetic factors without revealing raw data, provide users with another valuable piece of information for deciding whether to reveal their full identities and genetic information to promising (high scoring) matches and deepen their connection. This same approach may enable faster and more efficient sourcing of potential candidates for medical studies of drugs, therapeutics, surgeries or other treatments (including emerging CRISPR/Cas9) where new studies, approvals (e.g. drug or gene therapy or radiation) might receive feeds of relevant academic, regulatory, legal, commercial or government actions related to omics factors identified in their personal health database or those of others with whom they have visibility (e.g. spouse, child, parent, friend, or group).

According to an aspect of an embodiment, the platform can support "search: operations on (user) authorized data for analysis privately i.e., some people might enable homomorphic studies on their data by only want to receive "blind" approaches based on their data being of interest. This may be applied to user data such as tissue/blood/etc. donations as well as potential fits for treatments and/or therapies. This "inbound" queue may be able to be optionally routed to an AI engine for recommendation/evaluation and also to their primary cate physician or other medical team members as configured in their health records in the personal health database or their broader existing medical chart system like EpicMyChart. The platform can support such functionality by allowing individuals to authorize the use of their data for analysis privately. This can include using techniques like homomorphic encryption to allow for analysis without revealing the raw data. Platform may implement an inbound queue where data requests or queries can be submitted. This queue should be able to handle requests for analysis based on authorized data and route them to the appropriate destination.

According to another embodiment, user declarations of preferences and regulatory conditions, offering a flexible and adaptive approach to genetic screening in the real-world, augmented reality, and metaverse contexts. The user also can change the nature, location, and specificity of potential alerts which is also based on the degree to which data sharing is enabled from others, intermediaries, and from public data. Direct disclosure might be estimated by statistical, artificial intelligence or machine learning methods and made available for review or sent via communications including but not limited to on-device push notifications, text messages, chat messages, voicemails, emails, physical mail, or engagement in the physical world with meetings or mailings or digital content (e.g. ads on computer or television or devices).

According to an aspect of the embodiment is that the systems and methods of the invention may be used for identification of prospective organ donors or blood or tissue donors during normal human interactions or via public (or private) listings which could enable much more efficient search processes within normal community interactions for tissue, blood, bone marrow, or organs or genetic material for healthcare or reproductive purposes. It should be noted that system may also be configured to have reference contracts for common elements (e.g. blood donor, tissue donor, marrow donor, sperm or egg donor, surrogate services) that might be aid counterparties in arranging for additional verification or transacting (conditional on medical professional approvals) directly in the PHDB or via sharing the PHDB with another application or service.

It should be appreciated that while a human genome is generally used throughout the specification when referring to genomic data and analysis thereof, it does not limit the disclosed systems and methods to the processing of human omic data. Such systems and methods may be directed to the omic data of other animals and not limited to human omic data. Such systems and methods may find utility in the field of veterinary services.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable in numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods, and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

As used herein, "homomorphic encryption" refers to the cryptographic technique that allows computations to be performed on encrypted data without decrypting it first. It enables certain operations to be carried out on encrypted data while in ciphertext as if it were still in its original form, and the results are obtained in encrypted form.

Conceptual Architecture

FIG. 1 is a high-level architecture diagram of an exemplary system for discretely filtering two or more human genomes for compatibility and risk using personal health databases (PHDBs), according to an aspect of the invention. As shown in FIG. 1, system 100 offers accessibility to a variety of entities including end users 110, Internet of Things (IoT) devices 140, Care Givers 150, Third-Party Services 130, and Labs 160 by connecting to various cloud-based 101 platforms (e.g., systems, subsystems, and/or services) via a suitable communication network such as the Internet. End Users 110 have flexibility, choosing to engage in cloud-based processing through either their Personal Computers 115a-n which may connect to the cloud-based platforms 101 via a browser-based website or web application, or PHDB-enabled Mobile Devices 110a-n (e.g., smart phone, tablet, smart wearable clothing or glasses, headsets etc.). These mobile devices may comprise a PHDB 111a, an operating system (OS) 112a, and various applications (Apps) 113a-n, creating a comprehensive environment for users to manage and interact with their health and preference data. The ability to have authorized disclosure rules and suggestions or delegate sharing and visibility for personal health records or conditions can also vastly simplify medical procedures and improve outcomes for patients. Current systems force patients into cumbersome manual and often paper disclosure certifications (e.g., outpatient surgery procedure) but could instead be configured to send appropriate status and visibility (even for physical visitation rights in hospital) data to family and friends. This can also better enable post-operative and non-medical facility care by enabling family and friend and personal uploads to the PHDB of photos, interactions, observations, sensor data which can be made available to PHDB processes or to medical staff supporting outcomes.

A user of the system may collect various personal consumption, environment, activity, and other health-related data from a plurality of sources and store the data in their personal health database. Personal health-related data can include genetic information and medical information associated with the user, as well as other types of biometric, behavioral, and/or physiological information. Personal health-related data may be obtained from various sources including, but not limited to, labs 160, third-party services 130, care givers 150, and IoT devices 140. For example, genetic information may be obtained from a lab 160 that conducts genetic carrier screening (e.g., autosomal dominant, autosomal recessive, X-linked dominant, X-linked recessive, mitochondrial, etc.) for a user. Ongoing urine data may be fed from Withings new urine sensor kit, body scan data from an at home body scanner/scale, temperature data from thermal cameras or thermometers, sleep data from smart mattress covers, snoring and sleep quality and sleep apnea indicators from wearable microphones along with heart rate and blood oxygen levels, et cetera. Best practices for individuals or couples wishing to improve personal health outcomes or shared goals such as having children now can include genetic indicator monitoring (e.g. for new papers and research) as well as lived experiences and exposures that may enhance or reduce their risk of adverse health outcomes.

Genetic testing can play a significant role in medical treatment. Some common types of genetic tests that can produce genetic information that can be stored in an individual's PHDB can include diagnostic testing, carrier testing, prenatal testing, newborn screening, pharmacogenetic testing, predictive and presymptomatic testing, forensic testing, and research genetic testing. Diagnostic testing is used to identify or rule out a specific genetic or chromosomal condition. It is done when there is a suspicion based on symptoms or family history. Carrier testing is used to determine if a person carries a gene for a genetic disorder. This type of testing is often done in people with a family history of genetic disorder or in specific ethnic groups with a higher risk. Prenatal testing is conducted during pregnancy to detect genetic abnormalities in the fetus. Examples include amniocentesis, chorionic villus sampling (CVS), and non-invasive prenatal testing (NIPT). Newborn screening involves a series of tests performed on newborns to detect certain genetic disorders early, allowing for early intervention and treatment. Pharmacogenetic testing analyzes how an individual's genes affect their response to certain medications. This information can help personalize medication dosages and selection. Predictive and presymptomatic testing is used to identify genetic mutations associated with conditions data develop later in life, such as certain types of cancer. Presymptomatic testing is done in individuals who do not yet have symptoms but have a family history of a genetic disorder. Forensic testing is used for identification purposes, such as in criminal investigations or paternity testing. Research genetic testing is conducted as part of research studies to better understand the roles of genetics in health and disease. These tests can provide valuable information for healthcare providers, care givers, individuals, and prospective mates.

In some implementations, labs 160 may comprise a plurality of types of labs and facilities that could gather genetic, biometric, behavioral, and/or physiological data on a user. Exemplary labs/facilities can include, but are not limited to, research laboratories (e.g., often affiliated with universities or research institutions and conduct studies to gather various types of data), biotechnology companies, healthcare facilities (e.g., hospitals, clinics, and other healthcare facilities may gather data as part of patient care or research studies. This data could include information from medical tests, imaging studies, and patient questionnaires), tech companies (e.g., wearable technology industry), government agencies, and consumer research firms.

According to the embodiment, caregivers 150 may also provide information to PHDB about the individual which they are providing care for. A caregiver, depending on their role and the context of care, may be responsible for a wide range of medical information. Some common types of medical information that a caregiver might know about or be responsible for include, but are not limited to, patient history (e.g., information about past illnesses, surgeries, medications, allergies, and family medical history), current health status (e.g., information about the patient's current health, including any ongoing medical conditions, symptoms, and vital signs such as blood pressure, heart rate, and temperature), medications (e.g., information about the medications the patient is taking, including dosage, frequency, and any special instructions), treatment plans (e.g., information about the patient's treatment plan, including any medications, therapies, or procedures that have been prescribed), progress notes (e.g., notes on the patient's progress, including any changes in their condition, response to treatment, or other relevant information), diagnostic tests (e.g., information about any diagnostic tests that have been performed, such as blood tests, imaging studies, or biopsies, and the results of those tests), care plan (e.g., information about the overall plan of care for the patient, including goals, interventions, and follow-up care), patient education (e.g., information about legal and ethical issues related to the patient's care such as advance directives, consent for treatment, and confidentiality), and coordination care (e.g., information about coordination of care with other healthcare providers, including referrals, consultations, and care transitions). The specific medical information that a caregiver is responsible for and can provide to the PHDB of their patient will vary depending on the setting and scope of their practice, as well as the needs of the patient.

According to the embodiment, cloud-based platforms 101 may integrate with various third-party services 130 to obtain information related to a user's genetics, biometrics, behavior, and/or physiological characteristics. For example, platform 101 may obtain an electronic health record (EHR), or a subset thereof, associated with the user for inclusion in the user's PHDB.

Additionally, a PHDB mobile device 110a-n may comprise a plurality of sensors which may be used to monitor and capture various biometric, behavioral, and/or physiological data associated with the owner (end user) of the PHDB mobile device. Captured sensors data may be stored in PHDB 111a either in raw data form, or in a format suitable for storage after one or more data processing operations (e.g., transformation, normalization, etc.) has been performed on the sensor data. In some embodiments, a purpose-built software application 113a-n configured to collect, process, and store various sensor data (e.g., biometric, behavioral, physiological, etc.) obtained by sensors embedded into or otherwise integrated with PHDB mobile devices 110a-n. Some exemplary sensors that may be embedded/integrated with PHDB mobile device can include, but are not limited to, fingerprint sensor, facial recognition sensor, heart rate sensor, accelerometer, gyroscope, continuous glucose monitor (CGM), Global Positioning System (GPS), microphone, camera, light sensor, electromagnetic sensors, barometer, pedometer/step counter, galvanic skin response (GSR) sensor (e.g., measures skin's electrical conductivity, which can vary with emotional arousal, stress, or excitement), temperature sensor, lidar, and infrared sensor. More advanced sensors might include Raman-based real-time analytics, gas chromatography mass spectrometry, liquid chromatography mass spectrometry, capillary electrophoresis mass spectrometry, which may be of particular use in environmental exposure considerations in health conditions and lived gene expression. These sensors can be used individually or in combination to gather a wide range of data about the user's biometric, behavioral, and physiological characteristics, enabling various applications such as health monitoring, fitness tracking, personalized user experiences, and human genome filtering for compatibility, to name a few. It is important to note that when combined with temporal and graph representations of interactions in the individual's life, this can feed into a much more nuanced biological monitoring, modeling and simulation aid available for personal, family, or medical use. Users who gather such data fastidiously may also be of particular interest to researchers in support of uncertainty reduction and isolation of particular genetic linkages to this litany of more comprehensive lived factors commonly excluded from static genomics analysis.

In some embodiments, PHDB 111a may be stored in the memory of PHDB mobile or wearable device 110a. In some embodiments, PHDB 111a may be implemented as an encrypted database wherein the plurality of personal health data stored therein is cryptographically encrypted to protect the personal and sensitive data stored therein.

End users 110 may also engage in edge-based processing referring to computing devices that process data closer to the source of data generation instead of relying solely on a centralized server. Edge devices are situated close to the point where data is generated, such as sensors, cameras, or other Internet of Things devices. The Internet of Things (IoT) 140 devices refer to physical objects embedded with sensors, software, and other technologies that enable them to connect and exchange data over the internet. These devices are part of the broader concept of the Internet of Things, which involves the interconnection of everyday objects to the Internet, allowing them to collect and share data for various purposes. Internet of Things devices find applications in various domains, including smart homes, healthcare, industrial automation, agriculture, transportation, and more. Examples include smart thermostats, wearable health monitors, industrial sensors, and connected vehicles. According to the embodiment, a plurality of IoT devices 140 may be deployed to collect and transmit various types of information related to a user's genetics, biometrics, behavior, and/or physiological characteristics. In some implementations, IoT devices 140 can include a plurality of sensors, devices, systems, and/or the like configured to collect and transmit data to cloud-based platforms 101 for inclusion in the user's PHDB. Some exemplary IoT devices 140 can include fitness trackers, smart scales, smart clothing, smart home devices, genetic testing kits, sleep monitors, health monitoring devices (e.g., devices that measure health parameters such as blood pressure, glucose levels, and oxygen saturation, etc.), and wearable cameras.

To facilitate proactive filtering across multiple platforms during interactions with prospective mates, the cloud 101 integrates an optional encryption platform 121, an orchestration computing platform 122, and a PHDB-related computing platform 120.

According to the embodiment, an optional encryption platform 121 may be configured and deployed to provide strong encryption to protect data from unauthorized access. In addition to using strong encryption algorithms, encryption platform 121 is configured to follow best practices for key management, such as using strong, randomly generated encryption keys, and regularly rotating keys to minimize the risk of unauthorized access. In an embodiment, encryption platform 121 may implement advanced encryption standard (AES) for encrypting the various data stored in PHDB. AES is a symmetric encryption algorithm that is widely used and considered to be very secure. It is often used to encrypt data at rest, such as files stored on PHDB. In an embodiment, encryption platform 121 may utilize RSA which is an asymmetric encryption algorithm commonly used for encrypting data in transit, such as data sent over the Internet. In another embodiment, elliptic curve cryptography (ECC) may be implemented which is an asymmetric encryption algorithm that is known for its efficiency and security. In some embodiments, ECC may be used to encrypt data obtained and transmitted by IoT devices 140 to cloud-based platforms 101. In some implementations, a combination of encryption schemes may be utilized to provide secure data storage and transmission. For example, personal-health data may be encrypted in the cloud using RSA and then sent to an end user mobile device 110a wherein it may be encrypted using AES for storage on PHDB 111a of the mobile device.

In some embodiments, encryption platform 121 may implement homomorphic encryption when processing or otherwise analyzing personal health information. In this way, the system can provide processing of encrypted data without having to decrypt and potentially leak personal information.

An orchestration platform 122 is present and configured to provide automated management, coordination, and execution of complex tasks or workflows. This can involve deploying and managing software applications, provisioning and managing resources, and coordinating interactions between different components of system 100. Orchestration platform 122 may automate the deployment and management of virtual machines, containers, and other resources. This can include tasks such as provisioning servers, configuring networking, and scaling resources up or down based on demand. For example, orchestration platform 122 may define and execute a workflow related to the collection, encryption, and distribution (to the appropriate PHDB) of user health-related information. Of particular importance is the ability of the platform to interact with AI/ML systems to aid in explaining, modeling, extracting models, or generating potential items of interest for consideration by medical experts or users. This is further enhanced by the ability for automated planning and modeling simulation services to consider forward scenario analysis of factors (e.g., what if I stopped eating bacon every morning and walked a minimum of 15,000 steps per day instead of my current activity level). This may also help generate financial models to aid users in their personal decision-making and potentially for insurers or medical professionals in theirs. This is becoming more important in the emerging CRISPR/Cas9 and with sudden emergence of Ozempic and Zapbound era. This is likely to become more challenging for payers, patients and providers if the expected multireceptor agonists such as LY3437943 (a novel triple agonist peptide at the glucagon receptor (GCGR), glucose-dependent insulinotropic polypeptide receptor (GIPR), and glucagon-like peptide-1 receptor (GLP-1R)), emerge and potentially offer large benefits to at risk populations with severe disease and broad-based disease risk factor reductions. Such financial "what if" scenarios will become important when considering the lifetime value of treatment options and potential payment models and is critical to improving patient outcome and better managing continuity of care for healthier and ultimately cheaper patients.

Figure 2:
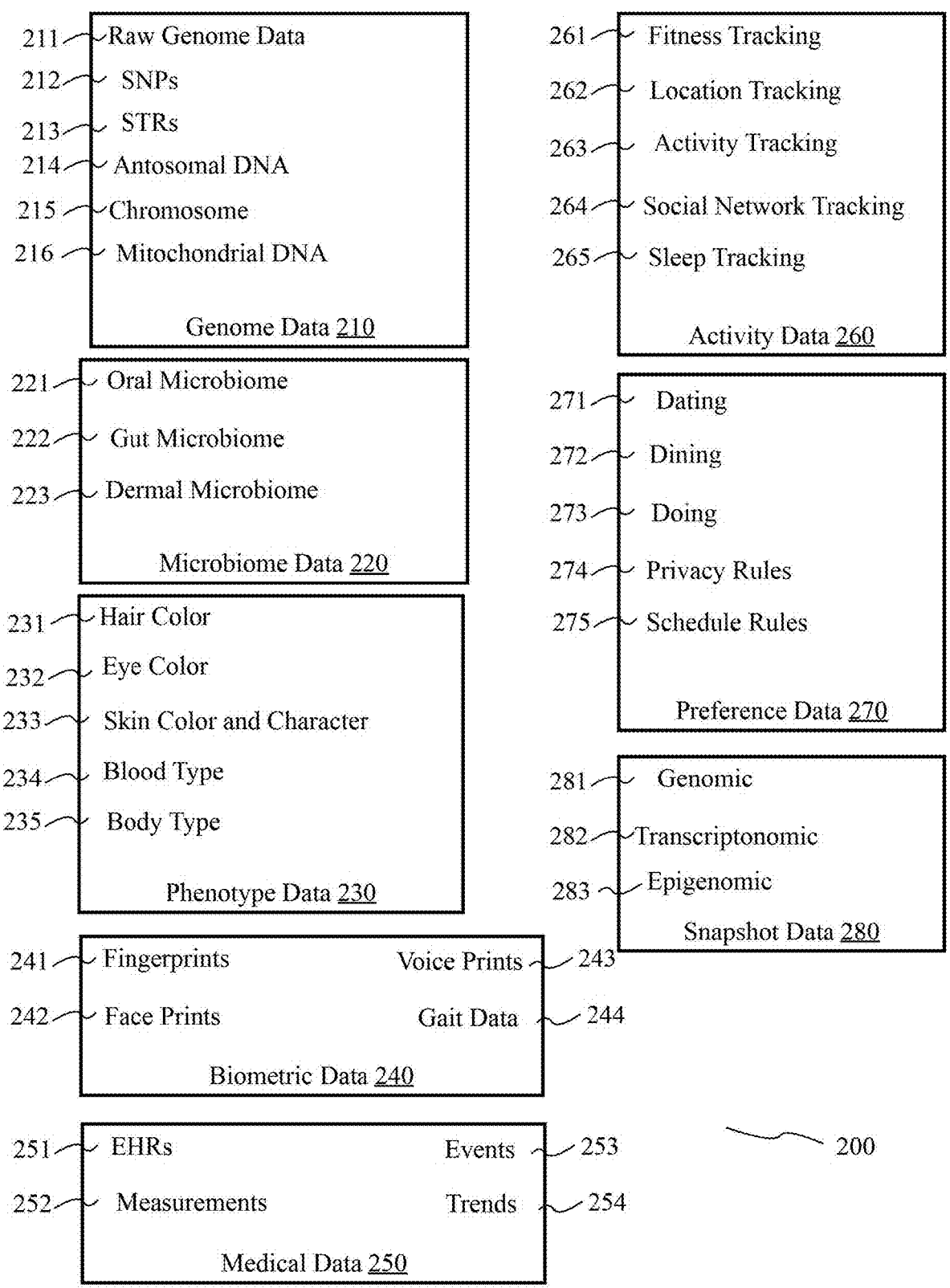
FIG. 2 is a diagram showing an exemplary arrangement of a PHDB, according to an aspect of the invention.

FIG. 2 is a diagram showing an exemplary arrangement of a personal health database (PHDB), according to an aspect of the invention.

In at least one aspect of an embodiment, a personal health database may be implemented as a cloud-based storage system for storing personal health-related information designed for security, scalability, and privacy.

In at least one aspect of an embodiment, a personal health database may be implemented as a database for storing personal health-related information stored in the memory (or some other storage system) of a PHDB mobile device 110a.

Regardless of the implementation, the system may require secure authentication mechanisms (e.g., username/password, two-factor authentication) to ensure that only authorized users can access the data. Role-based access control can be used to manage permissions for different types of users (e.g., patients, healthcare providers). Each individual can set their PHDB permissions with respect to other individuals or entities (e.g., that is who can access the data, other people, other applications or services, etc.) and scope (e.g., how much data can permit individuals access). All data stored in the system may be encrypted (such as by encryption platform 121) both in transit and at rest to protect it from unauthorized access. This can include using strong encryption algorithms such as AES, and in some implementations, homomorphic encryption. Personal health information can be segmented into categories (e.g., medical records, lab results, prescriptions, genome data, microbiome data, phenotype data, biometric data, activity data, preference data, etc.) to facilitate access control and data management. The system can be designed to handle a plurality of users and a large volume of data. This involves leveraging scalable cloud infrastructure and database technologies. In some implementations, mechanisms may be put in place to ensure the integrity and availability of the data, including regular backups and redundancy. The storage system may be configured to comply with relevant regulations and standards for health information privacy and security, such as the Health Insurance Portability and Accountability Act (HIPAA) in the United States. Additionally, the storage system may maintain detailed audit logs of all access and modifications to the data for accountability and compliance purposes.

According to some embodiments, the PHDB system comprises a user-friendly interface (e.g., graphic user interface) for users to access and manage their health information, as well as for healthcare providers to view and update patient records, if applicable. For example, a software application stored and operating on PHDB mobile device 110a may provide a user interface where PHDB mobile device users can manage their stored personal-health information including uploading new information, editing existing information, and setting permissions/managing access control over their stored personal health information. Overall, the PHDB system provides a secure and reliable platform for storing personal health information while ensuring that it remains accessible to authorized users when needed for personal, family, group or medical purposes.

Personal health information can be segmented into content categories 200 to facilitate access control and data management to be able to accommodate selective degrees of "opting in" to screening processes and the ability for multiple applications to engage with common data. This may further enable user-specific preferences such as, for example, specific "deal breakers" for either party if a "screening mode" is enabled. Similar users may authorize their data for evaluation by third parties with designated filters via rules, criteria or models (AI/ML or statistical) for approaching them or their medical providers with prospective requests, data use asks, or as a candidate for studies, treatments, or therapies.

PHDB content categories 200 may include, but are not limited to, genome data 210 which encompasses a diverse set of genetic information critical for understanding an individual's biological makeup. The subcategories can include the raw genome data 211, which is the complete genomic sequence of an individual, the single nucleotide polymorphisms (SNPs) 212, which are variations at the level of a single nucleotide, the short tandem repeats (STRs) 213, which are tandemly repeated DNA sequences, autosomal DNA 214, which are non-sex chromosome DNA, chromosome 215, which are individual chromosomes contributing to the genome, and mitochondrial DNA 216 which is genetic information from mitochondria. Additionally, genome data 210 can comprise an individual's RNA, DNA, and/or mtDNA data. A use case for such data is genetic alteration via in vivo, in vitro, or ex vivo processes targeting RNA, DNA, and/or mtDNA. Furthermore, genomic data 210 may comprise multiple instances of genomes in an individual's life. For example, if an individual gets a CRISPR/Cas9 therapy then the individual's genome be a v1Individual vs. v2Individiual vs. v3Individual etc, wherein each genome represents discrete genomic measurements of the same individual but that yield different results. This may involve analyzing a user's snapshot data 280, if available, and analyzing the users bioinformatic data over time to identify changes in genomic information.

Genome data 210 may be obtained from suitable third-party services 130 such as direct-to-consumer genetic testing companies, from various labs 160 which performed genetic testing, or any other suitable source of genetic information.

Microbiome data 220 explores the composition of microbial communities residing in various parts of the body. The human body is home to trillions of microorganisms, including bacteria, viruses, fungi, and other microbes, collectively known as the microbiota or microbiome. These microbial communities play a crucial role in human health and wellness in several ways. The gut microbiota, located primarily in the intestines, plays a key role in digestion and nutrient absorption. It helps break down complex carbohydrates, produces vitamins (such as vitamin K and some B vitamins), and metabolizes dietary compounds that are otherwise indigestible. The microbiota plays an important role in training and modulating the immune system. It helps distinguish between harmful pathogens and harmless antigens, and it assists in the development of immune tolerance. The gut-brain axis refers to the bidirectional communication between the gut and the brain. The gut microbiota can influence this axis and has been linked to conditions such as anxiety, depression, and stress. Imbalances in the microbiota, referred to as dysbiosis, have been associated with a variety of health conditions, including inflammatory bowel diseases (such as Crohn's disease and ulcerative colitis), allergies, asthma, autoimmune diseases, and even certain cancers. The gut microbiota can affect how medications are metabolized and their effectiveness. It can also influence the side effects of certain medications. Therefore, it would be beneficial and useful to have readily available microbiome data related to a user for various purposes such as matching with and vetting potential romantic partners, purchasing and/or prescribing medications or treatments, and purchasing food (either at a restaurant or at a grocery store).

Some exemplary subcategories of microbiome data 220 include the oral microbiome 221, which are microbial flora in the oral cavity (e.g., the mouth), the gut microbiome 222 which are the microorganisms in the gastrointestinal tract. The dermal microbiome 223 which are the microbes associated with the skin. Microbiome data 220 may be obtained in several ways. One method may involve the use of a third-party service 130 such as a direct-to-consumer microbiome testing, which typically requires an individual to provide a stool sample which is then analyzed to provide information about the composition of the individual's microbiome. Similarly, a medical provider may order some tests which require an individual to provide a saliva or urine or stool (or other bio-sample) for lab 160 analysis of the individual's microbiome. In some implementations, one or more IoT devices 140 may be deployed and configured to measure and transmit data related to one or more bio-samples of an individual to cloud-based platforms 101 for processing.

Phenotype data 230 describes observable traits and characteristics influenced by both genetic and environmental factors. Phenotype data can include physical characteristics, physiological traits (e.g., blood pressure, cholesterol levels, metabolism, etc.), and behavioral traits such as personality traits, cognitive function, and disease susceptibility. Some exemplary subcategories include hair color 231, eye color 232, skin color and character 233, blood type 234, and body type 235.

Generally, phenotype data is obtained through self-observation and recording of various traits and characteristics. Some physical characteristics may be obtained from linked electronic health record data such as height, weight, body mass index (BMI), eye color, hair color, etc. In some instances, IoT 140 or other sensor data may be used to obtain phenotype data related to physiological traits e.g., blood pressure, heart rate, etc. A user may submit phenotype data about themselves via their PHDB mobile device 110a or their computer 115a. For example, a user can submit information about their daily activities, habits, and behaviors including sleep patterns, exercise routines, dietary habits, and any notable behaviors or tendencies. Additionally, or alternatively, a user may optionally choose to link third-party services or applications with their PHDB so that personal health information about the user that is captured by said services or applications may be sent to PHDB for storage. For instance, a user may integrate their dietary data from a nutritional application, stored on their PHDB mobile device, which tracks the user's meals and macro-nutrients consumption as well as other eating habits. As another example, a user may choose to allow third-party services which provide cognitive tests, personality assessments, or psychological evaluations to gather data on the user's cognitive abilities, personality traits, and mental health, and provide this information for storage in the user's PHDB. By systematically collecting and recording this information over time, the system can build a comprehensive profile of phenotype data, which can be valuable for personal health management, understanding genetic predispositions, and participating in research studies or clinical trials.

Biometric data 240 involves distinctive physical and behavioral characteristics unique to an individual. Some exemplary subcategories include, but are not limited to, fingerprints 241, face prints 242, voice prints 243, and gait data 244. Biometric data 240 may be obtained from various sources such as, for example, IoT devices 140 or sensors and/or third-party services 130. There are several biometric sensors available for obtaining biometric data. Such sensors may be embedded hardware such as embedded into a PHDB mobile device 110a (e.g., a fingerprint scanner, microphone, facial recognition system, etc.). Biometric sensors may be separate devices (e.g., stand-alone fingerprint scanner) which may be connected to (wired or wireless) a computing device such as a computer 115a or mobile device and which may obtain and transmit biometric data. Some exemplary biometric sensors which may be used to obtain biometric data 240 can include heart rate monitors, electrocardiogram sensors, blood pressure monitors, pulse oximeters, temperature sensors, electrodermal activity sensors, microphones, facial recognition systems, accelerometers and gyroscopes, and bioimpedance sensors, to name a few.

Medical data 250 encompasses a range of health-related information. The subcategories may include electronic health records (EHRs) 251, measurements 252, events 253, and trends 254. Medical data 250 may be obtained from a user's linked EHR (e.g., Provider specific, or Insurer/Payer) or connected devices (e.g., phone, watch, wearables) or a combination. Medical measurements 252 encompass a wide range of quantitative data collected during the assessment, diagnosis, and monitoring of health and disease. Some common medical measurements include vital signs (e.g., body temperature, pulse rate, blood pressure, respiratory rate, etc.) body measurements (e.g., height, weight, BMI, waist circumference, etc.), laboratory tests (e.g., complete blood count, blood chemistry tests, urinalysis, sexually transmitted infection analysis, etc.), imaging studies (e.g., x-rays, ultrasound, magnetic resonance imaging, computed tomography scan, etc.), electrocardiogram, and various biometric measurements (e.g., heart rate variability, electrodermal activity, pulse oximetry, etc.).

A medical event 253 may refer to a significant health-related incident that may require medical attention or intervention. Medical events can vary widely in nature and severity, and they can be acute or chronic. Some examples of medical events include, but are not limited to, acute illness, injury, allergic reaction, surgery, hospitalization, medical procedure, mental health crisis, cardiovascular event, and/or neurological event (e.g., seizure or transient ischemic attack).

Activity data 260 captures information related to an individual's physical and social activities. The subcategories include fitness tracking 261, location tracking 262, activity tracking 263, social network tracking 264, and sleep tracking 265. A user may optionally select which services and/or applications they wish to integrate with their PHDB. In this way, the user can manage which data is uploaded to their PHDB.

Preference data 270 reflects an individual's preferences in various aspects of life. The subcategories include dating 271, dining 272, doing 273, privacy rules 274, and schedule rules 275. Dating preferences 271 may include a desired attributes in a potential romantic partner. These desired attributes may be physiological attributes (e.g., height, weight, ethnicity, etc.), character attributes (e.g., humor, kind, intelligent, etc.), behavioral attributes (e.g., mental health), or any other type of preference an individual may have as it relates to dating. Dining preferences 272 may refer to types of food (e.g., Chinese, Italian, Mexican, Indian, Vegan, etc.), specific or general restaurants, eating habits or restrictions, price-point limits (e.g., no restaurants with $70 entrees), dining ambiance preferences, and/or the like. Doing preferences 273 may be closely related to activity data and may refer to activities the individual prefers to do or perform while on a date. For example, an individual may input (or have an AI/ML assistant input for them based on historical activities/data) that they enjoy hiking, long distance bike riding, and sailing, but they are also open to try new activities like snorkeling or paddle boarding. Privacy rules 274 may refer to guidelines which an individual can set to manage the collection, use, disclosure, and protection of their personal health information store in their PHDB. Food sensitivities like Lactose, Gluten or other allergies (e.g., nuts) may also be encoded. Privacy rules can vary depending on the jurisdiction, user, and the type of information being protected. They can include provisions for obtaining consent for the collection and use of personal information, maintaining the confidentiality of that information, and providing individuals with access to their own information. Schedule rules 275 may refer to rules set by an individual which govern the scheduling of events (e.g., prospective dates with matched individuals), activities, or resources. In general, schedule rules may comprise (but not limited to) availability rules, priority rules, constraints, and synchronization rules.

Snapshot data 280 refers to an individual's various bioinformatic information at a given point in time. In bioinformatics, a "snapshot" of data typically refers to a specific point-in-time representation of biological data, often used for analysis or storage purposes. As illustrated, snapshot data 280 may comprise genomic data snapshots 281 which may capture the genetic information of an individual (e.g., human or animal) at a specific moment. This can include DNA sequences, variations (SNPs), and structural variants. Transcriptonomic data snapshot 282 may represent the gene expression levels in a cell or tissue at a specific time. This can include RNA sequencing data, which provides information about which genes are active and at what levels. Epigenomic data snapshots 283 may capture the epigenetic modifications (e.g., DNA methylation, histone modifications) in a cell or tissue at a specific time. This can provide insights into gene regulation and cell differentiation. Additional exemplary snapshot data can include, but is not limited to, proteomic data snapshots which capture the proteins present in a cell or tissue at a specific time and can include data on protein abundance, modifications, and interactions; metabolomic data snapshots which represent the small molecule metabolites present in a cell or tissue at a specific time and can provide insights into metabolic pathways and cellular processes; phylogenetic data snapshots which may represent the evolutionary relationships between different species or populations at a specific time and can include phylogenetic trees based on genetic or genomic data; and structural biology data snapshots which capture the three-dimensional structures of biological molecules (e.g., proteins, nucleic acids) at a specific time and can include data from X-ray crystallography, NMR spectroscopy, or cryo-electron microscopy.

This exemplary arrangement of PHDB content categories establishes a robust foundation for comprehensive health and preference profiling. This structure allows for effective management, analysis, and utilization of diverse data types to enhance personalized insights and applications within the described system.

According to some aspects, a PHDB or a subset of the data stored therein may be configured as a graph database. Such a graph database may be leveraged for various analytic, predictive, and/or scoring processes described herein. According to some aspects, platform 120 implements contact tracing and health notification with a focus on decentralized tracing and anonymity options. For example, the system may use a graph database to store and analyze the plurality of data collected by platform 120. Graph databases are well-suited for modeling complex relationships, making them ideal for contact tracing, where connections between individuals are important. Platform 120 may utilize one or more algorithms configured for contact tracing based on the collected data. For example, the algorithm could consider proximity between individuals, duration of contact, and other relevant factors to determine potential exposure to diseases. The system may be configured to send health notifications to individuals who may have been exposed to a disease. This can include information about testing, quarantine guidelines, and other relevant instructions. According to an aspect, the platform allows for decentralized tracing, meaning that individuals have control over their data and can choose whether to share it for contact tracing purposes. This may be accomplished by providing options for individuals to remain anonymous while still participating in contact tracing. This can be achieved through pseudonymization or other privacy-preserving techniques. Furthermore, platform contact tracing can integrate with healthcare providers to ensure that individuals receive appropriate care and follow-up based on their exposure status.

According to some embodiments, PHDB may further comprise Transposon data. Transposon, referred to as "jumping genes" are DNA segments that can move within the genosome to influence gene expression including transcription (synthesis of RNA from DNA) and translation (synthesis of proteins from RNA). Transposon placement can modify a gene's expression pattern via mechanisms such as providing for or disruption regulatory sequences like enhancers (which increase gene transcription) or silencers which decrease transcription. They can also rearrange genomic structure to create new gene combinations or duplicate existing genes as part of evolutionary processes.

They can also insert themselves into a gene, which may be problematic and linked to disease but may also provide evolutionary benefits via novel gene functions or expression patterns.

According to some embodiments, PHDB may further comprise spatial omics data. The PHDB can store a 3-dimensional (3d) mesh (plus time which makes its 4-dimensional) of the body with different resolution levels (i.e., mesh shapes and densities) to support analytics and simulation modeling. Where available, platform may tag multi-omics data to any given "cell" in the 3d mesh. For example, both digital and physical samples (and associated extracted information) can be spatially and temporally located to the body to provide a spatially resolved view of the biological molecules with a tissue or organism. Examples of spatial omics data can include but is not limited to, spatial transcriptomics, spatial proteomics, spatial metabolomics, spatial genomics, and spatial multi-omics (e.g., refers to the integration of multiple omics data types such as transcriptomics, proteomics, metabolomics, etc.) with spatial information. According to an embodiment, a user may select spatiotemporal restrictions on what part of the electronic medical record (e.g., which mesh or subset of a mesh) can be viewed by a given party.

A particular function of platform 120 and PHDB is the capability to analyze genome and gene expression over time and in different places in the body. To assess genome and gene expression over time, the platform may utilize one or more techniques. A first technique may involve conducting longitudinal studies to track changes in the genome over time. This can involve sequencing DNA samples from the same individual at multiple time points to identify genetic variations, including those caused by transposon movement. Another technique may use spatial transcriptomics techniques to analyze gene expression patterns in specific regions or tissues of the body. This can provide insights into how gene expression varies spatially and how it changes over time. A transposon analysis technique may be used to study the movement and impact of transposons on gene expression over time and in different tissues. This can involve identifying transposon insertion sites and their effects on nearby genes. This may also involve the use of evolutionary analysis to study how transposon movement has contributed to genetic diversity and the evolution of new gene functions. This can involve comparing transposon sequences across different species or populations. Stored 3d and 4d mesh information may be analyzed to analyze genome and gene expression over time.

According to an embodiment, the platform may allow for multiple simulation paths based on "seeds" extracted from data stored in PHDB. Because there is uncertainty with respect to sampling, the system can engage in express parametric studies (e.g., initial seed manipulation) to look at potential impacts of various factors/constraints such as imaging, sampling, extraction, errors and uncertainty for statistical, ML/AI, or modelling simulation processes (e.g., diagnostics, treatment advisory, treatment calibration, etc.).

According to an embodiment, the platform may leverage ML/AI processes that classify individual cells and/or identify cellular neighborhoods. The results of such processes may be used to create an enhanced 3d (or 4d) mesh for anchoring all data available to analysis functions. This is useful because finite element analysis, fluid modeling, fluid structure interaction modeling and broader biological simulation models are strongly intertwined with the selection and determination of such boundaries. It should be noted that such meshes can shift over time. According to an aspect, a stabilized space-time process can enable more accurate and advanced modeling simulation and ML/AI basis as a reference "atlas" for single cell, cell groups (i.e., tissue/cellular neighborhoods), and other multi-omics information as well as observations, medical data, fitness data, telemetry, imagery, etc. This may involve simulating from an average mesh that is viewed as a stable point, then minimizing the dynamism inside the mesh over a finite time. This is useful because it moves medical records data into the equivalent of a (optionally) stabilized space time mesh projection (think of it like a GPS system for the body) to provide spatiotemporal locality of data. The system may be configured to support single cell/tissue, multiple tissue groups, or whole-body simulations and can parallelize parametric studies of different "assumptions" and perturbations of said models.

Figure 3:
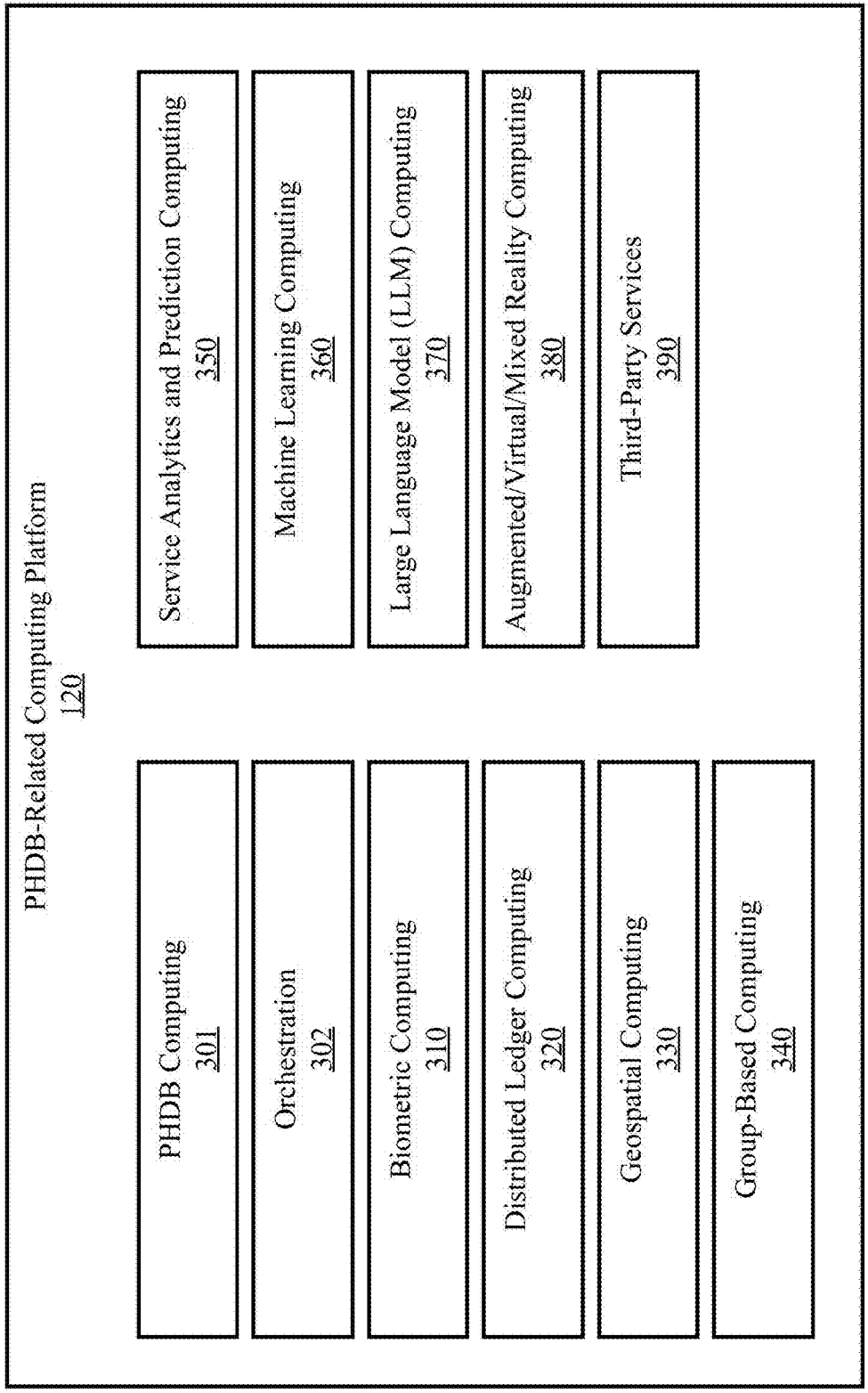
FIG. 3 is a system diagram showing an exemplary arrangement of cloud-based PHDB-related computing, according to an aspect of the invention.

FIG. 3 is a system diagram showing an exemplary arrangement of a cloud-based PHDB-related computing platform, according to an aspect of the invention. According to the aspect, the PHDB computing platform 120 may be implemented as a computing system comprising one or more hardware processors configured for providing the various functionality described herein. According to another aspect, the PHDB computing platform 120 may be implemented as non-transitory, computer-readable storage media having computer-executable instructions embodied thereon and executed by one or more hardware processors configured for providing the various functionality described herein. According to another aspect, the PHDB computing platform 120 may be a computer-implemented method executed by the platform.

According to the embodiment, PHDB-related computing platform 120 comprises various computing components configured to provide computing functionality directed to various categories to support the discrete filtering of two or more human genomes for compatibility using personal health databases. These exemplary computing components may be implemented as servers or services which provide on-demand computing when queried by a system or process. For example, a PHDB-enabled mobile computing device may query geospatial computing 330 to locate and map other PHDB users in the location of mobile device user, and responsive to the query, geospatial computing 330 can send the identified and mapped locations of the other users to the mobile device for display in an application.

PHDB computing 301 is specialized in managing and processing PHDB data, ensuring efficient access and retrieval of diverse health and preference information. Orchestration 302 is responsible for coordinating and managing the flow of data and processes within the system, ensuring seamless interactions between different computing components.

Biometric computing 310 focuses on the analysis and interpretation of biometric data, including fingerprints, face prints, voice prints, and gait data.

Distributed Ledger Computing 320 utilizes distributed ledger technology for secure and transparent record-keeping of sensitive health and preference data, ensuring data integrity and privacy.

Geospatial computing 330 offers ready-to-use demographic datasets and map/imagery layers that allow users to gain immediate context to applications of all types. Group-based computing 340 offers the use of collaboration tools and software that enable multiple users to work together on shared tasks. Service analytics and prediction computing 350 involves leveraging data analytics and predictive modeling techniques to enhance the delivery and optimization of services. Machine learning computing 360 refers to the use of computing systems and algorithms to enable machines to learn and make predictions or decisions based on data.

Large Language Model (LLM) computing 370 refers to the utilization of advanced computational systems to train, deploy, and utilize large language models. These models are typically built using deep learning techniques and have the capability to understand, generate, and process human language at a sophisticated level.

Augmented/Virtual/Mixed Reality computing 380 involves integrating digital information, such as graphics, audio, and other sensory environments, with the user's real-world environment in real-time. Enhances the user's perception of the physical world by overlaying computer-generated content onto it.

Third-Party Services 390 engages external entities to provide additional services, expanding the functionality and capabilities of the PHDB-related computing platform.

Figure 4:
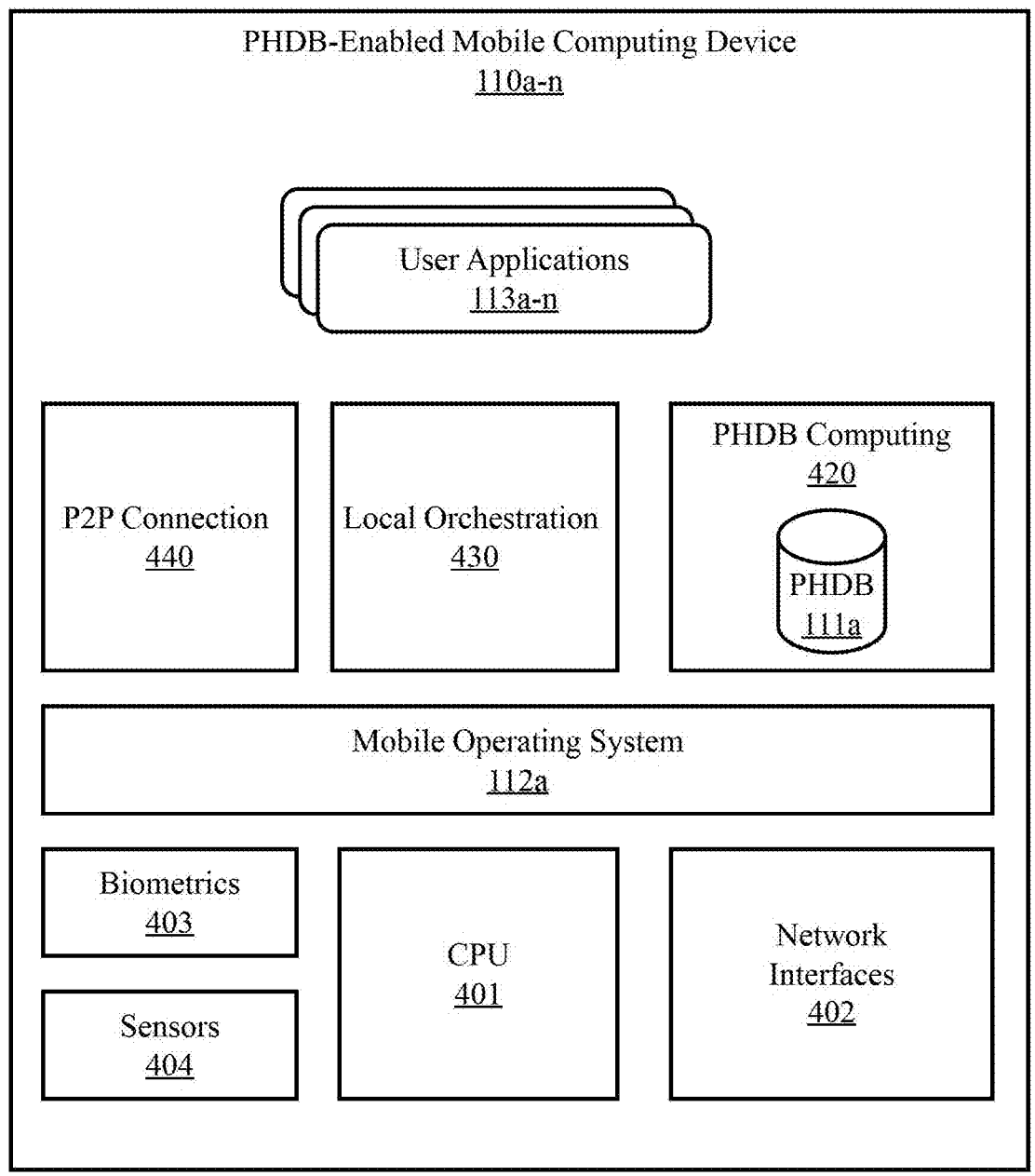
FIG. 4 is a system diagram showing an exemplary arrangement of mobile device-resident PHDB-related computing, according to an aspect of the invention.

FIG. 4 is a system diagram showing an exemplary arrangement of mobile device configured to support PHDB-related computing, according to an aspect of the invention. The PHDB-enabled mobile computing device 110a-n comprises several key components such as various User Applications 113a-n which are Applications on the mobile device that interface with the PHDB. P2P Connection 440 which establishes a peer-to-peer (P2P) connection facilitating direct communication between PHDB-enabled mobile devices. Local orchestration 430 which manages and coordinates local processes and data flow within the mobile device. PHDB computing 420 which is responsible for securely storing PHDB 111a and is specialized in managing and processing PHDB data, ensuring efficient access and retrieval of diverse health and preference information. PHDB computing 420 may also be configured to perform edge-based computing, in certain embodiments. The PHDB-enabled mobile device 110a-n includes a central processing unit (CPU) 401 for processing, network interfaces 402 for connectivity with various networks (i.e., the Internet, a cellular network), a plurality of sensors 404 for data input, biometrics detection 403 (e.g., fingerprint scanner, microphone, etc.) and a mobile operating system 112a.

The PHDB mobile computing device 420 may be implemented as a smart phone, tablet, or smart wearable device. The PHDB computing device 420 securely stores PHDB 111a. The mobile device, denoted as PHDB-enabled mobile device 110a-n, is capable of sending requests for PHDB-based services to the cloud 101 and receiving requests for PHDB-related access from cloud-services.

The PHDB-enabled mobile device 110a-n establishes a P2P connection 440, enabling secure peer-to-peer PHDB operations. This ensures direct and secure communication between mobile devices for PHDB-related functionalities. For example, if prospective romantic partners have been identified in an area, say a music venue, then identified and matched potential partners may discover and communicate with each other via a P2P connection established between their respective PHDB enabled mobile device 110a.

This configuration enhances the PHDB-enabled mobile device's 110a-n capabilities by enabling local storage and processing of PHDB data, reducing reliance on external cloud services while maintaining secure P2P communication for PHDB operations.

Figure 5:
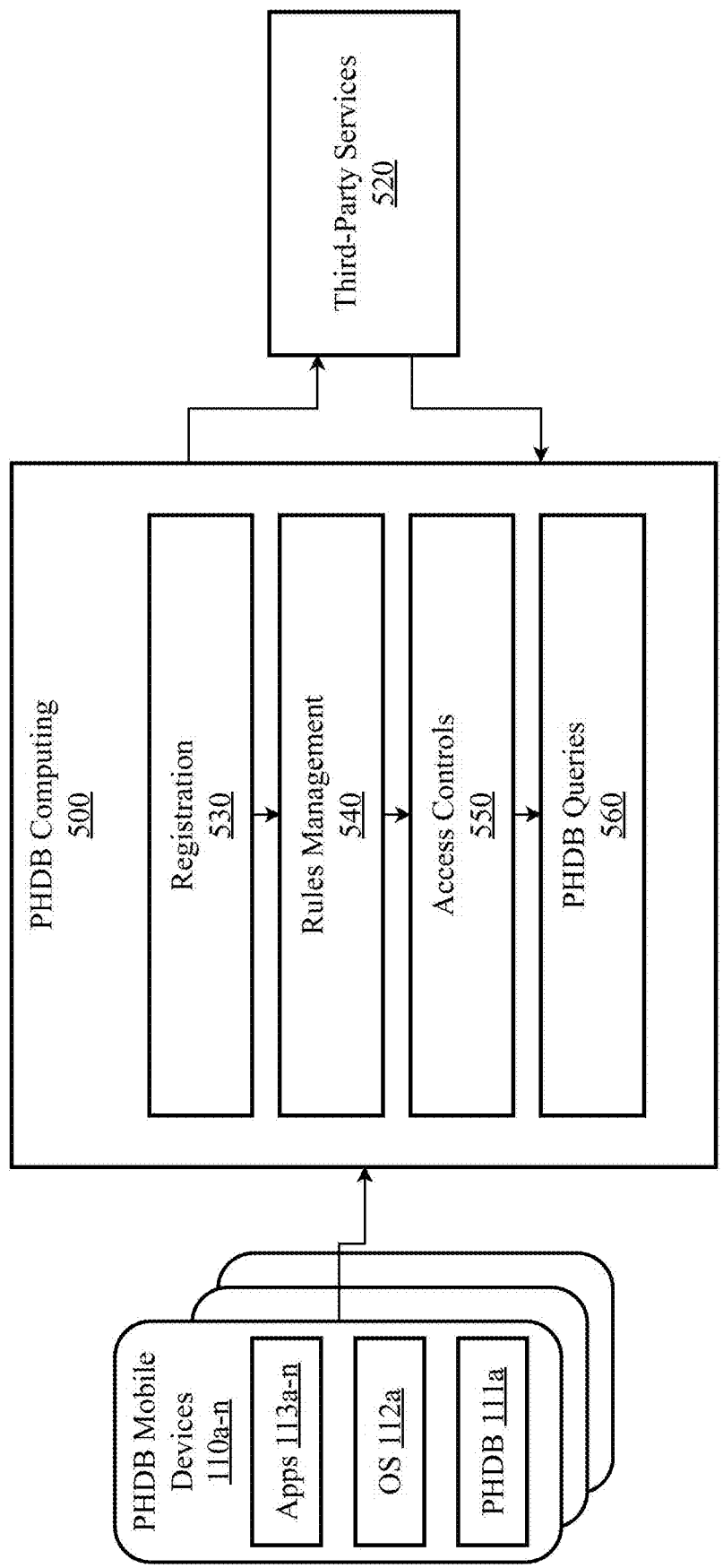
FIG. 5 is a system diagram showing an exemplary arrangement of a PHDB computing server or service with registration controls and third-party service integration, according to an aspect of the invention.

FIG. 5 is a system diagram showing an exemplary arrangement of a PHDB computing server or service with registration controls and third-party service 520 integration, according to an aspect of the invention. The components of PHDB computing 500 initiate a process that commences at the PHDB mobile device 110a-n, encompassing apps 113a-n, an OS 112a, and PHDB 111a. The process then progresses through the stages of PHDB computing 500 which acts as an intermediary in the process flow, facilitating seamless interactions between the PHDB mobile device 110a-n and various third-party services 520. For example, a user of PHDB mobile device 110a may grant permission for social media data related to their likes, check-ins, and subscribed pages data to be uploaded to their PHDB. In this example, PHDB computing 500 may query a social media server to retrieve the social media data, process the retrieved social media data (e.g., encrypt, transform, format, etc.), and then send the processed data to the PHDB mobile device 110a for storage in PHDB 111a.

Registration 530 initiates the registration process for PHDB services to users, ensuring proper onboarding and authentication. Registration may store login credentials of a user for various third-party services 520 to facilitate data exchange. Rules management 540 manages and enforces rules governing the access and usage of PHDB services, contributing to secure and compliant operations. Rules management 540 may be aware of or acquire user-defined access rules for their PHDB and apply those rules to adhere to the user's set permissions regarding access to their personal health information. Access Controls 550 implements controls (e.g., based on user defined rules, or governing rules and regulations such as HIPPA) to regulate access to PHDB services, safeguarding sensitive data and ensuring that users adhere to established rules. PHDB Queries 560 facilitates queries and requests related to the PHDB, enabling users to retrieve specific information or perform actions within the PHDB ecosystem.

In some implementations, personal health information within the PHDB may be shared with the third-party services 520. This integration ensures that the PHDB ecosystem can seamlessly interact with and contribute to third-party services.

This exemplary arrangement offers a comprehensive system for managing PHDB services, from user registration 530, to access controls 550, and facilitates the sharing of genomic data with external third-party services 520, thereby expanding the functionality and reach of the PHDB ecosystem.

Figure 6:
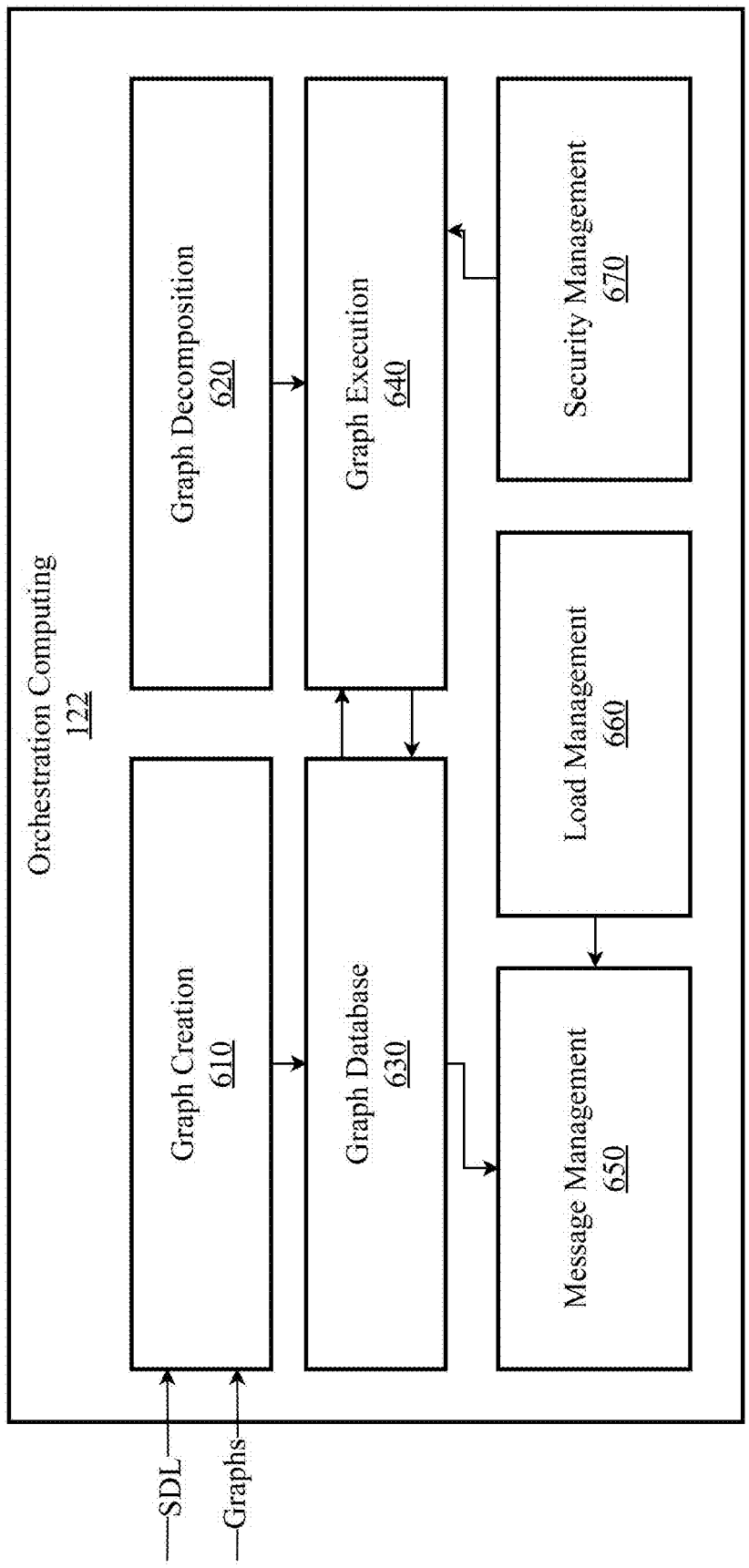
FIG. 6 is a system diagram showing an exemplary arrangement of a PHDB orchestration service according to an aspect of the invention.

FIG. 6 is a system diagram showing an exemplary arrangement of a PHDB orchestration service according to an aspect of the invention. The orchestration computing 122 initiates a process that involves graph creation 610 which occurs when a user requests a service, the orchestration service receives the service description and creates a service graph. As shown, graph creation 610 may receive as input service description language (SDL) data. It is a language used to describe the services, their dependencies, and the workflow of a distributed system. SDL is used to create a formal description of the services and their interactions, which can then be used by orchestration computing 122 to automate the deployment, scaling, and management of the services. Additionally, or alternatively, graph creation 610 may receive as input a graph to be executed by orchestration computing 122.

The graph creation process results in the establishment of a graph database 630 wherein created graphs may be stored and retrieved for use. For example, a graph may represent various services that need to act on some data to perform the requested process. Graphs are often used in orchestration computing to represent the relationships between different components or tasks in a system. These graphs, known as orchestration graphs or workflow graphs, can help visualize the dependencies between tasks and the flow of data or control through the system.

Graphs can represent the workflow or sequence of tasks that need to be executed to complete a job or process. Each node in the graph represents a task, and the edges represent the dependencies between tasks. Graph decomposition 620 is a process where the created graph undergoes decomposition, breaking it down into subgraphs. This step is integral to optimizing service delivery and resource utilization. For example, each subgraph may represent a single service and the data processing required thereof. Graph execution 640 occurs when the decomposed graph is executed, leading to the activation of subgraphs. This stage ensures that the intended service actions are carried out effectively. The graph database 630 stores and manages the created graph, serving as a repository for orchestrating service delivery. Message management 650 is the process where messages are exchanged between subsystems to orchestrate the delivery of messages. Message may comprise data that is to be operated on or can include instructions for processing. During graph execution, security management 670 ensures the integrity and confidentiality of the controls and graph. This includes implementing measures to protect against unauthorized access or manipulation of genomic data. Load management 660 oversees the distribution of workloads during graph execution, optimizing system performance and resource allocation. This can involve deploying, scaling, and managing complex applications or services across a distributed environment. Graphs can be used to allocate resources dynamically based on the requirements of different tasks or components. For example, a graph can help determine where to deploy a new instance of a service based on current resource availability and workload.

This orchestration service provides a systematic and efficient approach to coordinating the delivery of services within the PHDB ecosystem. By decomposing and executing service graphs, managing messages, ensuring security, and optimizing load distribution, orchestration computing service 122 enhances the overall efficiency and reliability of service delivery.

Figure 7:
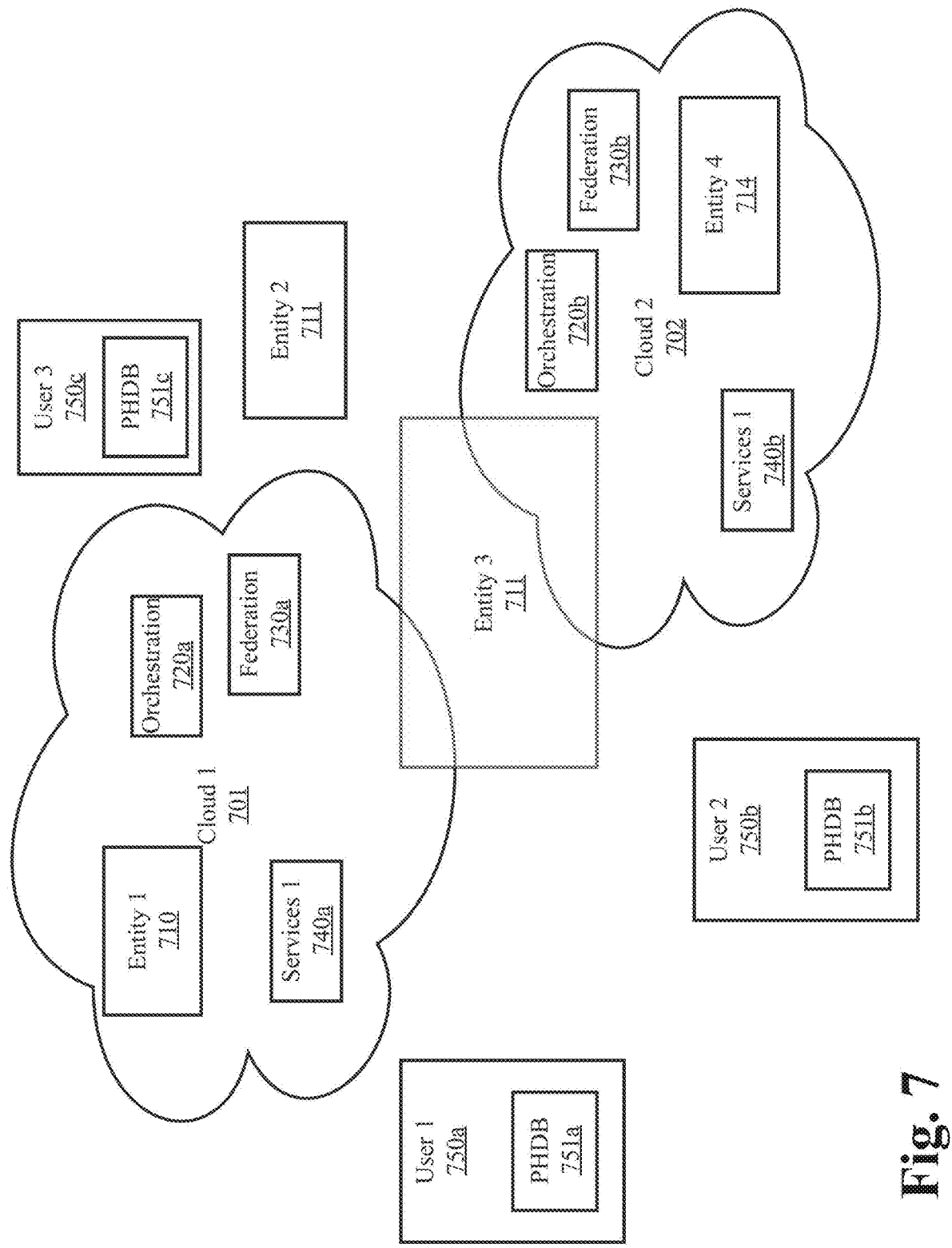
FIG. 7 is a system diagram showing an exemplary arrangement of a federated PHDB architecture, according to an aspect of the invention.

FIG. 7 is a system diagram showing an exemplary arrangement of a federated PHDB architecture, according to an aspect of the invention. A federated cloud architecture is a form of computing where multiple cloud computing environments are connected and integrated to work together as a unified, distributed system. In this federated cloud model, various cloud service providers (CSPs) 701, 702 collaborate, establishing a seamless and interoperable infrastructure for users. Federated cloud computing enables interoperability between different cloud providers or regions, allowing users to seamlessly access and use resources across multiple platforms.

According to the embodiment, each CSP may comprise entity 710, 714, an orchestration component 720a-b, a federation component 730a-b, and various services 740a-b. Orchestration components provide functionality directed to the execution of various tasks using one or more services provided by the CSP or other services provided by a different CSP. A CSP may comprise a group (e.g., federation 730a-b) or a collection of autonomous entities (such as organizations, departments, or systems) that cooperate and collaborate to achieve a common goal. Each entity in the federation retains control over its own resources and operations, while participating in a large, coordinated system. For example, According to the embodiment, CSPs may have entities that operate fully within the CSP such as entity 1 710 of CSP 701. There are also entities that can exist between and among various CSPs such as entity 3 712 which operates within both cloud-based service providers. Also, there may be entities that exist outside of a CSP such as entity 2 711 which may interact with cloud 1 701 and cloud 2 702. Furthermore, the federated architecture further comprises a plurality of users 750a-c which are operating a PHDB enabled mobile device with a PHDB 751a-c stored on the user's mobile device.

Figure 8:
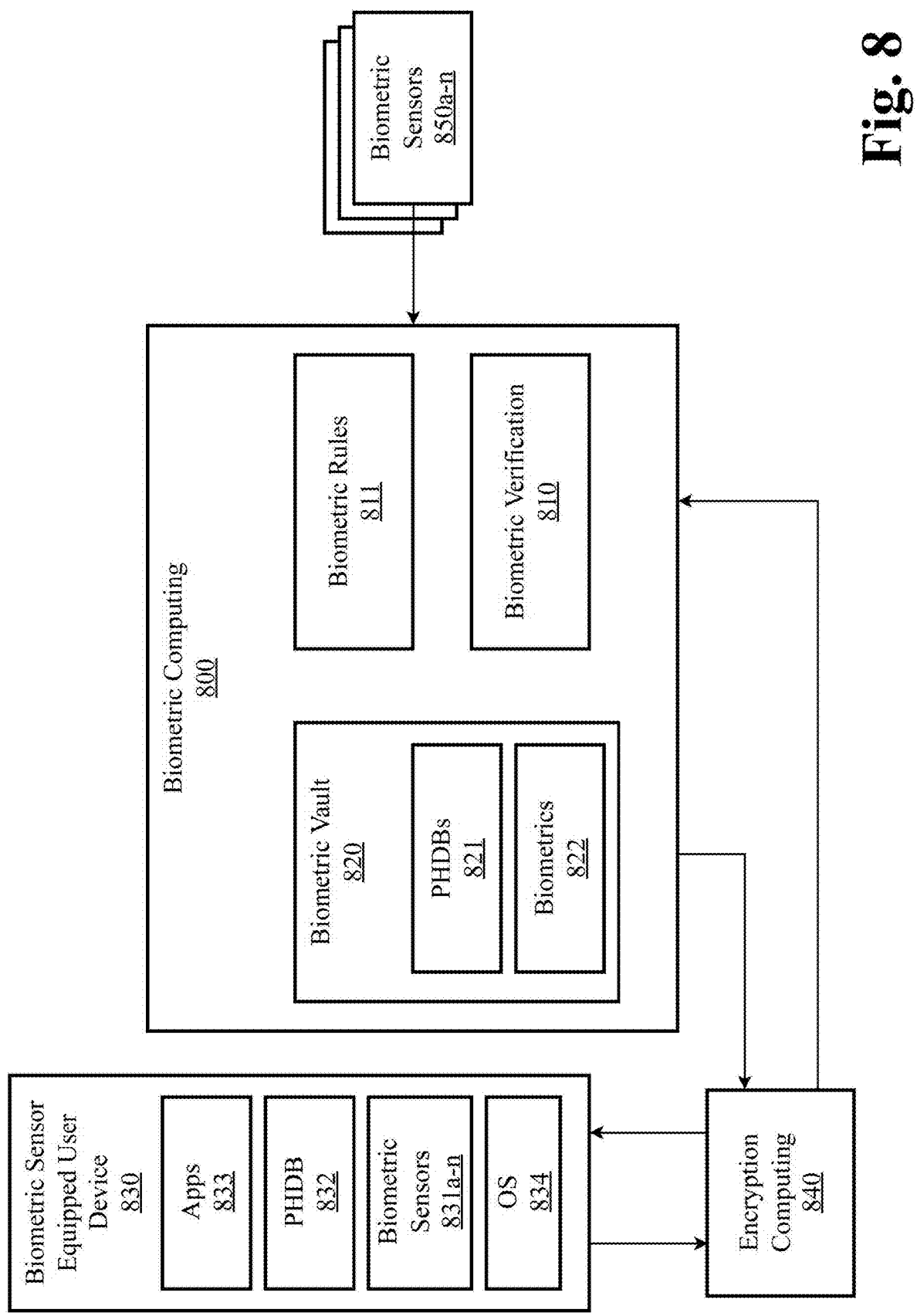
FIG. 8 is a system diagram showing an exemplary arrangement of biometric computing used for biometric sensors located on a user's endpoint device or with separate biometric sensor devices, according to an aspect of the invention.

FIG. 8 illustrates a system diagram showcasing an exemplary configuration of biometric computing utilized for biometric sensors situated either on a user's endpoint device or on separate biometric sensor devices. Biometric computing 800 entails the utilization of biometric technology within computing systems. This technology involves the measurement and statistical analysis of distinctive physical and behavioral characteristics of individuals. A plurality of biometric sensors 850a-n collect the biometric data, which is subsequently computed, encrypted 840, and then shared with the biometric sensor equipped user device 830. The Biometric Sensor Equipped User Device 830 denotes a device incorporating biometric sensors 831a-n designed to capture and analyze physical or behavioral traits for functions such as fingerprint scanning, facial recognition, iris scanning, voice recognition, heart rate monitoring, and gesture recognition. Additionally, the biometric sensor equipped user device 830 includes applications (apps) 833, PHDB 832, and the operating system 834.

The data obtained from the biometric sensor equipped user device 830 is shared with encryption computing 840, which encrypts the obtained data to thwart unauthorized access. Encryption schemes such as AES or homomorphic encryption may be implemented to protect the obtained biometric data. Subsequently, the obtained data is sent to a biometric vault 820. The biometric vault securely stores biometric authentication methods for access control. The vault may store an instance of PHDB 821 which may only comprise encrypted biometric data such as biometric templates 822. It encompasses biometric rules 811 denoting privacy policies, guidelines, or principles pertaining to biometric technology use, and biometric verification 810, a process confirming identity by comparing unique physiological or behavioral characteristics against stored templates. The biometric vault 820 additionally includes the PHDBs 821 and biometrics 822. In addition to biometric sensors in the equipped user device 830, external biometric sensors 850a-n may be configured to capture and transmit biometric data to biometric computing 800. Biometric sensor data may be encrypted 840 and shared with the biometric sensor equipped user device 830 for storage in PHDB 832.

In an embodiment, biometric computing 800 may be used to provide biometric authentication of PHDB mobile device users. Biometric data gathered by user device 830 or biometric sensors 850a-n may be sent to biometric computing 800 where it may be processed and compared against stored biometrics 822 to authenticate a PHDB mobile device user. For example, if a user wishes to set new access permissions for third-party applications to access their PHDB, the system may prompt the user to provide biometric authentication to ensure that the user is the one managing access to their personal health information.

Figure 9:
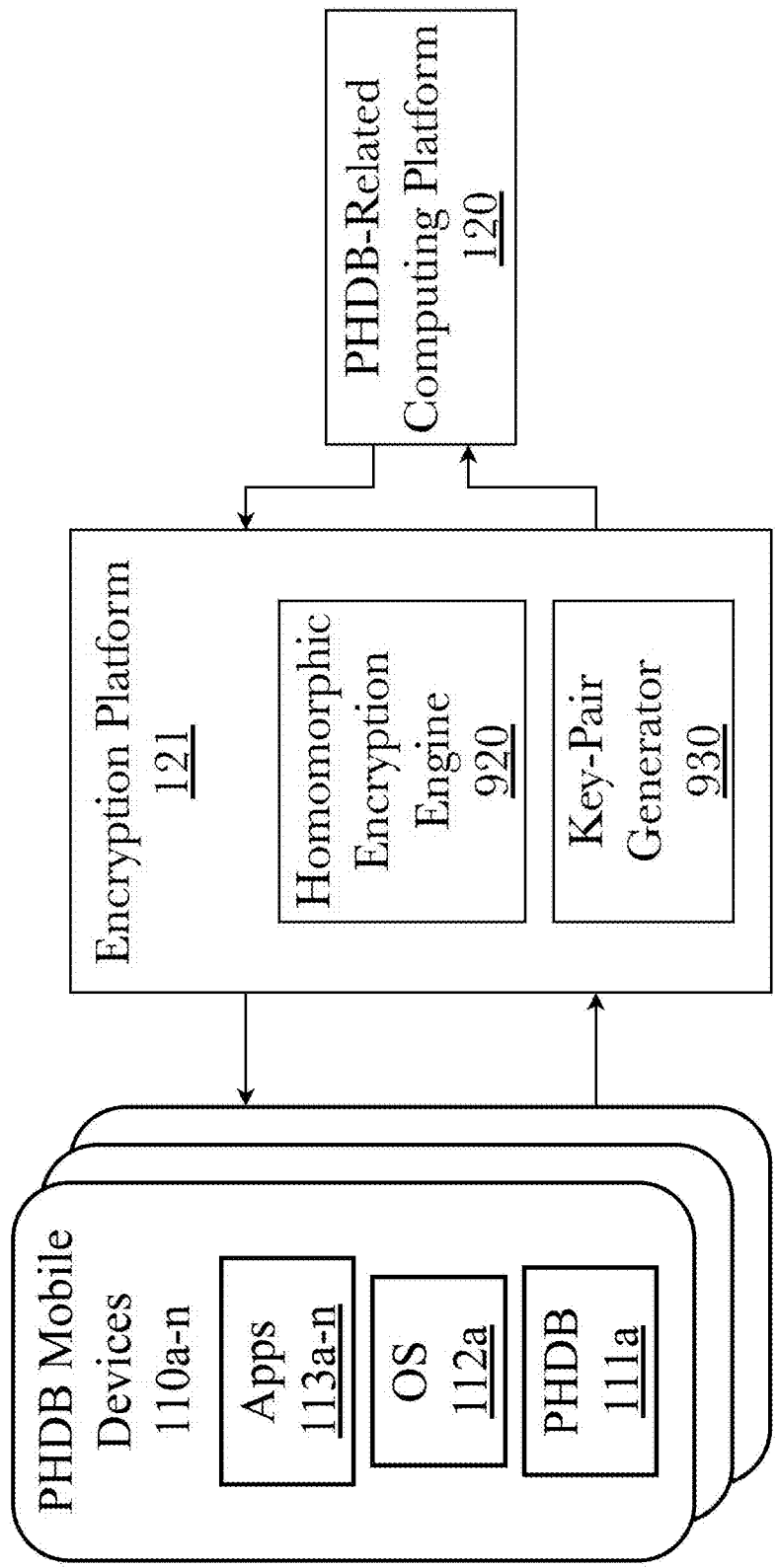
FIG. 9 is a system diagram showing an exemplary arrangement of an encryption platform for PHDB computing, according to an aspect of the invention.

FIG. 9 is a system diagram showing an exemplary arrangement of an encryption platform for PHDB computing, according to an aspect of the invention. The PHDB-related computing platform 120 platform facilitates the sharing of personal health information (e.g., genomic data) with the encryption platform 121. Encryption platform possesses the capability to perform both regular and homomorphic encryption. The encrypted data is then securely transmitted to the requester on the PHDB mobile devices 110*a-n*, which consist of applications (apps) 113*a-n*, an operating system (OS) 112*a*, and PHDB 111*a*.

Homomorphic encryption engine (HEE) 920 functions as a cryptographic system providing homomorphic encryption of personal health information or other data requested from PHDB cloud services 101. The use of homomorphic encryption engine enables computations that can be executed on encrypted data without requiring decryption. In contrast to regular encryption, which necessitates decryption before operations, homomorphic encryption allows computations directly on encrypted data, safeguarding its confidentiality. The homomorphic encryption engine 920 employs robust encryption algorithms to encrypt data. The encrypted data retains a format that enables specific computations without revealing the original information. In an implementation, HEE 920 may use partially homomorphic encryption, which is a type of homomorphic encryption that allows for computations on either the ciphertext or the plaintext, but not both. Examples include the RSA encryption method and the ElGamal method. In an implementation, HEE 920 may use a fully homomorphic encryption, which allows for arbitrary computations to be performed on encrypted data, including both additions and multiplications. Examples of fully homomorphic encryption include the Gentry-Halevi-Smart (GHS) scheme and the Brakerski-Gentry-Vaikuntanathan (BGV) scheme.

The key pair generator 930 component generates a public-private key pair crucial for the asymmetric encryption process. The public key is openly shared and is employed for encrypting data. The private key is kept confidential and is used for decrypting data and certain operations. Some common asymmetric encryption algorithms that may be implemented can include RSA, ECC, and Diffie-Hellman key exchange. The integration of key pair generation with homomorphic encryption enhances the platform's capabilities for privacy-preserving data analytics, secure cloud computing, and collaborative processing of confidential information.

In some embodiments, key pair generator 930 may utilize symmetric encryption techniques. In symmetric encryption, the same key is used for both encryption and decryption. This means that both the sender and the receiver need to know the same key. Symmetric encryption is typically faster and more efficient than asymmetric encryption, but it requires a secure way to share the key between the sender and receiver. Common symmetric encryption algorithms that may be implemented can include, but are not limited to, AES, data encryption standard (DES), and triple DES.

This system ensures that sensitive personal health data (e.g., genomic data) can be securely processed and analyzed while maintaining the privacy of the information through the utilization of both regular and homomorphic encryption techniques.

Figure 10:
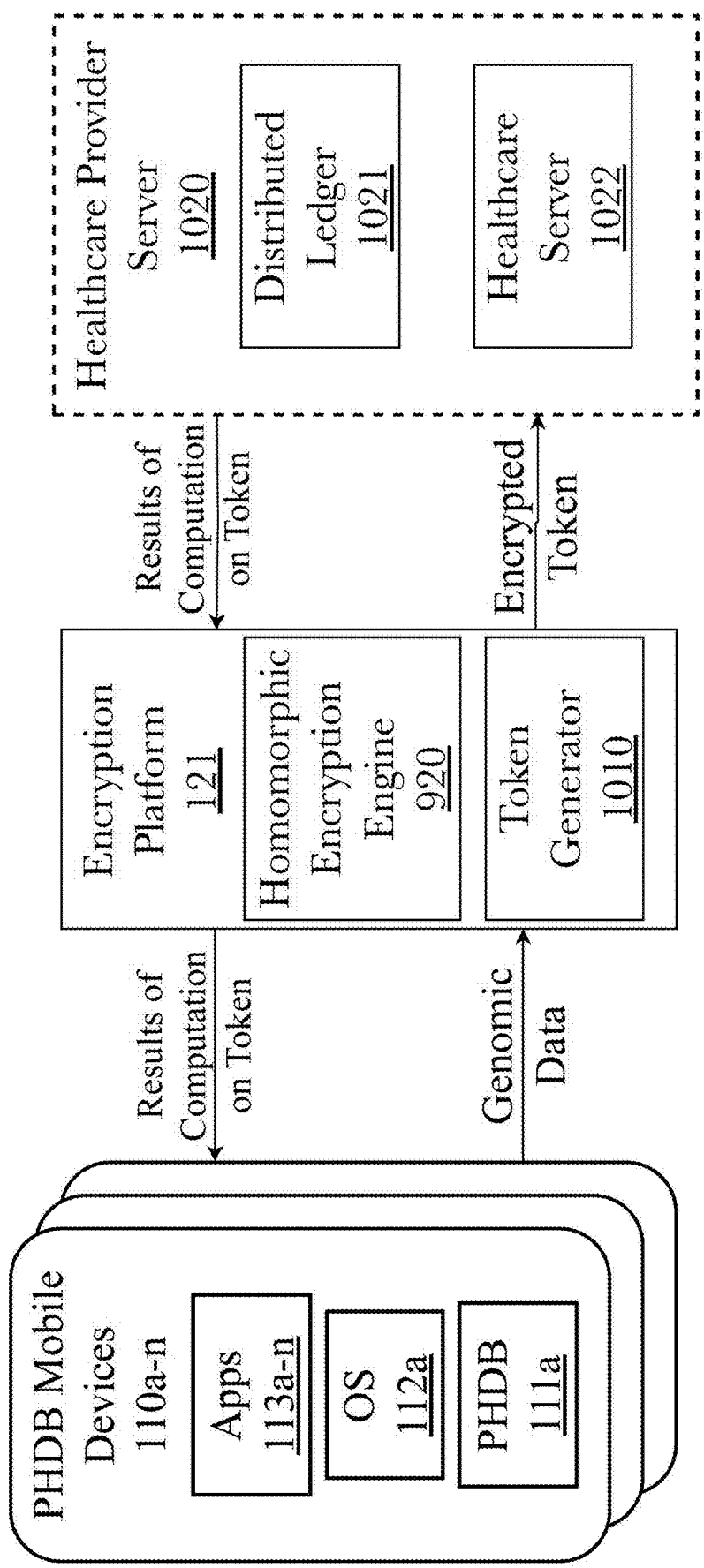
FIG. 10 is a system diagram showing an exemplary arrangement of a PHDB computing system using distributed ledger technologies, according to an aspect of the invention.

FIG. 10 is a system diagram showing an exemplary arrangement of a PHDB computing system using distributed ledger technologies, according to an aspect of the invention. The PHDB mobile devices 110*a-n* serves as the initiator by sharing genomic data through an encryption platform. The encryption platform 121 encompasses a homomorphic encryption engine 920 and a token generator 1010 powered by blockchain technology, enhancing traceability. The homomorphic encryption engine 920 facilitates secure computations on encrypted data without requiring decryption, preserving data confidentiality. The token generator 1010 employs blockchain technology to generate encrypted tokens, ensuring the traceability and secure data transfer. The encrypted token is then shared with the healthcare provider server 1020, comprising a healthcare server 1022 and a distributed ledger 1020. The healthcare server 1020 manages and processes the token encryption of data received from the encryption platform and the distributed ledger 1022 utilizes blockchain technology to maintain an immutable record of transactions and ensure transparency in data handling. The healthcare provider 1020 may process the encrypted genomic data or otherwise perform some computation on the genomic data. Examples of the types of processing that may be performed on genomic data by healthcare server 1022 can include, but are not limited to, whole genome sequencing, whole exome sequencing, genetic testing for specific conditions, pharmacogenomic testing, carrier screening, genomic tumor profiling, and general genomic counseling. Healthcare server 1022 can perform these types of computations and store the results on distributed ledger 1021. The results of the computations may be stored on a blockchain token.

Encryption platform 121 receives the tokenized computation results and can transmit them back to the requester on the PHDB Mobile devices 110*a-n*, completing the secure and traceable data exchange.

This system integrates homomorphic encryption, blockchain-powered token generation, and distribution ledger technologies to ensure secure, private, and transparent transactions in the context of personal health data (PHI) exchange. The use of encrypted tokens and distributed ledgers enhances traceability and accountability in the handling of sensitive genomic information.

Figure 11:
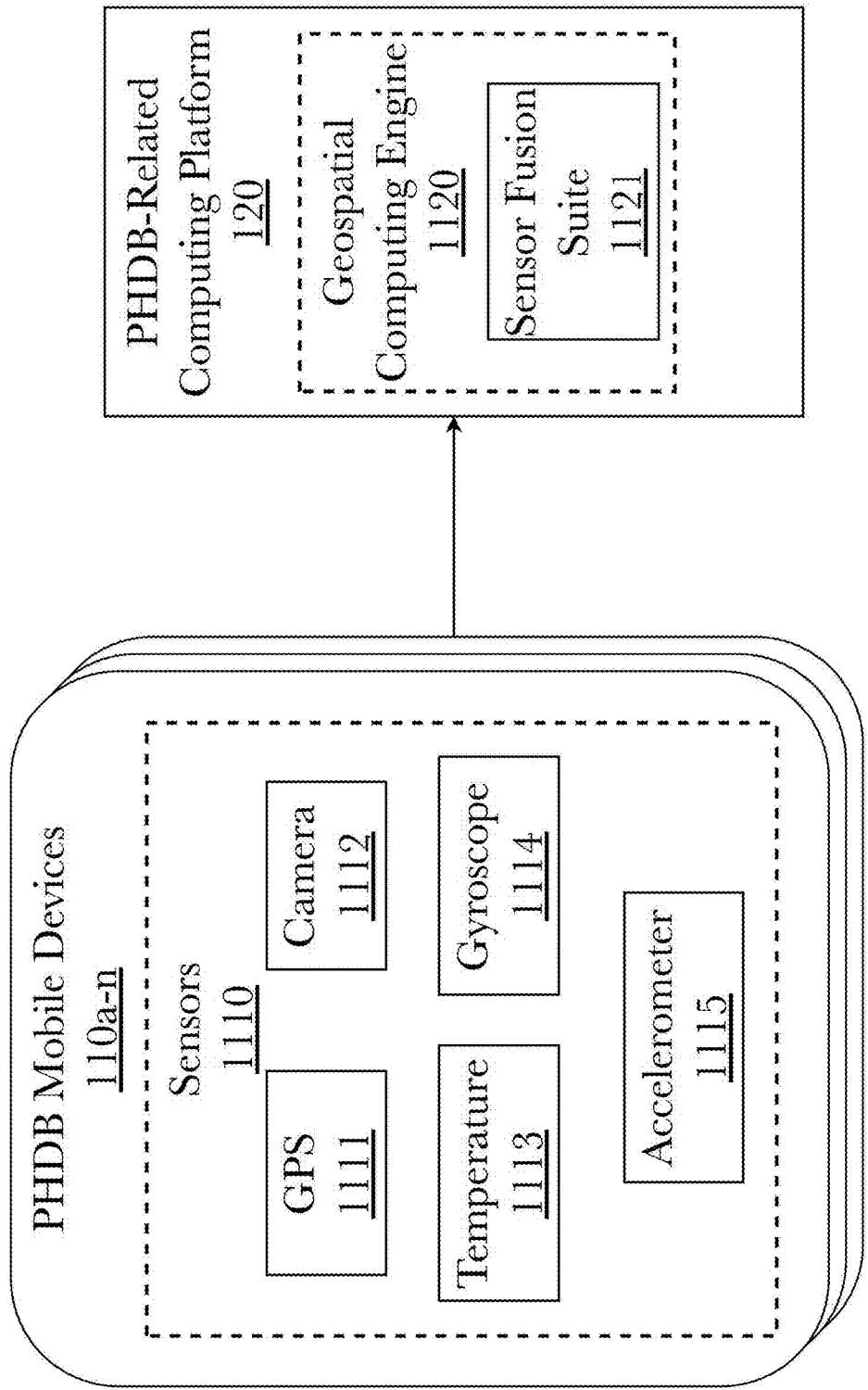
FIG. 11 is a system diagram showing an exemplary arrangement of a PHDB computing system using geospatial computing, according to an aspect of the invention.

FIG. 11 is a system diagram showing an exemplary arrangement of a PHDB computing system using geospatial computing, according to an aspect of the invention. The PHDB mobile devices 110*a-n* is equipped with a set of sensors 1110, including, but not limited to, GPS 1111, Camera 1112, Temperature 1113, Gyroscope 1114, and Accelerometer 1115. The PHDB mobile devices share sensor data with the PHDB-related computing platform 120. Existing within the PHDB-related computing platform, the geospatial computing engine 1120 is responsible for processing geospatial data and leveraging a sensor fusion suite 1121. The geospatial computing engine 1120 receives position (e.g., location) updates from users, receives environmental events and obtains or generates local environmental data.

The geospatial computing engine 1120 utilizes a sensor fusion suite 1121 to integrate and analyze data from various sensors, including GPS 1111, Camera 1112, Temperature 1113, Gyroscope 1114, and Accelerometer 1115. According to an embodiment, sensor fusion suite 1121 may be implemented as a collection of algorithms and technologies used to integrate data from multiple sensors to provide a more accurate and comprehensive understanding of a system, user, or environment. Common sensor fusion algorithms include Kalman filters, particle filters, and Bayesian inference technique. Sensor fusion is particularly important in applications where multiple sensors are used to gather information about the same phenomenon such as when collecting information about a user's current environment. For example, a user's GPS coordinates may indicate that they are at a restaurant, but GPS cannot indicate if the user is dining inside or is seated outside on a balcony. Sensor fusion suite 1121 may be able to use ambient temperature sensor readings collected from the user's mobile device 110*a* to determine that the user is dining outside. As a result, the PHDB system may identify potential romantic partners who are also dining outside or that may be passing by on the street nearby the restaurant.

This system enables the integration of geospatial computing into the PHDB computing environment, leveraging sensor data from PHDB mobile devices equipped with GPS 1111, Camera 1112, Temperature 1113, and Gyroscope 1114. The Geospatial Computing Engine 1120, with its sensor fusion suite 1121, processes and analyzes the data to enhance the capabilities of the PHDB computing system 120.

Figure 12:
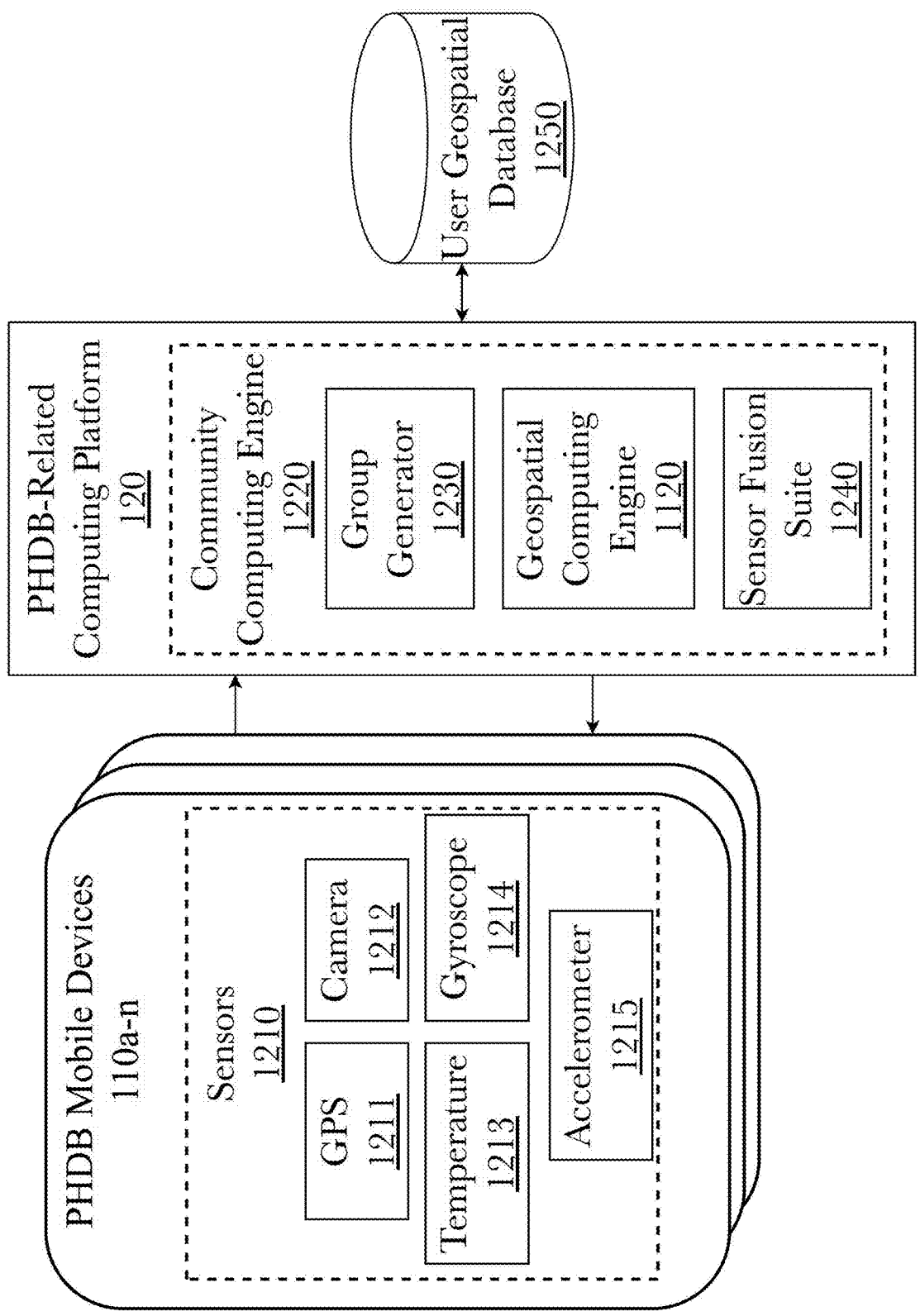
FIG. 12 is a system diagram showing an exemplary arrangement of a PHDB computing system using geospatial and community-based computing techniques and user grouping techniques, according to an aspect of the invention.

FIG. 12 is a system diagram showing an exemplary arrangement of a PHDB computing system using geospatial and community-based computing techniques and user grouping techniques, according to an aspect of the invention. User geospatial database 1250 actively receives and stores real-time geospatial data from subscribed users. This stored data may be retrieved by PHDB-related computing platform 120 to facilitate various community computing processes. These users utilize PHDB mobile devices 110a-n equipped with various sensors, such as GPS 1211, Camera 1212, Temperature 1213, Gyroscope 1214, and Accelerometer 1215. The data collected by these sensors is then transmitted to the PHDB-related computing platform 120, housing the community computing engine 1220.

According to the embodiment, community computing engine 1220 may comprise both a group generator 1230 and a geospatial computing engine 1120. The community computing engine 1220 facilitates the dynamic creation of ad hoc local groups, enables the establishment of persistent groups by users or third parties, and performs oracle detection. The computed data resulting from these operations is subsequently stored with user geospatial database 1250.

Specifically, group generator 1230 within the community computing engine 1220 is responsible for creating ad hoc local groups, allowing users to collaborate seamlessly based on real-time contextual factors. For example, groups may be created wherein members of the group are selected based on subsets of information stored in their individual PHDBs. For instance, groups may be based on shared common activities. Groups may be formed based on shared genetic information. Groups may be formed based on a score associated with human compatibility based on filtering of human genomes. Groups may be formed based on virtual environments or actual environments. Additionally, it provides functionality for users or third parties to establish and maintain persistent groups, fostering ongoing collaboration and data sharing.

Simultaneously, the geospatial computing engine 1120, also part of the community computing engine, processes the geospatial data received from the users. This engine performs intricate calculations and analyses to derive valuable insights, contributing to enhanced situational awareness and decision-making capabilities.

The overall system also incorporates an oracle detection mechanism within the community computing engine 1120. This feature enhances the system's ability to identify and respond to critical events or anomalies based on the processed data.

The PHDB-related computing platform 120 acts as a centralized hub where the data from various users and computing engines is consolidated and processed. Subsequently, the refined and computed data is stored in user geospatial database 1250. The PHDB computing system effectively utilizes geospatial and community-based computing techniques, coupled with advanced user grouping capabilities, to enhance real-time collaboration, data sharing, and decision-making within a dynamic and interconnected environment.

Figure 13:
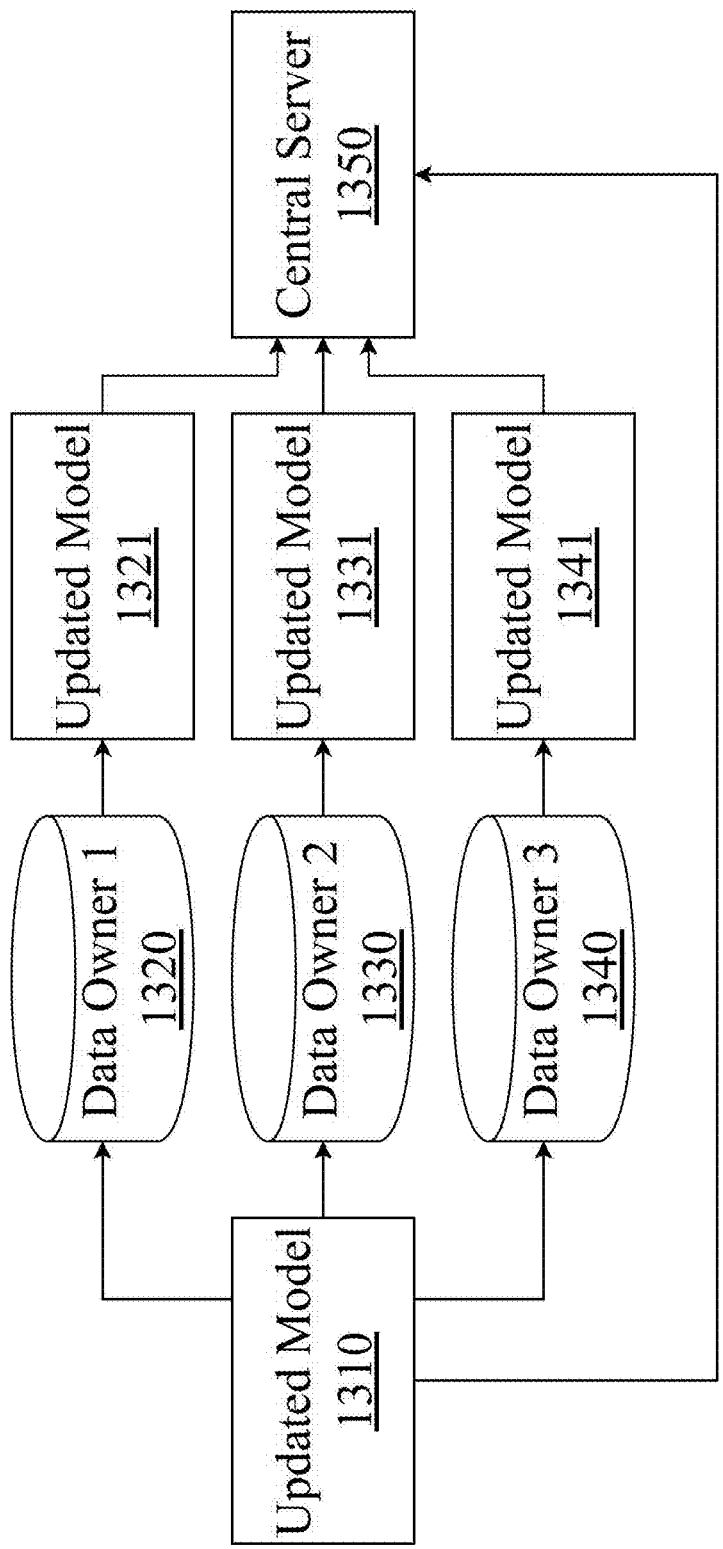
FIG. 13 is a system diagram showing an exemplary arrangement of federated computing, according to an aspect of the invention.

FIG. 13 is a system diagram showing an exemplary arrangement of federated computing, according to an aspect of the invention. The updated model 1310 is designed to share data seamlessly within a federated environment, demonstrating the flexibility of data federation. In this configuration, the updated model 1310 can directly communicate with the central server 1350, employing data federation protocols for efficient data exchange.

According to the embodiment, a plurality of data owners 1320, 1330, and 1340 are present and each in possession of some data. For instance, each data owner may represent PHDB user with a PHDB-enabled mobile device. The different data owned by the different people may be related, but different. For example, each data owner may store a plurality of personal health information. On each federated device there is a model 1321, 1331, and 1341 that can be stored and operated on the device. These models may function by processing local data. Periodically, each federated device may send updated models or model parameters to a central server 1350. The central server can perform model update tasks using the received models or model parameters from each of the federated devices. For example, a central server could aggregate the received model parameters to create a single set of model parameters with which to update a shared model. This updated model 1310 may be distributed to each of the federated device data owners, where it may be stored and operated.

Alternatively, the updated model 1310 can utilize data owner 1 1320, data owner 2 1330, and data owner 3 1340 as federation proxies. These proxies serve as intermediaries or agents, facilitating the exchange, retrieval, or processing of data between federated systems or networks. Their role extends to managing and securing data transactions within the federated environment.

In this federated setup, data owner 1 1320 acts as a proxy for data exchange with updated model 1321, data owner 2 1330 with updated model 1331, and data owner 3 1340 with updated model 1341. Each data owner serves as a localized point of contact, streamlining the data flow and ensuring efficient communication between the Updated Models and the corresponding Data Owners.

Subsequently, the data shared between each data owner and their respective updated models can be aggregated and transmitted to the central server 1350. This approach allows for a distributed and collaborative data-sharing model within the federated computing system.

The use of federation proxies not only enhances the efficiency of data transactions but also contributes to the overall security and management of the federated environment. By incorporating these intermediaries, the system ensures that data is exchanged seamlessly and securely across the federated network, promoting enhanced interoperability and collaboration.

This type or arrangement may also be used to represent edge computing wherein mobile devices representing data owners may train and maintain models on the device which process and analyze stored data. Periodically, these edge devices can submit their models to central server 1350 where they may be used to form a single updated model which can then be deployed back to the edge devices for further training and operation.

Figure 14:
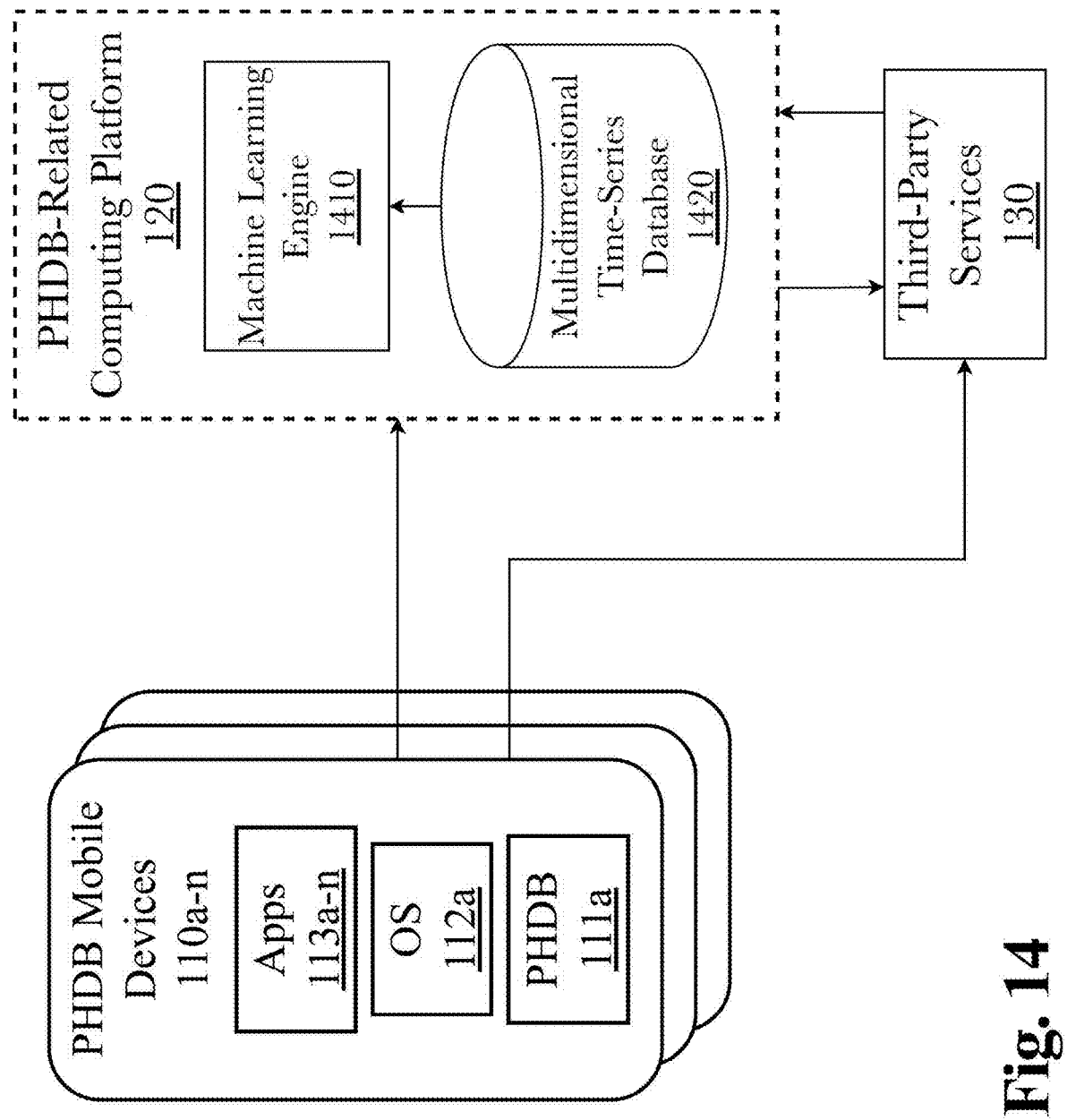
FIG. 14 is a system diagram showing an exemplary arrangement of a service prediction mechanism using a multidimensional time-series database, according to an aspect of the invention.

FIG. 14 is a system diagram showing an exemplary arrangement of a service prediction mechanism using a multidimensional time-series database, according to an aspect of the invention. Users equipped with PHDB mobile devices 110*a-n*, comprising applications 113*a-n*, an operating system (OS) 112*a*, and the PHDB application 111*a*, have the capability to share data directly with the PHDB-related computing platform 120. This platform encompasses a Multidimensional Time-Series Database (MTSDB) 1420, serving as a pivotal component in the system's predictive capabilities. The MTSDB 1420 can provide a source for creating training, validation, and test datasets from the shared data to a machine learning engine 1410.

Alternatively, users may opt-in to share their data with third-party services 130, which then relay the data to the PHDB-related computing platform 120. The MTSDB 1420 receives events from various related services, continuously updating with real-time events and aggregate data. This dynamic database is instrumental in conducting simulations aimed at predicting service demand and generating optimization recommendations for services.

The predictive capabilities of the system are harnessed through simulations facilitated by the Multidimensional Time-Series Database 1420. By analyzing real-time data, the system can anticipate service demands, allowing for proactive decision-making and resource optimization. Furthermore, the generated optimization recommendations contribute to refining the performance of the associated services.

The Multidimensional Time-Series Database 1420 plays a central role in the generation of real-time screening candidates and world-scale simulations. It acts as a comprehensive repository of temporal data, providing a foundation for accurate predictions and informed decision-making within the various services. Temporal data may be ingested or otherwise obtained by PHDB-related computing platform 120. Temporal data related to a person's omics information can include changes in gene expression levels over time, variations in metabolite levels in response to diet or medication, fluctuations in epigenetic markers like DNA methylation patterns, and alterations in the microbiome composition. Tracking how the expression of specific genes changes over time can provide insights into disease progression or response to treatment. Monitoring the levels of metabolites in the body over time can reveal patterns related to metabolic health, response to diet, or drug metabolism. Studying changes in DNA methylation patterns over time can help understand how environmental factors influence gene expression and disease risk. Observing how the composition of the gut microbiome changes over time can offer insights into digestive health, immune function, and even mental health. Analyzing changes in protein expression and modification patterns over time can provide information about cellular processes and disease mechanisms.

According to the embodiment, machine learning engine 1410 may be configured to create, store, and maintain one or more predictive or analytical models developed using machine and/or deep learning techniques. The one or more predictive or analytical models may be directed to generating a score that represents the compatibility of two or more people based on analysis of declared preferences such as, for example, a preferred genomic profile or attribute. Preferences may be directed to, for example (and not limited to), genetic, emotional, religious, or behavioral kinds of preferences or constraints. For example, assume Person-A set in their profile that they want to screen out anyone with a high potential for cystic fibrosis. Person-A walks into a room (at some venue-concert hall, convention center, restaurant, etc.) and their device begins the screening process to score everyone (that opts-in) in the room. The device can show a score for each individual (that opts-in) which reflects the relative match between Person-A and the other individuals based on each person's individual criteria (e.g., preferences).

According to the embodiment, machine learning engine 1410 may train one or more machines and/or deep learning algorithms to create a model. The data used for model training purposes may comprise subsets of data stored in a plurality of PHDBs. The training data may further comprise PHDB-enabled device-specific data or metadata such as mobile device location information, a device IP address, and/or the like. Training data may further be sourced from MTSDB 1420 or third-party services 130 such as, for example, social media servers, medical services providers, data centers, and medical/behavioral/therapeutic/etc. labs. Training data may further be sourced from various IoT devices 140.

In summary, the disclosed system leverages a multidimensional time-series database as a core component in a service prediction mechanism. By integrating predictive analytics and machine learning, the system enhances its ability to forecast service demands, generate optimization recommendations, and facilitate real-time screening candidates and large-scale simulations.

Figure 15:
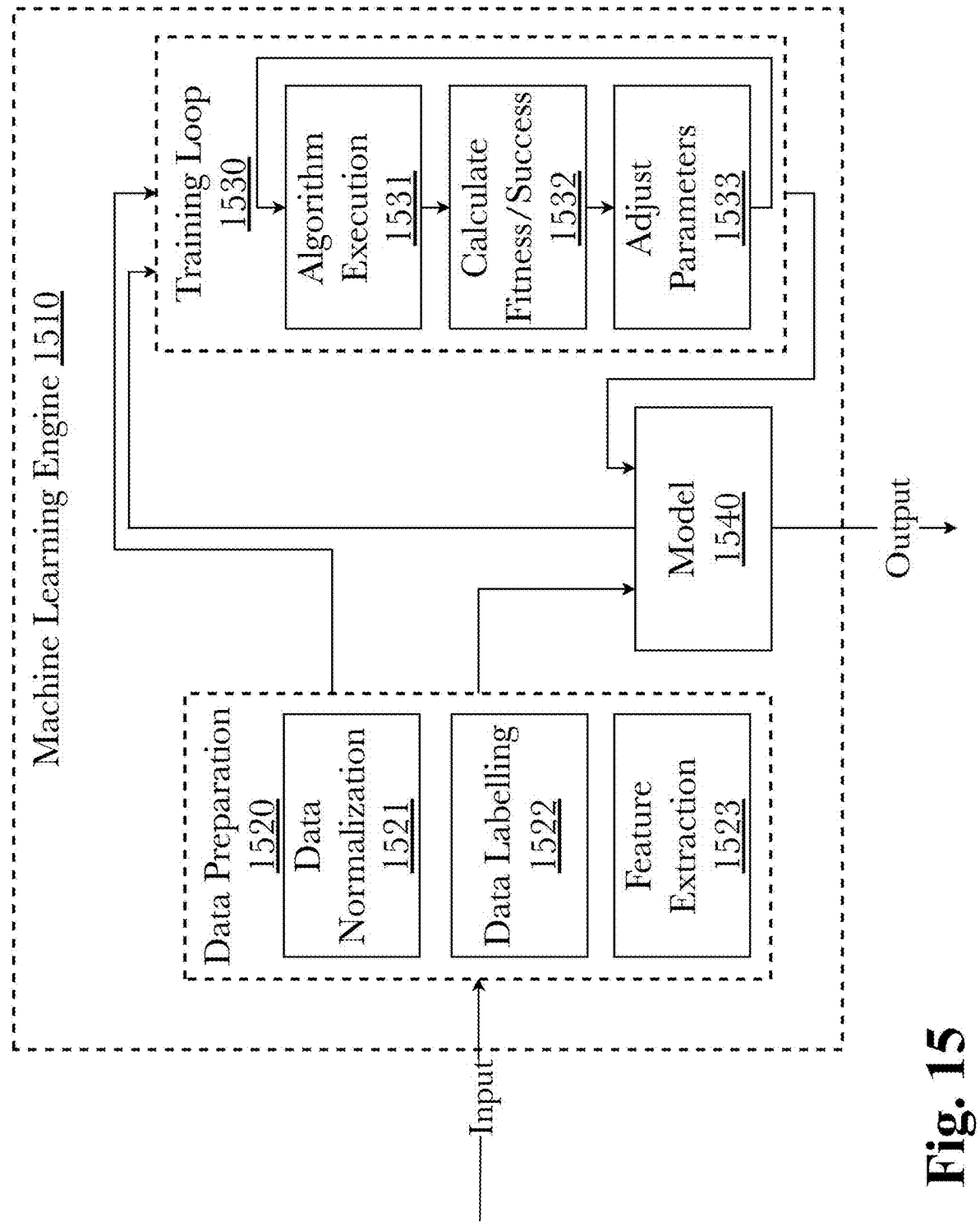
FIG. 15 is a system diagram illustrating an exemplary architecture of a machine learning engine.

FIG. 15 is a system diagram illustrating an exemplary architecture of a machine learning engine. A machine learning engine 1510 may be a software component, standalone software library, system on a chip, application-specific integrated circuit ("ASIC"), or some other form of digital computing device or system capable of interacting with and receiving data from other digital or software systems. It may be connected over a network, or connected within a system or computer, and may be utilized by software processes or communicate with them as a separate application or process instance. The basic components within a machine learning engine, broadly, are a data preparation 1520 loop or algorithm, which may contain some combination of steps, commonly including data normalization 1521, data labeling 1522, and feature extraction 1523, depending on the exact implementation or configuration of a machine learning engine 1510. A key feature of a machine learning engine 1510, is the existence of some form of a training loop 1530 in their software or chip design, a series of steps taken to take input data and learn how to process it and produce some desired output. A machine learning engine 1510 may be configured or implemented poorly merely as a matter of execution, and may have trouble learning efficiently or at all, or have difficulty learning usefully from certain knowledge areas or domains, but all machine learning systems contain a training loop of some kind, and they frequently contain the subcomponents or steps of having algorithm execution perform over the set of input data 1531, calculating the fitness or success states or success rate of the algorithm with a current model 1540, and adjusting the parameters of the model to attempt to output better or more useful data for a given input data.

A model 1540 is a software or mathematical representation of data that impacts how an algorithm operates. An algorithm may be any set of concrete steps taken to attempt to process data or arrive at some solution to a problem, such as a basic search algorithm which tries to find a specified value in apparently unsorted numeric data. A basic attempt at such a search algorithm might be to simply jump around randomly in the dataset and look for the value being searched for. If machine learning were applied to such an algorithm, there might be a model of parameters for the algorithm to operate with, such as how far from the current index being examined in the input dataset, to be capable of jumping. For instance, in a set of 1,000 numbers in no readily apparent ordering or sorting scheme, the algorithm to randomly pick numbers until it finds the desired number may have a parameter that specifices that if you are currently at index x in the dataset being searched, you may only jump to a value between x−50 and x+50. This algorithm may then be executed 1531 over a training dataset, and have its fitness calculated 1532, in this example, as the number of computing cycles required to find the number in question. The lower the number, the higher the fitness score.

Using one of many possible parameter adjustment 1533 techniques, including linear regression, genetic variation or evolutionary programming, simulated annealing or other metaheuristic methods, gradient descent, or other mathematical methods for changing parameters in a function to try and approach desired values for specified inputs. Machine learning training method, that is, the way they adjust parameters 1533, may be deterministic or stochastic, as in evolutionary or genetic programming, or metaheuristics in general. Examples of genetic programming include the concept of genetic variation, whereby several different models of an algorithm are run over the same input data, compared for fitness, and a selection function determines which models to use for "breeding" the next "generation" of the model population, at which point a crossover function is used to recombine the "genes" (the word used in genetic programming to refer to function or model parameters) into different arrangements for each new member of the next generation, lastly applying a mutation function to alter (either randomly or statistically) some selection of genes from some selection of the newly bred models, before the process is repeated with the hope of finding some combinations of parameters or "genes" that are better than others and produce successively better generations of models.

Several machine learning methodologies may be combined, as with NeuroEvolution of Augmenting Topologies ("NEAT"), whereby a genetic algorithm is used to breed and recombine various arrangements of neurons and hidden layers and the parameters of neurons, in a neural network, reducing the use of human judgement in the design or topology of a neural network (which otherwise often requires a fair amount of trial and error and human judgement). These situations may be thought of either as multiple different training loops 1530 occurring with multiple models 1540, or may be thought of as multiple machine learning engines 1510 entirely, operating together.

Figure 16A:
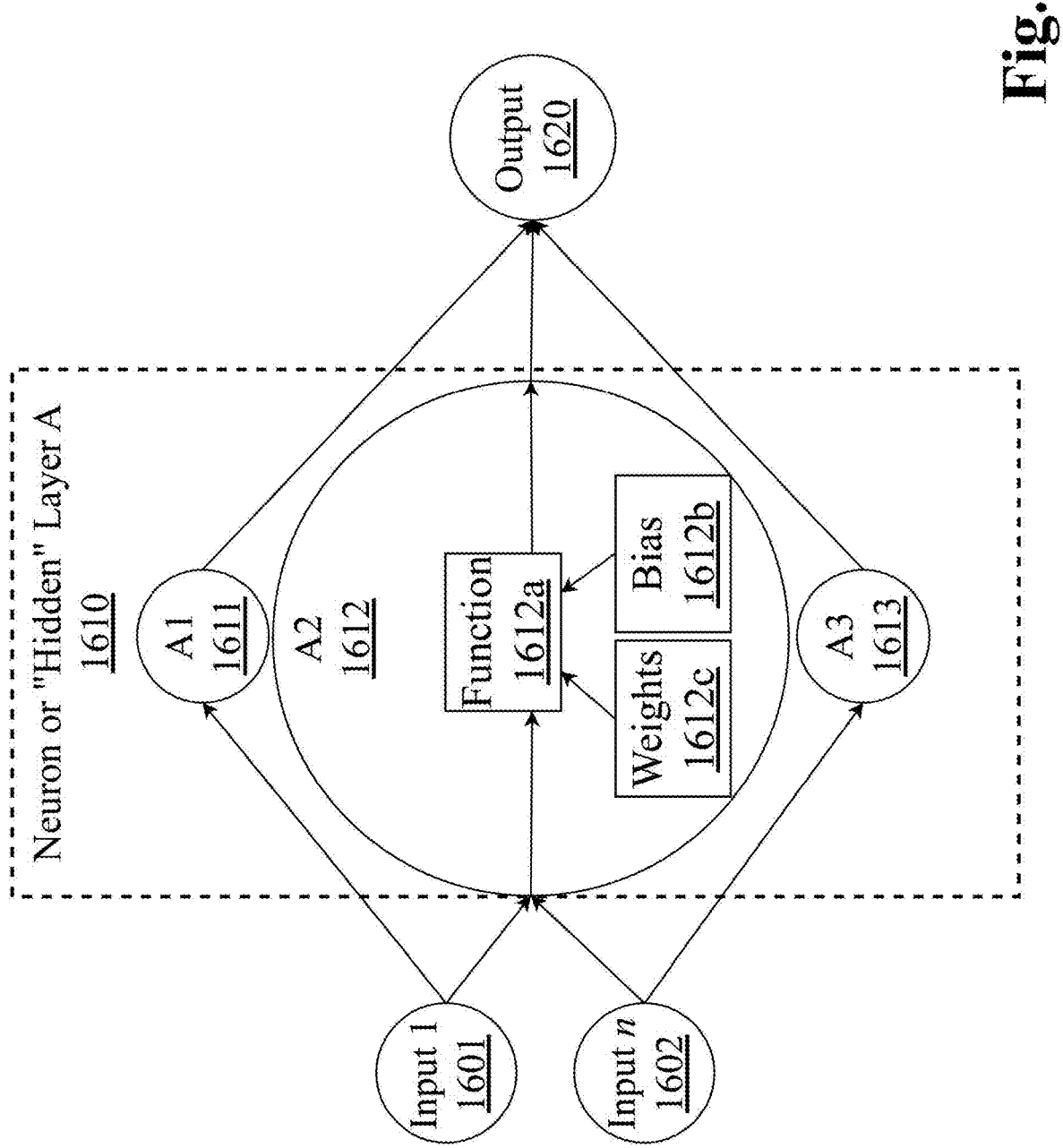
FIG. 16a is a diagram illustrating an exemplary architecture of a neural network.

FIG. 16a is a diagram illustrating an exemplary architecture of a neural network. A neural network is a software system that may be used to attempt to learn or improve an algorithm at a task or set of tasks, using mathematical models and approximations of biological neurons with artificial neurons. The kinds of tasks that may be used in combination with a neural network are potentially unlimited so long as the problem is deterministic, but common applications include classification problems, labeling problems, compression or algorithm parameter tuning problems, image or audio recognition, and natural language processing. Neural networks may be used as part of a machine learning engine, as the method by which training is done and a model is generated. A neural network contains at least one input, here labeled as input 1 1601, but may have multiple inputs, labeled input n 1602, that feed into a neuron layer or hidden layer 1610 which contains at least one artificial neuron, here shown with A1 1611, A2 1612, and A3 1613. Inside of each neuron are three components, an activation function 1612a, a bias 1612b value, and a weight for each input that feeds into the neuron 1612c. An activation function 1612a is the function that determines the output of the neuron, and frequently follows a sigmoidal distribution or pattern, but may be any mathematical function, including piecewise functions, identity, binary step, and many others. The activation function 1612a is influenced not only by the inputs into a neuron 1601, 1602, but the weight assigned to each input 1612c, which multiplies an input value by itself, and a bias 1612b, which is a flat value added to the input of the activation function 1612a. For instance, with a single input value of 17, a weight of 0.3, and a bias of 0.5, a neuron would run its activation function with an input of 5.6 (17*0.3+0.5). The actual output of the activation function 1612a, for each neuron, then may proceed to be output 1620 in some format, usually numeric, before being interpreted by the system utilizing the neural network. There may be multiple output values, representing confidence values in different predictions or classifications, or other multi-valued results.

Various forms and variations of neural networks exist which may be more or less applicable to certain knowledge domains or certain problem sets, including image recognition, data compression, or weather prediction. Some examples of different types of neural networks include recurrent neural networks (including variants thereof such as Long Short Term Memory recurrent neural networks), convolutional neural networks, deep learning networks, and feed forward neural networks, the last of which is regarded by many as the "standard" or most basic usable form of an artificial neural network.

Figure 16B:
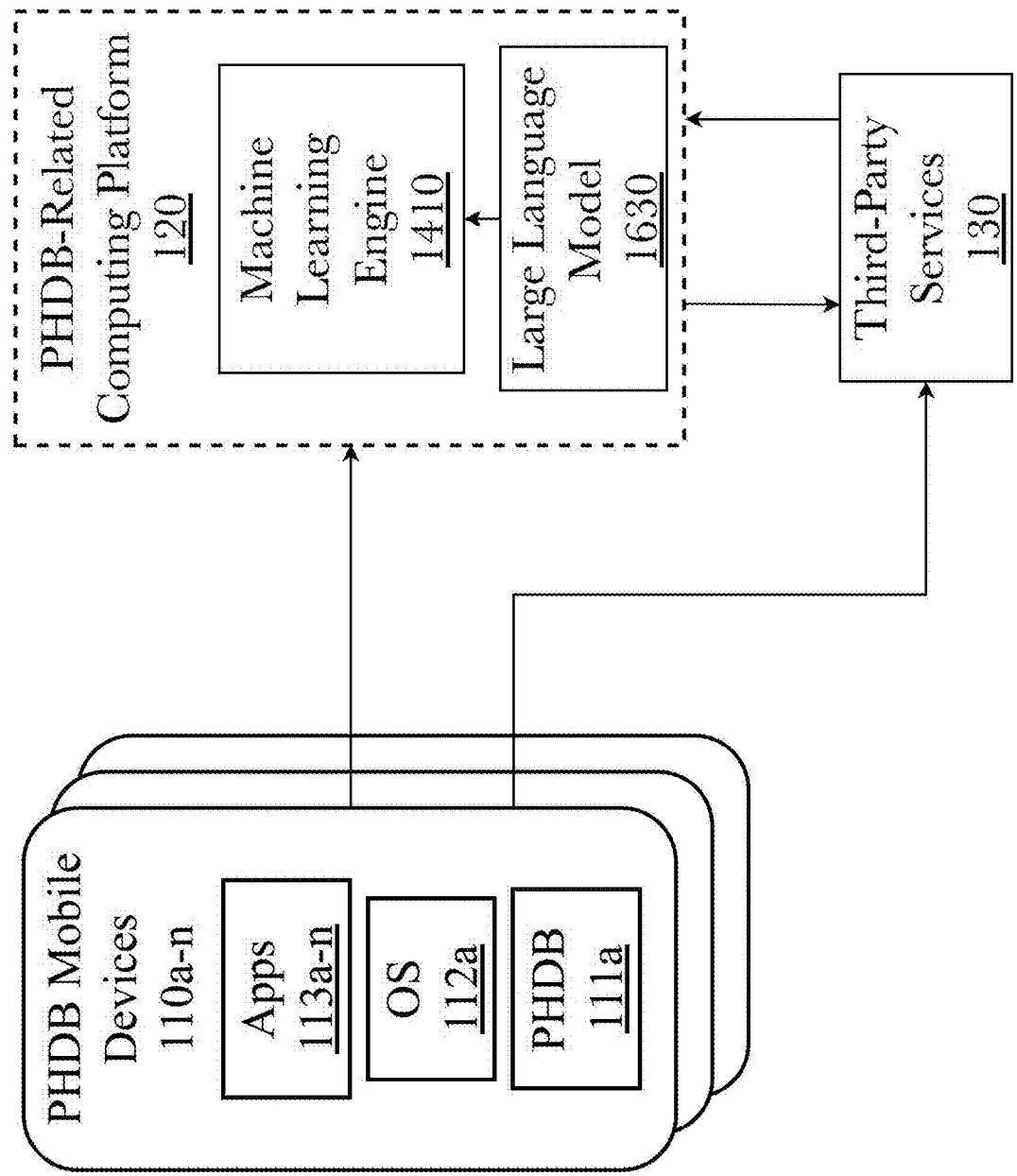
FIG. 16b is a system diagram showing an exemplary arrangement of a PHDB system utilizing Large Language Model (LLM) machine learning technology, according to an aspect of the invention.

FIG. 16b is a system diagram showing an exemplary arrangement of a PHDB system utilizing Large Language Model (LLM) machine learning technology, according to an aspect of the invention. Users equipped with PHDB mobile devices 110a-n, comprising applications 113a-n, an operating system (OS) 112a, and the PHDB application 111a, possess the capability to share data directly with the PHDB-related computing platform 120.

It should be appreciated that the illustrated LLM 1630 is merely an exemplary machine learning model that may be utilized according to various aspects, and that other AI/ML systems may be used in various embodiments. In some aspects, a neuro-symbolic AI system may be implemented which blends LLMs or other Connectivist models with symbolic models. Such a neuro-symbolic model may be used to provide AI planning solutions and simulation to enable a much more complex reasoning/planning and operations/optimization with awareness of resources. A neuro-symbolic model that incorporates Connectivist principles combines elements of neural networks and symbolic reasoning to create a hybrid approach to AI. According to an aspect, a neural network component processes raw data, such as images, text, or sensor inputs, to extract relevant features and learn patterns. This component is responsible for tasks like image recognition, natural language processing, or sensor data analysis. The symbolic reasoning component manipulates abstract symbols and rules to perform tasks that require logical reasoning or explicit knowledge representation. This component is responsible for tasks like logical inference, planning, or knowledge representation. Connectivism emphasizes the importance of connections and networks in learning. In a neuro-symbolic model, Connectivist principles might be used to guide how the neural and symbolic components interact and learn from each other. This could involve feedback loops where symbolic reasoning helps guide the learning of the neural network, and the neural network's outputs inform symbolic reasoning. The integration of neural and symbolic components can happen at various levels. For example, the output of a neural network might be fed as input to a symbolic reasoning system, which then uses logical rules to make decisions or generate new knowledge. Conversely, the output of symbolic reasoning might be used to guide the training or behavior of the neural network.

According to the embodiment, platform 120 incorporates an LLM 1630, which may be trained and maintained by machine learning engine 1410. The user can transfer data directly to the platform, or alternatively, choose to share data with a third-party service 130, which then facilitates the relay of data to the LLM machine learning technology on the PHDB-Related Computing Platform 120. According to an aspect, a user of mobile device 110*a* may be able to submit a prompt via PHDB app 111*a* to LLM 1630 which can process the prompt and provide a response to the user of mobile device 110*a*. In some implementations, an instance of LLM 1630 may be deployed locally on a mobile device 110*a*. In such implementations, platform 120 may leverage federated learning with edge computing via PHDB mobile devices 110*a-n*.

The shared data plays a pivotal role in establishing a baseline for the LLM 1630. This model, equipped with machine learning capabilities, is not only capable of receiving requests (e.g., prompts) from other computing services but also adept at generating appropriate responses to fulfill the requirements of these services. In some implementations, multiple LLMs may be developed, wherein each of the multiple LLMs may be configured to specific domain or preference. For example, a first LLM may be trained to be a resource for use cases involving genomic assistance, and a second LLM is trained to be a resource for use cases involving microbiome-based assistance. In other implementations, an LLM may be personalized to an individual user. In such implementations, the user may opt-in to allow the LLM access to all their stored personal health data 200 thereby allowing the LLM to better understand and anticipate user queries and intentions.

LLM 1630 continuously updates based on PHDB-centric user interactions. This dynamic learning process ensures that the LLM remains adaptive and responsive to evolving user needs and preferences.

In summary, the disclosed PHDB system, incorporating Large Language Model (LLM) machine learning technology, empowers users to share data directly with the PHDB-Related Computing Platform. The integration of LLM enhances the system's ability to comprehend and generate responses to user queries, creating a sophisticated and adaptive environment for users.

Figure 17:
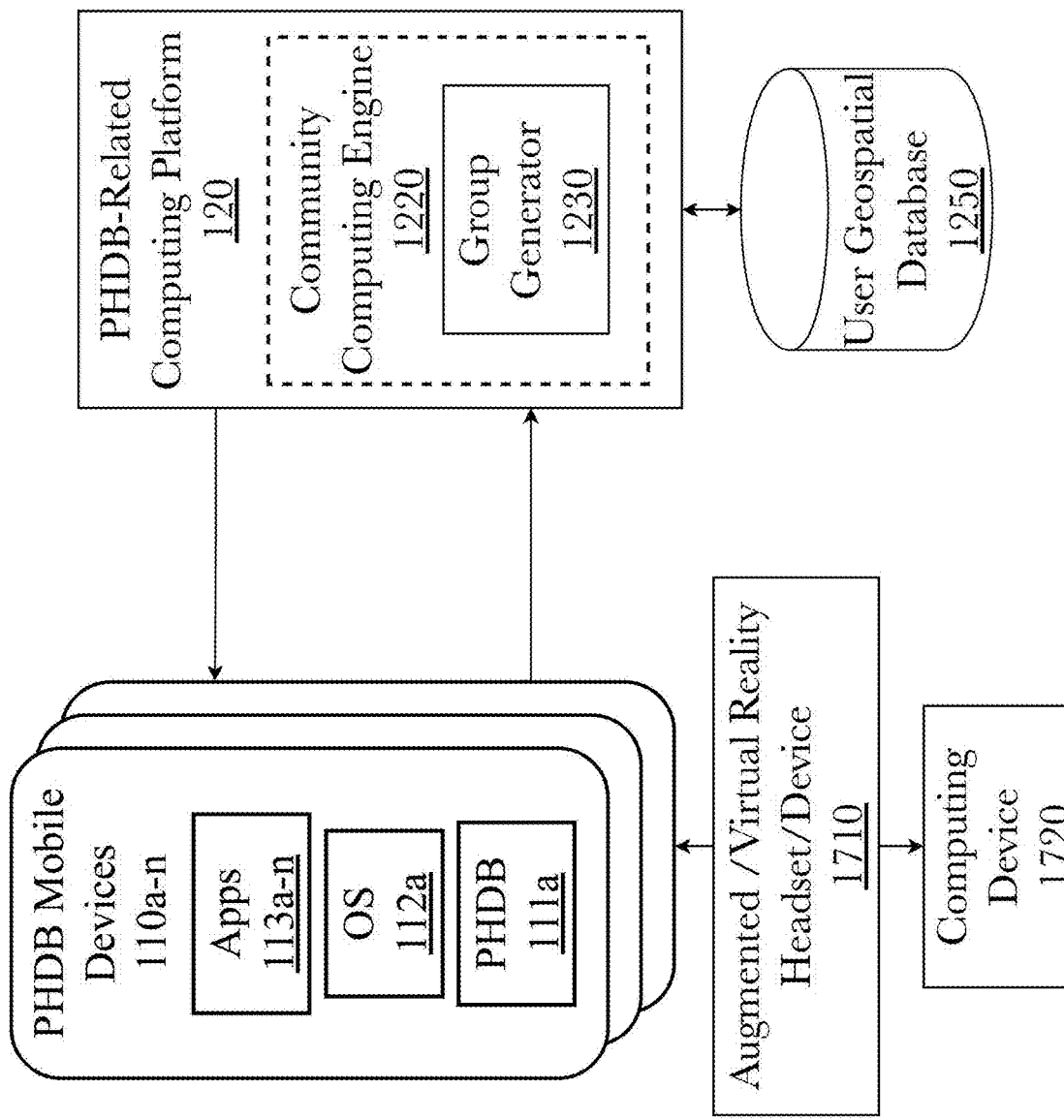
FIG. 17 is a system diagram showing an exemplary arrangement of a PHDB computing system utilizing Augmented Reality (AR) or Virtual Reality (VR) technologies, according to an aspect of the invention.

FIG. 17 is a system diagram showing an exemplary arrangement of a PHDB computing system utilizing Augmented Reality (AR) or Virtual Reality (VR) technologies, according to an aspect of the invention. Augmented reality or virtual reality headsets or devices 1710 are employed to share data with both a computing device 1720 and PHDB Mobile Devices 110*a-n*.

PHDB Mobile Devices 110*a-n*, comprising applications (Apps) 113*a-n*, an operating system (OS) 112*a*, and the PHDB application 111*a*, receive data shared by the AR or VR Headset or device. In some arrangements, PHDB mobile devices 110*a-n* and/or computing device 1720 may be configured to send control signals to AR/VR headset 1710 for controlling or otherwise manipulating the AR/VR environment. Subsequently, the PHDB mobile devices can transmit this data to the PHDB-related computing platform 120.

The PHDB-Related Computing Platform 120 encompasses a community computing engine 1220, which in turn includes a group generator 1230. This engine is pivotal in creating ad hoc local groups through its group generator and facilitates seamless data sharing within the community. The PHDB-related computing platform 120 then disseminates the shared data to the user geospatial database 1250.

In an exemplary use case, the data stored in PHDBs associated with AR/VR headset/device users may be used to identify playing groups for a virtual reality game. Group generator 1230 could obtain various user geospatial data to identify AR/VR users in a given area nearby a first player to initially identify a group to play with. Then, PHDB data and preferences could be obtained from the identified players to refine the group list based on matched preferences and statistical analysis thereof. The refined group may be presented to the AR/VR users such as by an invitation to join a playing group, or an invitation to meet at a physical location somewhere nearby (as determined by user defined preferences for distances willing to travel on foot, etc.) to participate in a group AR/VR session.

The utilization of AR or VR technologies enhances the user experience by providing an immersive interface for data sharing. This integration of spatial computing enriches user interactions and contributes to the creation of dynamic local groups, fostering collaborative and real-time data exchange within the PHDB ecosystem.

Figure 18:
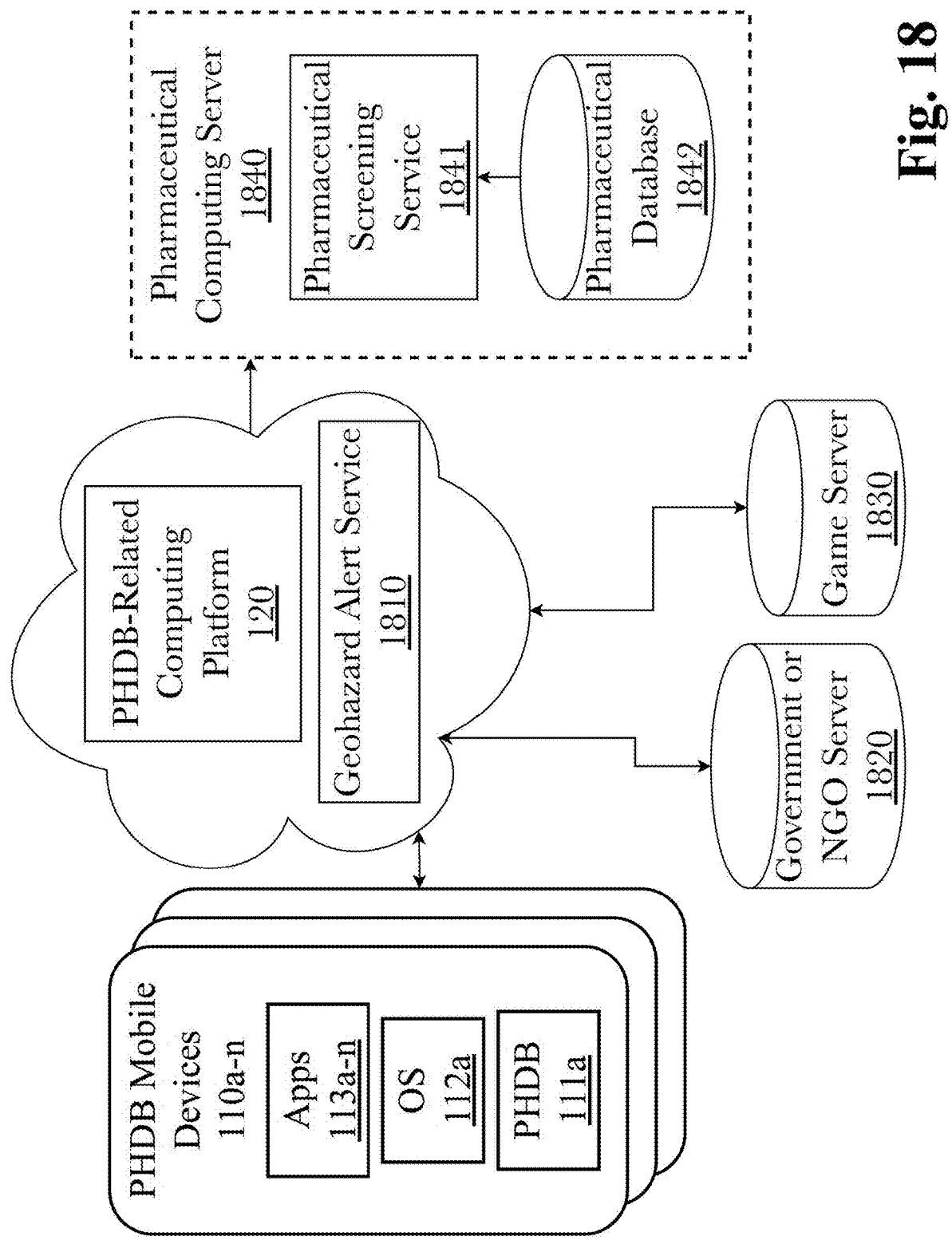
FIG. 18 is a system diagram showing an exemplary arrangement of a PHDB computing system utilizing a variety of possible third-party services and servers, according to an aspect of the invention.

FIG. 18 is a system diagram showing an exemplary arrangement of a PHDB computing system utilizing a variety of possible third-party services and servers, according to an aspect of the invention. The PHDB mobile devices 110*a-n* may include Apps 113*a-n*, an operating system (OS) 112*a*, and the PHDB application 111*a*, and can engage in data sharing with the cloud infrastructure. This cloud includes the PHDB-related computing platform 120 and a geohazard alert service 1810.

The data shared within the cloud is then further transmitted to a variety of third-party services, enhancing the functionality and utility of the PHDB system. Notable third-party services include government or non-governmental organization (NGO) server 1820, a game server 1830, and a pharmaceutical computing server 1840.

Within the pharmaceutical computing server 1840, a pharmaceutical database 1842 is housed, facilitating the transfer of data to the pharmaceutical screening service 1841. This specialized service is designed to analyze and screen health-related data, contributing to the overall capabilities of the PHDB system in relation to pharmaceutical information.

Geohazard alert service 1810 is a service that provides timely information and warnings about geological hazards, such as earthquakes, landslides, volcanic eruptions, and tsunamis. These services use data from various sources, including seismic sensors, GPS stations, satellite imagery, game servers, governmental and NGOs, and geological surveys, to detect and monitor potential hazards and to issue alerts to the public and relevant authorities.

Government or NGO servers 1820 can host information or send out warnings about a geohazard (e.g., war, national security advisory, natural disaster, etc.) and the PHDB computing platform 120 scans known government/NGO servers for hosted information, and/or receives alerts. Users that are known to be in those locations where a geohazard has occurred, may be proactively alerted if the users have appropriate security rules and encryption practices that allow for it.

During geologically hazardous events where people are injured or need treatment, PHDB mobile devices can alert platform 120 of the types of treatment or medicine that people in the crisis need. This information can be communicated to the appropriate governmental organizations and NGOs to begin the process of aid procurement and may be further communicated to nearby pharmaceutical computing servers 1840 to begin processing the shipment of the required medications or other medical supplies.

This integration of third-party services extends the reach and applicability of the PHDB system, providing users with diverse functionalities ranging from government-related services, gaming applications, to pharmaceutical screenings.

Figure 19:
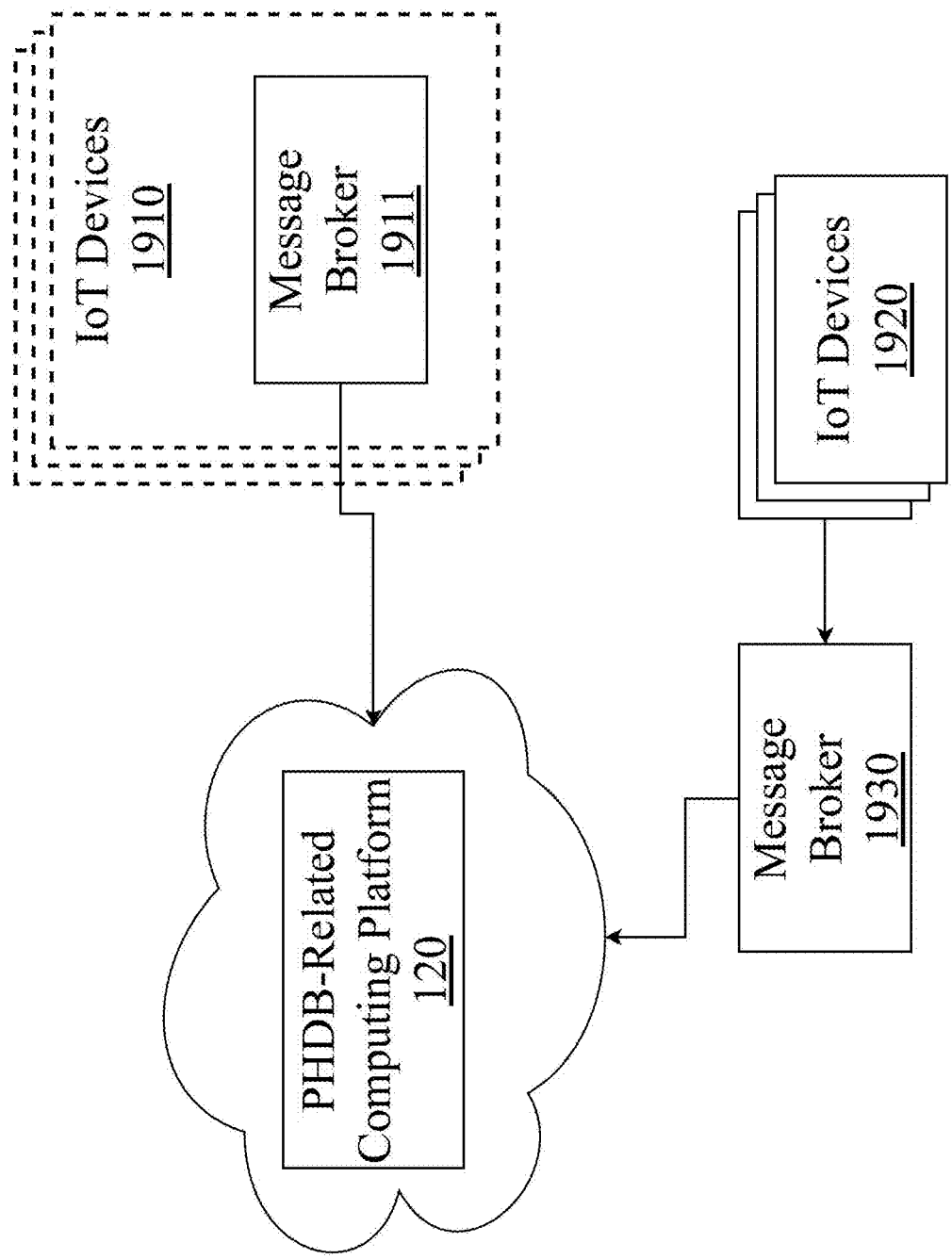
FIG. 19 is a system diagram showing an exemplary arrangement of a PHDB computing system utilizing Internet-of-Things (IoT) devices and associated technology, according to an aspect of the invention.

FIG. 19 is a system diagram showing an exemplary arrangement of a PHDB computing system utilizing Internet-of-Things (IoT) devices and associated technology, according to an aspect of the invention. IoT devices 1910, equipped with various sensors and technologies, form an integral part of the system architecture.

These IoT devices 1910 communicate with an embedded message broker 1911, serving as a central communication hub. The message broker facilitates the efficient and secure exchange of data between the IoT Devices 1910 and the PHDB-Related Computing Platform 120. This bi-directional data sharing ensures a seamless flow of information between the physical environment monitored by the IoT Devices and the computational capabilities of the PHDB system.

Furthermore, the message broker 1930 plays a critical role in managing distributed communication flow. It acts as an intermediary, collecting data from the IoT Devices 1920 and transmitting it to the cloud based PHDB-Related Computing Platform 120. This approach enhances the scalability and flexibility of the system, allowing for the integration of diverse IoT Devices with different communication protocols and data formats.

The data shared by the IoT Devices encompasses various health-related parameters, contributing to the comprehensive genomic health monitoring capabilities of the PHDB system. This integration of IoT technology enhances real-time data acquisition and expands the scope of genomic health-related information that can be incorporated into the PHDB.

Detailed Description of Exemplary Aspects

Figure 20:
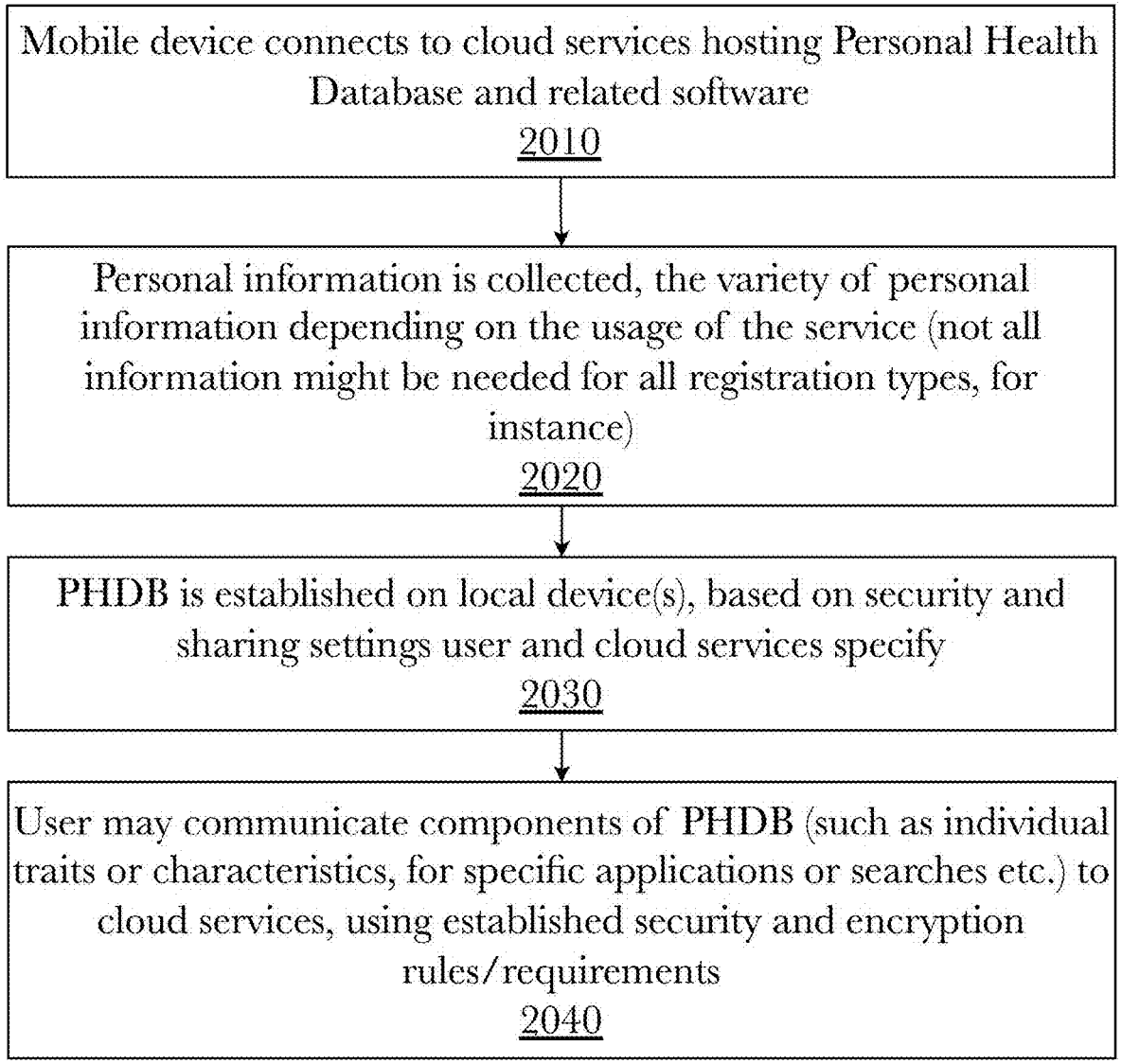
FIG. 20 is a method diagram showing exemplary steps taken for a user to register and establish a PHDB, according to an aspect of the invention.

FIG. 20 is a method diagram showing exemplary steps taken for a user to register and establish a PHDB, according to an aspect of the invention. According to the aspect, the process begins at step 2010 when the user's mobile device establishes connection to cloud services 101 hosting the Personal Health Database and related software. This initial connection may be made responsive to the user downloading and storing a PHDB software application 111*a* on their PHDB-enabled mobile device 110*a* and opening the PHDB application for the first time as part of the onboarding process. Additionally, or alternatively, the user may establish the initial connection by accessing a PHDB associated website or web application on their computing device (e.g., personal computer or laptop). At a next step 2020 personal information is then collected, with the specific type and extent of information gathered depending on the intended usage of the service 2020. It's noteworthy that not all information may be required for every registration type, ensuring flexibility and user customization. Examples of the types of personal information that can be collected can include, but is in no way limited to, genomic data, microbiome data, phenotype data, biometric data, activity data, preference data including likes and dislikes, medical data, demographic data, physiological data, behavioral data, social media data, education data (e.g., highest level of education achieved), and/or the like. The personal information may be collected from a plurality of sources. For example, PHDB users can directly submit their personal information via PHDB application 111*a* stored and operating on their mobile device. Users may be guided through a process that can query the user for various types of personal information that the user may optionally choose to submit for storage in their PHDB. Mechanisms such as surveys or questionnaires can be used as a means to collect personal information. Additionally, or alternatively, PHDB users can select (i.e., provide consent to) various applications and/or third-party services for providing user-selected personal information that the applications and/or third-party services are in possession of. For example, a user can provide consent for a subset of their social media data to be uploaded to their PHDB. As another example, a user can consent to their medical provider to provide their electronic health record, or a subset thereof, for inclusion into their PHDB.

PHDB is established on local device(s), based on security and sharing settings specified by both the user and the cloud services 2030. This step ensures that the user has control over the security parameters and sharing preferences of their personal health data. The PHDB may be stored as an encrypted database on the user's local device.

To provide various functionality, a user may communicate components of PHDB (such as individual traits or characteristics, for specific applications or searches, etc.) to cloud services, using established security and encryption rules/requirements 2040. For example, components of PHDB may be encrypted (e.g., AES, homomorphic encryption, some combination thereof, etc.). Rules such as two-factor authentication and various access rules may be implemented to verify users who attempt to share personal information and to ensure that only user-selected individuals are able to receive the personal information.

Throughout these steps, the user is empowered to customize their PHDB based on their unique needs and preferences. The secure communication protocols and encryption mechanisms guarantee the confidentiality and integrity of the shared data, fostering a trustful and privacy aware environment for the user.

The disclosed method for registering and establishing a PHDB offers a user-centric approach, allowing individuals to tailor their health database while ensuring robust security measures during data transmission to and from cloud services.

Figure 21:
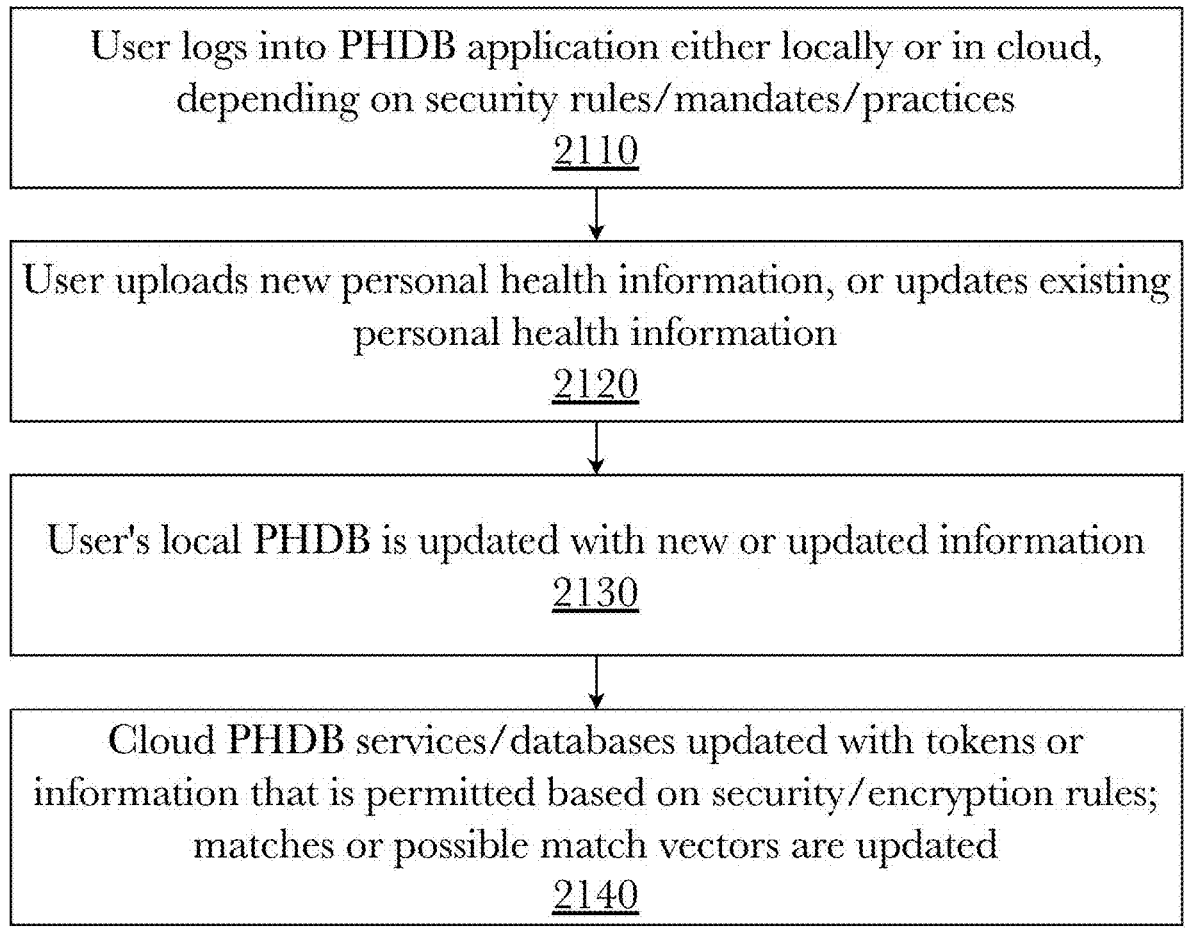
FIG. 21 is a method diagram showing exemplary steps taken for a user to update their data or information in a PHDB, according to an aspect of the invention.

FIG. 21 is a method diagram showing exemplary steps taken for a user to update their data or information in a PHDB, according to an aspect of the invention. According to the aspect, the process begins at step 2110 as the user logs into PHDB application, either locally or in the cloud, based on security rules, mandates, or practices. For example, a user may first have to verify their identity before being allowed to edit or otherwise update their personal information such as by using biometric data to provide two-factor authentication. As another example, a user may establish rules that allow updates to their PHDB to be performed only when a user is logged into a specific device, or location, or certain time of the day. These are merely examples of the types of rules/restrictions that a user can optionally select to establish a level of PHDB security they are comfortable with.

The user then uploads new personal health information, or updates existing personal health information within the PHDB application 2120. The user's local PHDB is subsequently updated with the new or modified information 2130. This local update ensures that the user's device is current and reflective of the most recent health-related data. To maintain consistency across the PHDB ecosystem, the Cloud PHDB services and databases are updated with tokens (e.g., distributed ledger token) or information that is permitted based on security/encryption rules 2140. This ensures that the central repository of health data, accessible through cloud services, is synchronized with the user's updated information while adhering to established security protocols. The inclusion of this updated personal information may affect the types of matches or possible matches that have been determined for the user who updated their information. As such, the cloud based PHDB services may update match or possible match vectors to reflect the updated information.

Figure 22:
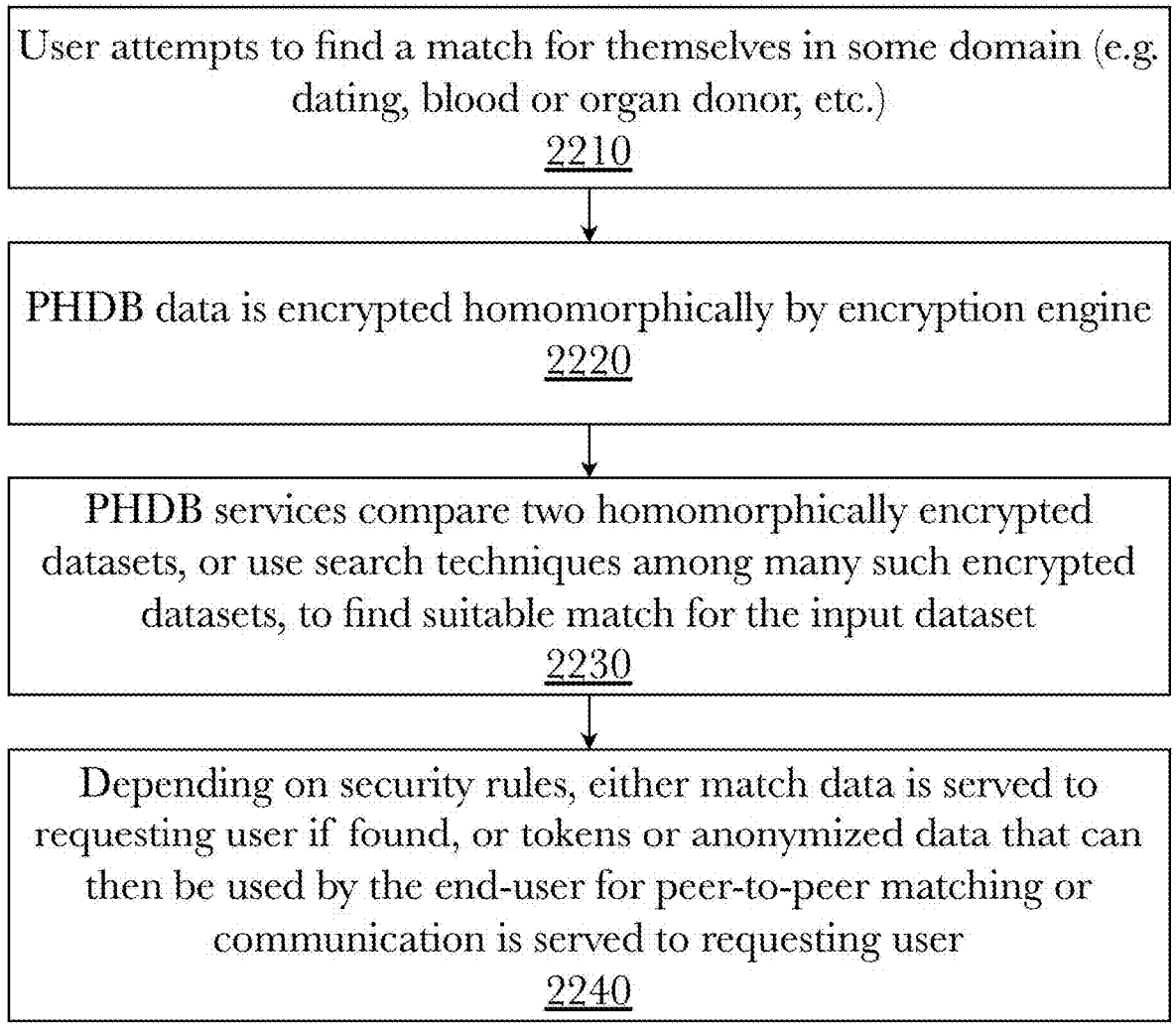
FIG. 22 is a method diagram showing exemplary steps taken for homomorphic encryption to be utilized with a PHDB, according to an aspect of the invention.

FIG. 22 is a method diagram showing exemplary steps taken for identifying a match using homomorphic encryption with a PHDB, according to an aspect of the invention. According to the aspect, the process begins at step 2210 as the user attempts to find a match for themselves in a specific domain, such as dating, blood or organ donor, gaming partner, etc. The PHDB data is then subjected to homomorphic encryption by an encryption engine at step 2220. In an embodiment, the homomorphic encryption scheme is partially homomorphic encryption. In an embodiment, the homomorphic encryption scheme is fully homomorphic encryption. This encryption process ensures that sensitive health-related information remains confidential while still allowing for meaningful comparisons and searches. At a next step 2230 PHDB services compare two homomorphically encrypted datasets, or use search techniques among multiple encrypted datasets, to identify a suitable match for the input dataset. For example, encrypted datasets may undergo a simple equality comparison, a similarity comparison (e.g., measuring the similarity between two encrypted vectors), or another type of comparison depending on the application, domain of interest, or some other limiting factor. This approach enables secure and privacy-preserving matching processes, safeguarding the integrity of the users' health data. In some embodiments, user PHDB profiles and preferences may be analyzed by a trained model and a score produced which is indicative of a potential match or a potential non-match.

Depending on security rules, if a match is found, match data is served to the requesting user. In some embodiments, the match data that is served to the requesting user may first be decrypted, if the involved users have allowed such sharing of personal information. Alternatively, tokens or anonymized data may be provided, allowing the end-user to engage in peer-to-peer matching or communication without revealing sensitive information directly 2240. This ensures that privacy is maintained during the matching process, and users have control over the level of detail shared with potential matches.

Figure 23:
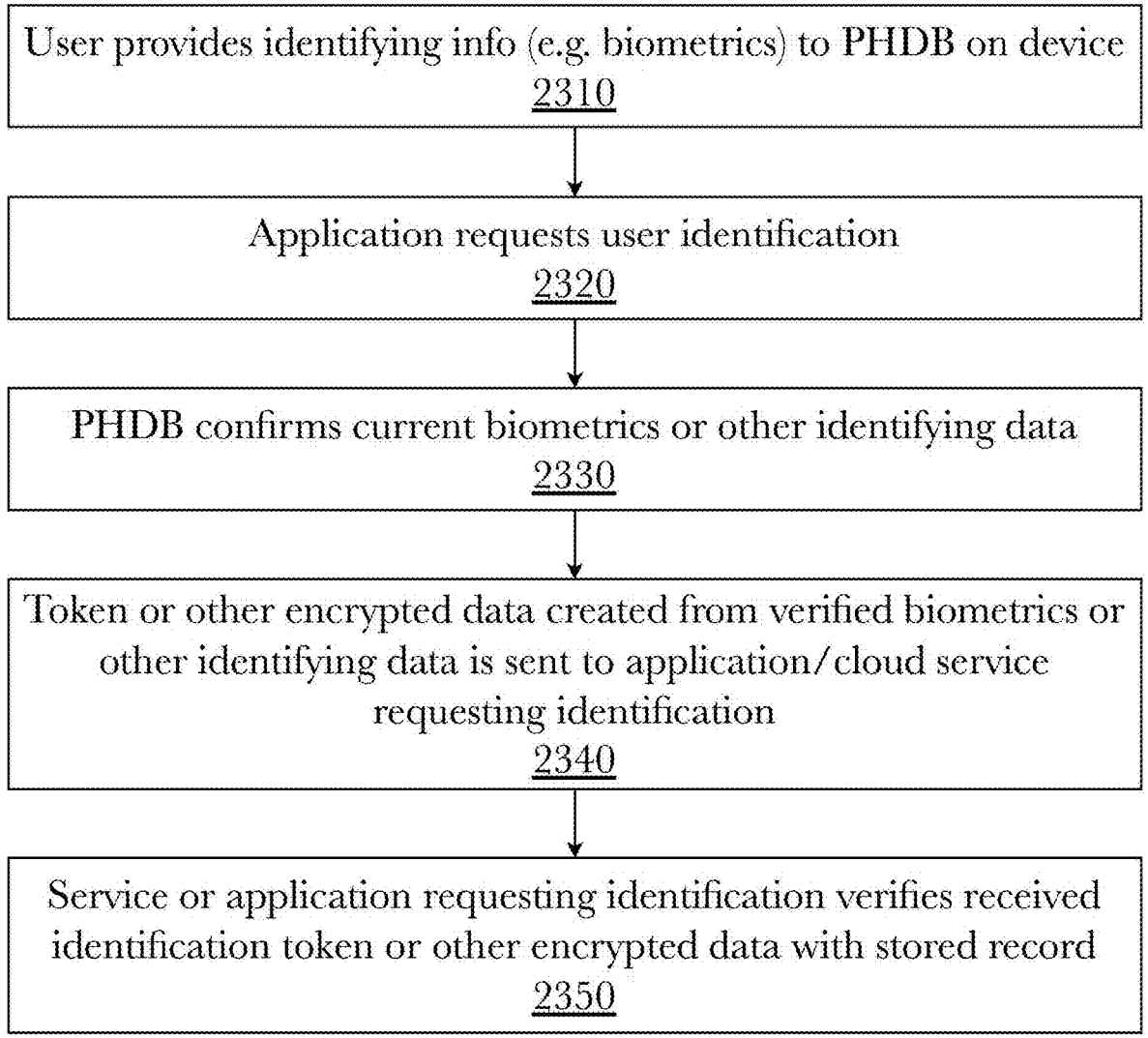
FIG. 23 is a method diagram showing exemplary steps taken for a user to authenticate themselves for other services using a PHDB, according to an aspect of the invention.

FIG. 23 is a method diagram showing exemplary steps taken for a user to authenticate themselves for access to cloud-based services using a PHDB, according to an aspect of the invention. According to the aspect, the authentication process begins at step 2310 when the user provides identifying info (e.g. biometrics) to PHDB on device 2310. The provided biometric data may be obtained from sensors/systems embedded in a PHDB-enabled mobile device 110*a-n* or from stand-alone biometric devices which can collect and transmit biometric data and may be integrated with a mobile device 110*a-n* or other computing device 115*a-n*.

When an external application requests user identification 2320, the PHDB is prompted to confirm the current biometrics or other identifying data associated with the user 2330. In an embodiment, biometric computing 800 may be leveraged to verify a user's identity using biometric data as a form of authentication. Biometric computing 800 can receive the user's provided identifying info, biometric data, and compare it to stored biometric templates to verify the identity of the user attempting to access the cloud-based services.

Following confirmation, at step 2340 a token or other encrypted data, derived from the verified biometrics or identifying data, is generated, and sent to the application/cloud service requesting identification. This token serves as a secure and privacy preserving means of verifying the user's identity. The service or application receiving the identification token verifies it by comparing it with stored records at step 2350. This verification process ensures that the user's identity is authenticated based on the information stored in the PHDB, without the need to expose sensitive biometric data directly.

Figure 24:
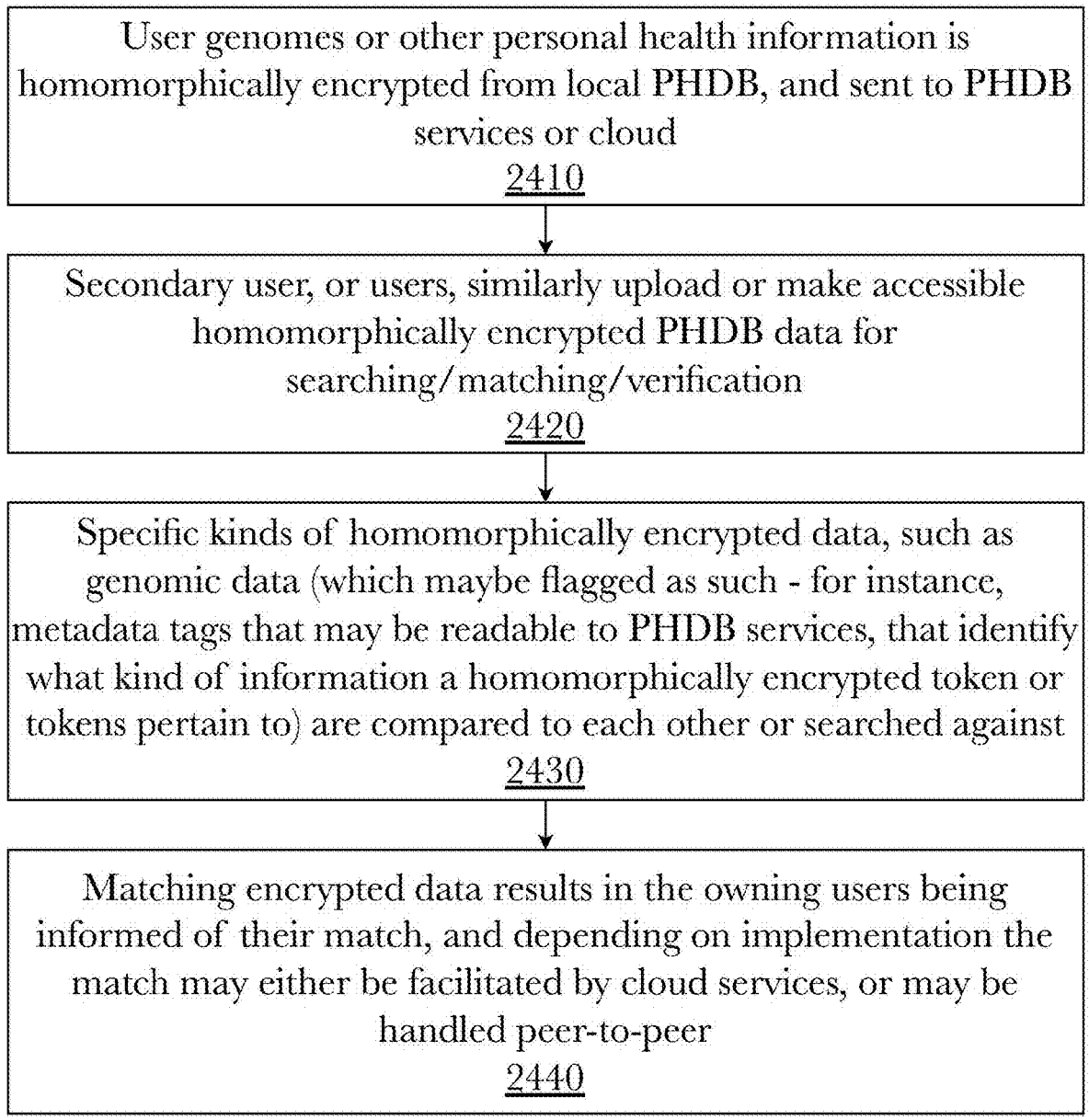
FIG. 24 is a method diagram showing exemplary steps taken for genome screening of a pair of individuals using their PHDBs, according to an aspect of the invention.

FIG. 24 is a method diagram showing exemplary steps taken for genome screening of a pair of individuals using their PHDBs, according to an aspect of the invention. According to the aspect, the process begins at step 2410 when the user genomic or other personal health information is homomorphically encrypted from their local PHDB and sent to PHDB services or cloud. Simultaneously, a secondary user, or multiple users, upload or make accessible homomorphically encrypted PHDB data for searching, matching, or verification 2420. All users can adjust access controls and permission for sharing with respect to the data stored in their PHDB. One such selection may be allowing other PHDB system users to perform homomorphic comparisons or other analysis of homomorphically encrypted data.

Specific kinds of homomorphically encrypted data, such as genomic data (which may be flagged as such—for instance, via metadata tags that may be readable to PHDB services, identifying what kind of information a homomorphically encrypted token or tokens pertain to), are then compared to each other or searched against 2430. Matching encrypted data results in the owning users being informed of their match. Depending on implementation, the match may either be facilitated by cloud services or handled peer-to-peer 2440. This process allows users to be notified of potentially significant genomic matches while preserving the security and privacy of their sensitive health information.

Figure 25:
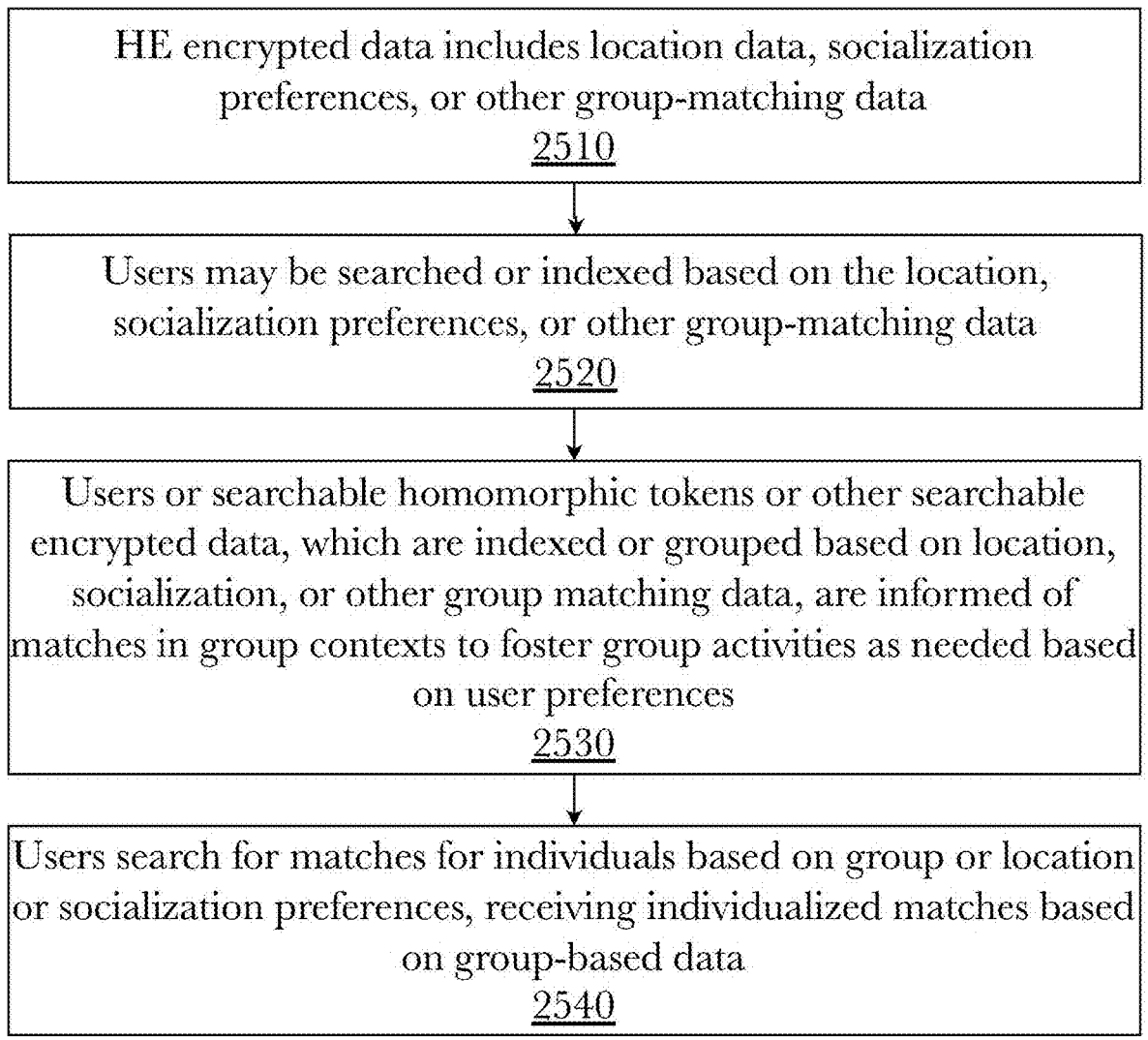
FIG. 25 is a method diagram showing exemplary steps taken for groups to be formed and users to be screened based on their group memberships via their PHDBs, according to an aspect of the invention.

FIG. 25 is a method diagram showing exemplary steps taken for groups to be formed and users to be screened based on their group memberships via their PHDBs, according to an aspect of the invention. According to the aspect, the process begins at step 2510 when the PHDB system homomorphically encrypts (HE) data, including location data, socialization preferences, or other group-matching data. Users may be searched or indexed based on the location, socialization preferences, or other group-matching data 2520. The system may implement a database or indexing system to store and organize user data, ensuring that the indexing system can efficiently query and retrieve data based on different criteria, such as location or socialization preferences. In some implementations, a database with geospatial indexing capabilities may be utilized to facilitate location-based search.

According to an aspect of an embodiment, groups may be declaratively assigned wherein an individual can declare which groups they belong to (e.g., I am a veteran or member of this school or church, etc.). It should be appreciated that groups may be physical emergent groups and emergent digital groups. Physical emergent groups are groups that form in physical, real-world environments, such as communities, workplaces, or social gatherings. Physical emergent groups often arise spontaneously based on shared interests, needs, or circumstances. For example, a group of neighbors coming together to address a local issue would be considered a physical emergent group. Digital emergent groups are groups that form in digital or online environments, such as social media platforms, online forums, or multiplayer online games. Digital emergent groups can form around common interests, hobbies, or goals, and they often transcend geographical boundaries. For example, a group of individuals organizing a fundraiser on a crowdfunding platform would be considered a digital emergent group. Both types of groups can exhibit emergent properties, meaning that the group as a whole displays characteristics or behaviors that are not exhibited by any individual member. These properties can arise from the interactions and dynamics within the group, making them more than the sum of their parts. By analyzing these declared and emergent groups, the platform 120 can aid with broader association issues that can impact longevity factors for physical and mental fitness where long term data is needed (e.g., Alzheimer's).

At a next step 2530 users or searchable homomorphic tokens, and other searchable encrypted data, which are indexed or grouped based on location, socialization, or other group matching data, are informed of matching data, are informed of matches in group contexts. This fosters group activities as needed based on user preferences. For example, an individual may be seeking other people to play a VR-based video game with and may also be seeking opportunities to meet up with these other people for socialization outside of the VR video game. In such a use case, the individuals may be matched based on socialization preferences related to AR/VR gaming and may be further matched based on proximity to the individual who was seeking out the group.

Users can search for matches for individuals based on group, location, or socialization preferences and receive individualized matches based on group-based data at step 2540. That is to say, that given a matched group of people, users can then search for individual matches selected from the population of the matched group. These individual matches may be based on the group-based data and may not include other user preference data.

Figure 26:
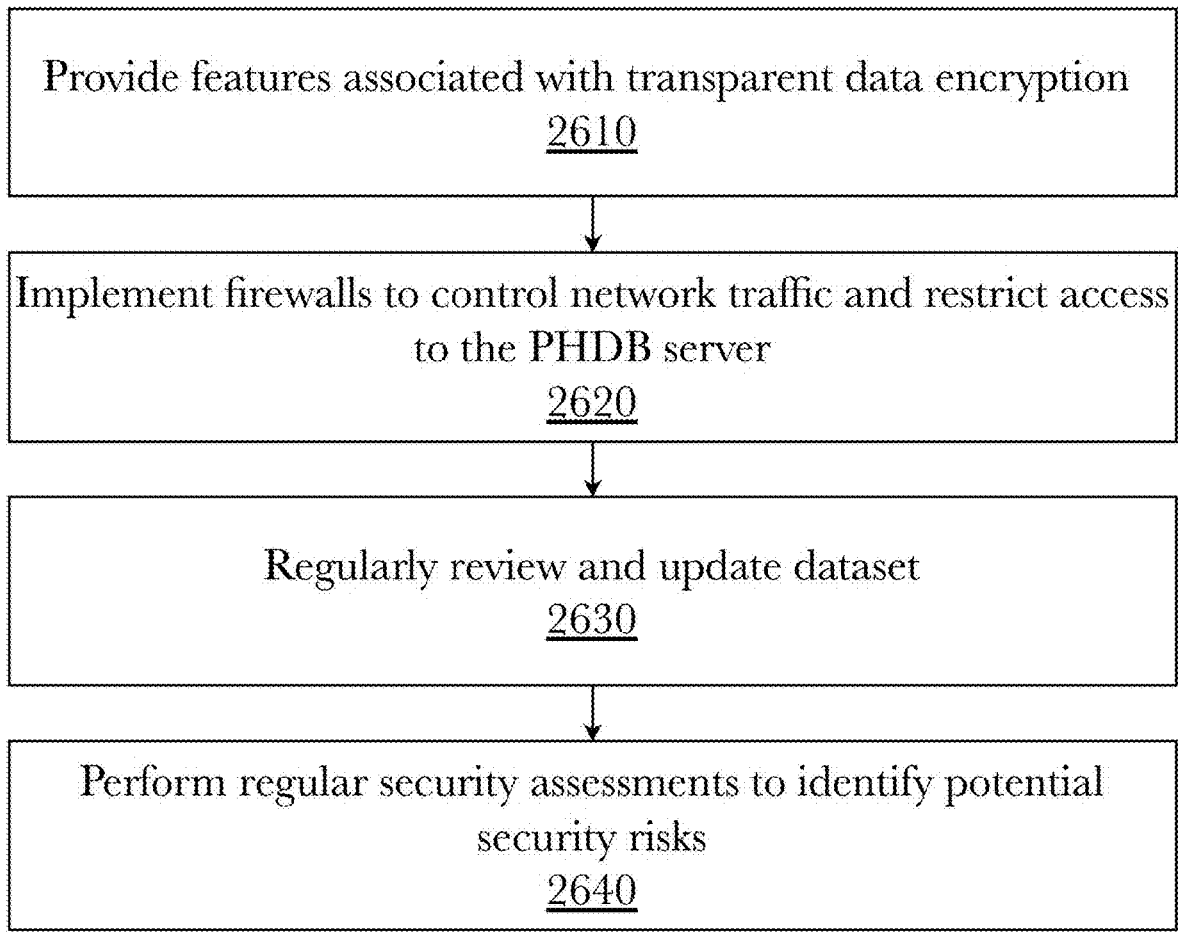
FIG. 26 is a method diagram showing exemplary steps taken on an Oracle database to mitigate the risk of exploitation.

FIG. 26 is a method diagram showing exemplary steps taken on a oracle database to mitigate the risk of exploitation. According to an embodiment, the process utilizes homomorphic encryption for sensitive data, both in the cloud and at rest. Oracle provides features such as transparent data encryption for securing data as the database level 2610. Implement firewalls to control network traffic and restrict access to the personal health database server 2620. The oracle dataset can be regularly reviewed and updated to ensure that in the event of a security incident, the data can quickly be recovered 2630. Regular security assessments will be conducted, including penetration testing and vulnerability scanning to identify and address potential weaknesses in the oracle environment 2640.

Figure 27:
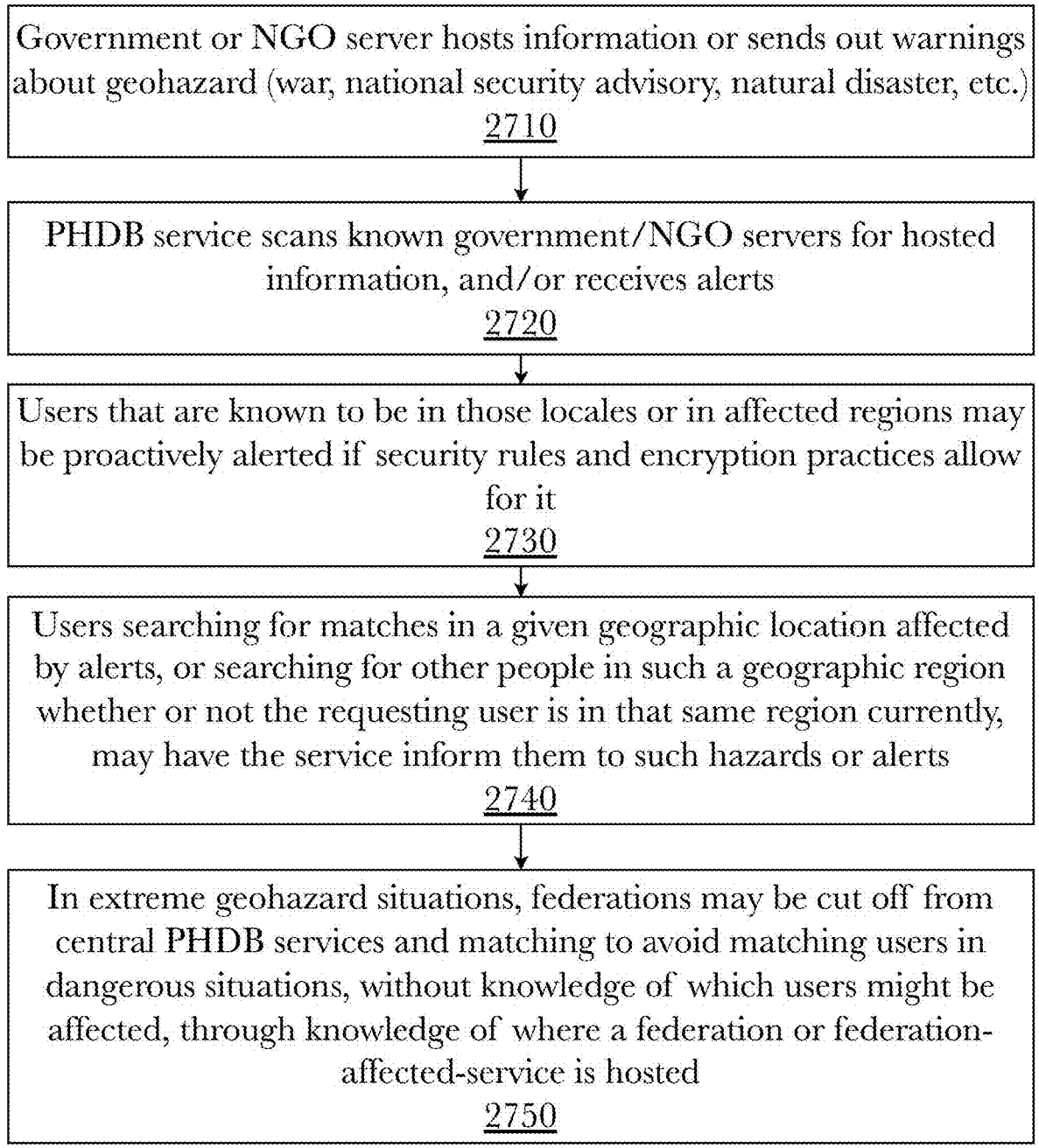
FIG. 27 is a method diagram showing exemplary steps taken for a PHDB service to alert or warn users based on geohazards and government or NGO alerts based on geographical regions, according to an aspect of the invention.

FIG. 27 is a method diagram showing exemplary steps taken for a PHDB service to alert or warn users based on geohazards and government or NGO alerts based on geographical regions, according to an aspect of the invention. According to the aspect, the process begins at step 2710 when a government or NGO server hosts information or sends out warnings about geohazard (war, national security advisory, natural disaster, etc.). The PHDB service 101 scans known government/NGO servers for hosted information, and/or receives alerts directly at step 2720. Users that are known to be in those locales or in affected regions may be proactively alerted, contingent upon security rules and encryption practices at step 2730. This proactive alerting ensures that users with potential exposure to geohazards are promptly informed, enhancing their situational awareness and safety.

According to some aspects, historic geolocation data may be used to cross reference known environmental hazards as it relates to subsequent potential health implications outside of alerts. Similar to how the Dept. of Veterans Affairs retroactively declared burn pit exposure for anyone deployed to a specific location or area. This could be extended to known oil spill areas, for example, or water quality issues (i.e., Flint, Michigan) where there is no "official" alert, but there was a known environmental event (e.g., oil spill in the gulf). Modeling and simulation may then be used to discover seemingly unrelated health issues. For example, would modeling the fluid dynamics around the use of Corexit 9527A (known to contain toxics harmful to red blood cells) in the Gulf turn up long term health impacts when combined with data from PHDB? Adding second and third order effects into the modeling would be possible (e.g., health issues related to dispersant impact of fish that were consumed). Such a system may be used to compare environmental exposure to fertility issues and make recommendations.

Users searching for matches in a given geographic location affected by alerts or searching for other people in such a geographic region, whether or not the requesting user is in that same region currently, may have the service inform them to such hazards or alerts at step 2740. This ensures that users actively seeking connections or information in specific regions are made aware of potential risks. In extreme geohazard situations, in an optional step 2750 federations may be cut off from central PHDB services and matching to avoid matching users in dangerous situations. This is done without specific knowledge of which users might be affected, through knowledge of where a federation or federation-affected-service is hosted. This proactive disconnection ensures the safety of users during critical situations.

According to some embodiments, if may be possible for different consortiums of individuals to share data related to their exposure to geohazards and/or environmental hazards with limited context specifications (e.g., a potential group of litigants for a chemical lawsuit or a group of concerned parents). In a use case, individuals in a consortium may opt-in to marketing pools and/or subscriptions (e.g., expert content like relevant journal papers on select omics elements referencing a subscriptions groups' characteristics). In another use case, consider citizens in the U.S. who get healthcare in another country or on a cruise where subsets of records may be more appropriate for sharing for limited time and/or utility.

It should be appreciated that individual users may select which of their data they can share with an NGO or governmental entity. It should be further appreciated that a "regulatory compliance" locker may be supported by platform 120 for records needed to be kept for liability and professional responsibility reasons but where the data is encrypted w/a key that is not available to healthcare providers in that system or office.

Figure 28:
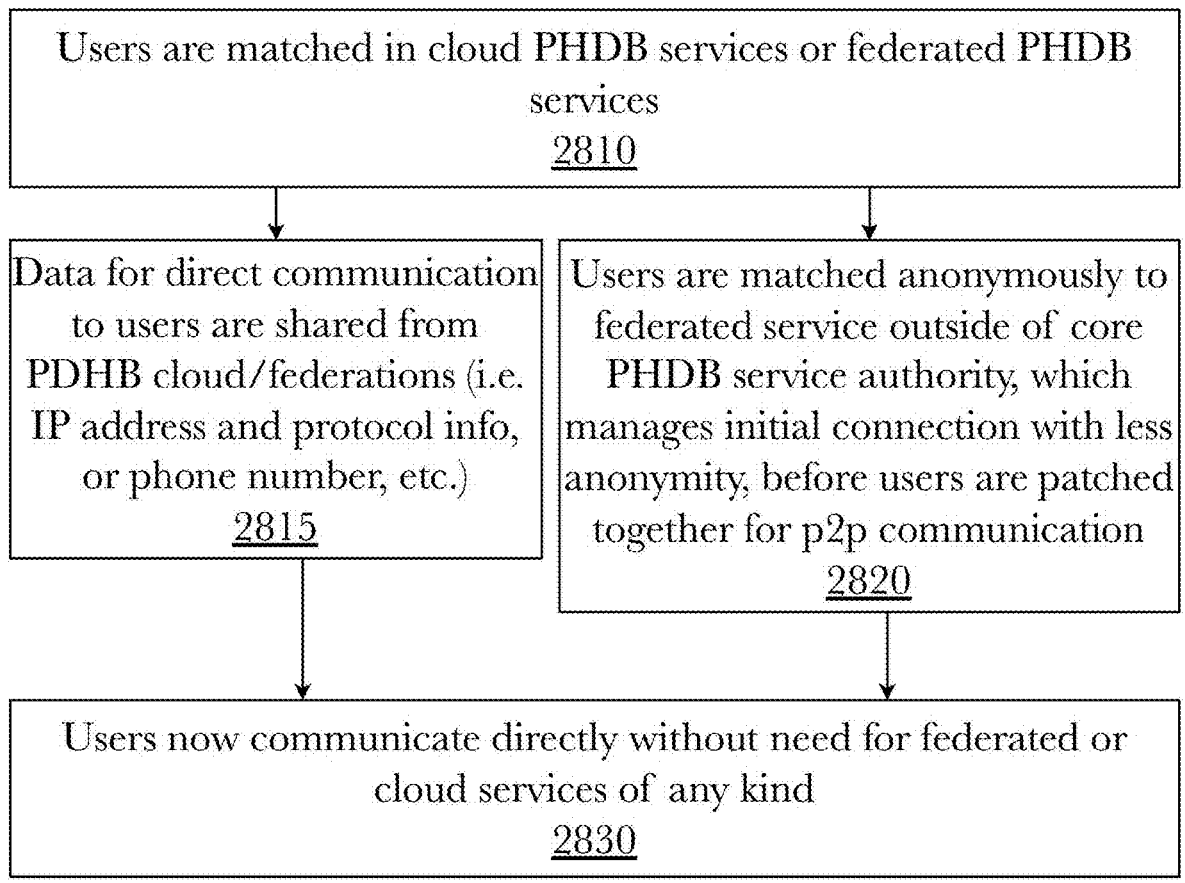
FIG. 28 is a method diagram showing exemplary steps taken for PHDB platform users to be paired for peer-to-peer communications, according to an aspect of the invention.

FIG. 28 is a method diagram showing exemplary steps taken for PHDB platform users to be paired for peer-to-peer communications, according to an aspect of the invention. According to the aspect, the process begins at step 2810 as users are matched in cloud PHDB services or federated PHDB services. Data for direct communication to users are shared from PDHB cloud/federations (i.e. IP address and protocol info, or phone number, etc.) 2815. Additionally, or alternatively, users are then matched anonymously to federated services outside of the core PHDB service authority. This federated service manages initial connection with less anonymity before users are seamlessly patched together for peer-to-peer communication at step 2820. Once the users are matched, they can communicate directly without need for federated or cloud services of any kind 2830. This enables users to establish direct and private communications, enhancing the efficiency and privacy of their interactions.

Figure 29:
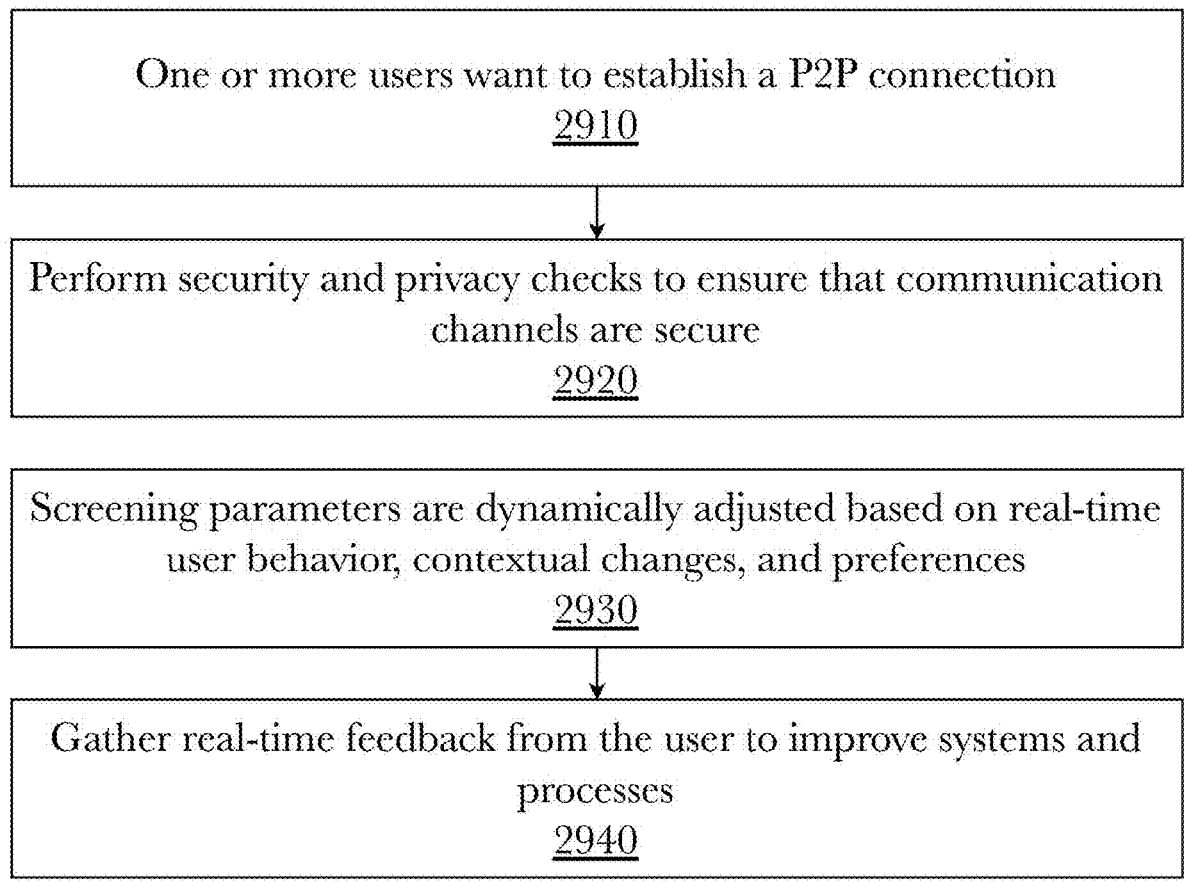
FIG. 29 is a method diagram showing exemplary steps taken for a pair of users to be screened for peer-to-peer communications, according to an aspect of the invention.

FIG. 29 is a method diagram showing exemplary steps taken for a pair of users to be screened for peer-to-peer communications, according to an aspect of the invention. According to the aspect, the process begins at step 2910 as one or both users express an interest in peer-to-peer communications. This may be done through a user interface provided by PHDB application 111*a* stored and operated on a PHDB-enabled mobile device or on some other computing device 115*a*, wherein the user interface can provide a means for one or two users can indicate their preferences and interests via PHDB. At step 2920, before establishing the peer-to-peer connection, the system will conduct security and privacy checks to ensure that communication channels are secure and user privacy is maintained throughout the interaction. This may involve verifying user identities (e.g., two-factor authentication, biometric authentication, token-based authentication, etc.), encrypting communication channels, and implementing access control measures (which may be specified by the user or by PHDB-related services)

At step 2930 the screening parameters are dynamically adjusted based on real-time user behavior, contextual changes, and any evolving preferences. The adaptive approach enhances the accuracy of the screening process. To facilitate dynamic screening the system may use machine learning algorithms to analyze user behavior and detect patterns that indicate the likelihood of malicious activity or inappropriate behavior. For example, the system can analyze the frequency and timing of messages, the content of messages, and the history of interactions. Furthermore, the system can take into account contextual information such as user preferences, location, and device information to adapt screening parameters. For example, the system might adjust screening parameters based on whether the user is accessing the system from a trusted location or device.

In an implementation, the system may provide functionality directed to real-time user behavior detection. This can include monitoring user interactions and events in real-time to detect patterns of behavior. This could include monitoring mouse movements, keyboard inputs, screen tapping/swiping/touching, and other user actions. In an embodiment, the system may use machine learning models to detect anomalies or patterns in user behavior that may indicate malicious activity. These models could be trained using labeled data to improve their accuracy. In an aspect, the system may create user profiles based on historical behavior and use these profiles to detect deviations from normal behavior. For example, if a user suddenly starts sending a large number of messages, this could be flagged as suspicious behavior.

As a last step 2940, during and after peer-to-peer communication, the system gathers real-time feedback from users. The feedback loop contributes to the continuous improvement of the screening algorithms, ensuring an optimized user experience.

Figure 30:
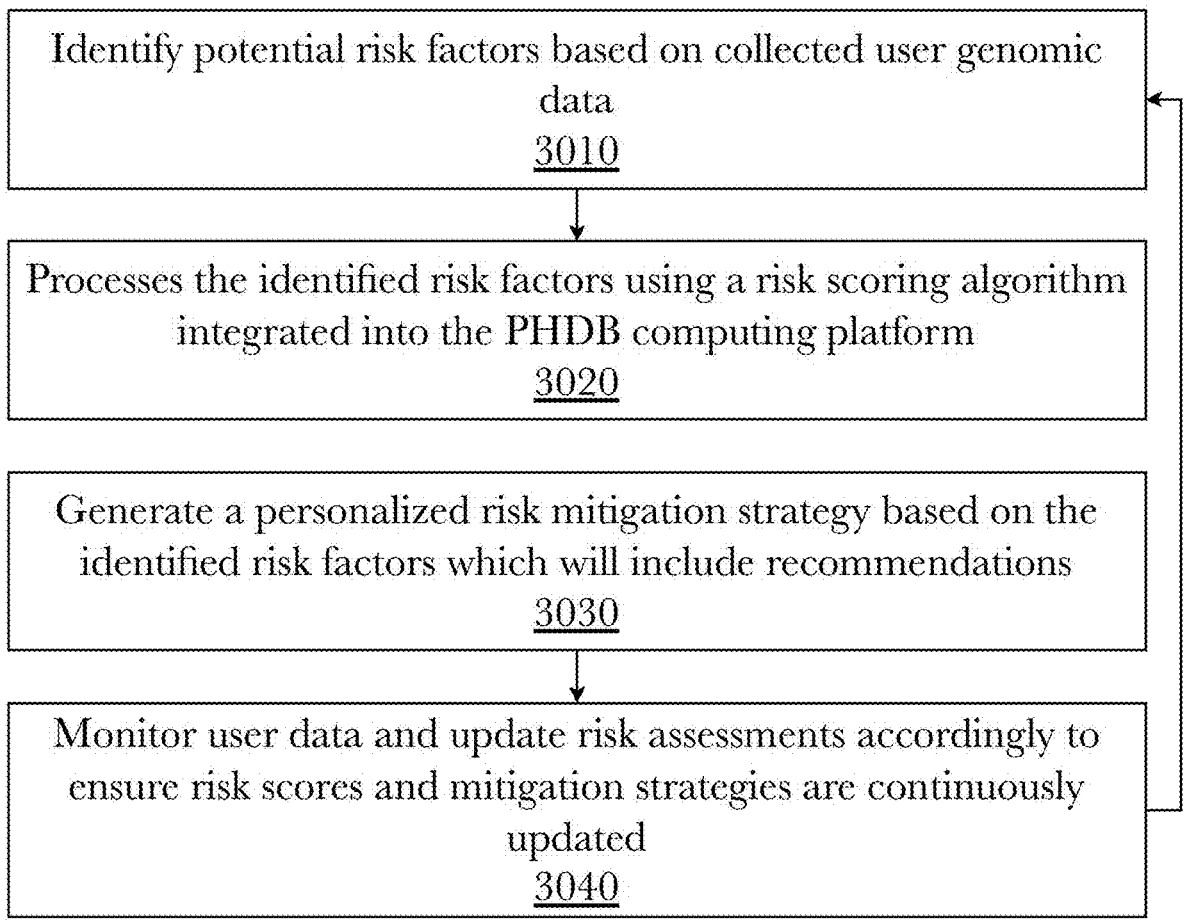
FIG. 30 is a method diagram showing exemplary steps taken for individuals to be screened and scored for risk and risk mitigation factors using their PHDB and the PHDB computing platform, according to an aspect of the invention.

FIG. 30 is a method diagram showing exemplary steps taken for individuals to be screened and scored for risk and risk mitigation factors using their PHDB and the PHDB computing platform, according to an aspect of the invention. According to the aspect, the process begins at step 3010 when PHDB system identifies potential risk factors based on the collected user genomic data, which can span a range of health-related aspects, for example whether both the person who contributes the egg and the one who provides the sperm carries variants within the same gene to give rise to a child with cystic fibrosis, spinal muscular atrophy, sickle cell disease, and Tay-Sachs. The risk-factors may be chosen based on user defined preferences or other input or data that is derived or inferred from analysis of a plurality of PHDB data. These could include genetic variation associated with certain diseases or conditions. For example, a user can screen for a specific genetic disorder, phenotypic expression, behavioral condition, or any other preference relevant to the type of search/match being performed.

At a next step 3020 the identified risk factors can be processed by a risk scoring algorithm that can may be integrated into the PHDB computing platform 120. Such a scoring algorithm may be developed and deployed using machine learning engine 1510. The scoring algorithm can be trained to assign scores to each risk factor considering the weight of each risk 3020. A weight may be assigned to each risk factor based on its importance or relevance to the risk being assessed. The weight could be based on scientific evidence, expert opinion, or other relevant factors. The weights may be assigned by a developer of the scoring algorithm, or the weights may be a learned feature of the scoring model itself. For example, a neural network may be developed to generate as output a plurality of risk scores for various identified risk factors, wherein the neural network learns to assign weights to each risk factor based on continuous learning on a large data corpus. The scoring algorithm may be validated, for example, using independent datasets or clinical studies to ensure its accuracy and reliability. In some implementations, feedback from domain experts (e.g., clinical psychologists, physicians, etc.) may be used to improve the scoring algorithms performance and fitness.

In some implementations, genomic data may be collected from users, such as whole genome sequencing or whole exome sequencing data, depending on the scope of the analysis. The genomic data may be analyzed to identify relevant genetic variations or mutations associated with identified risk factors. The scoring algorithm may, for each risk factor, calculate a risk score based on the presence or absence of the genetic variation or mutation associated with that risk factor. The score could be binary (0 or 1) or based on a scale, depending on the nature of the risk factor and the embodiment of the system. The system may then calculate a weighted sum of the risk scores for all the risk factors, using the weights assigned to each risk factor. This yields an overall risk score for the individual. In various embodiments, users or PHDB services may define threshold for the risk scores to categorize individuals into different risk categories (e.g., low, medium, high).

Additionally, the system may be configured to provide interpretation guidelines to help users understand their risk level and any recommended actions based on their risk score. At step 3030 the system generates a personalized risk mitigation strategy based on the identified risk factors (and risk score) which can include recommendations, for example, whether two users would be genetically compatible. For genetic compatibility between users, this could involve comparing genetic data to assess the likelihood of genetic compatibility and providing recommendations based on the results. The system may also take into account other factors that may impact risk mitigation recommendations, such as lifestyle factors, medical history, and environmental factors. Exemplary recommendations can include lifestyle changes, medical interventions, or genetic counseling. In at least one implementation, an LLM may be developed to receive an input comprising at least a set of identified risk factors and a risk score for one or more individuals and to generate as output a risk mitigation strategy.

At step 3040 the system continuously monitors user data and updates risk assessments accordingly to ensure risk scores and mitigation strategies are continuously updated to reflect current data. When new user data is discovered (e.g., a user has updated the personal information in their PHDB) the process may loop back to step 3010 wherein new potential risk factors may be identified based on the updated user data. The process then repeats, and a new risk score and risk mitigation strategy is created.

Figure 31:
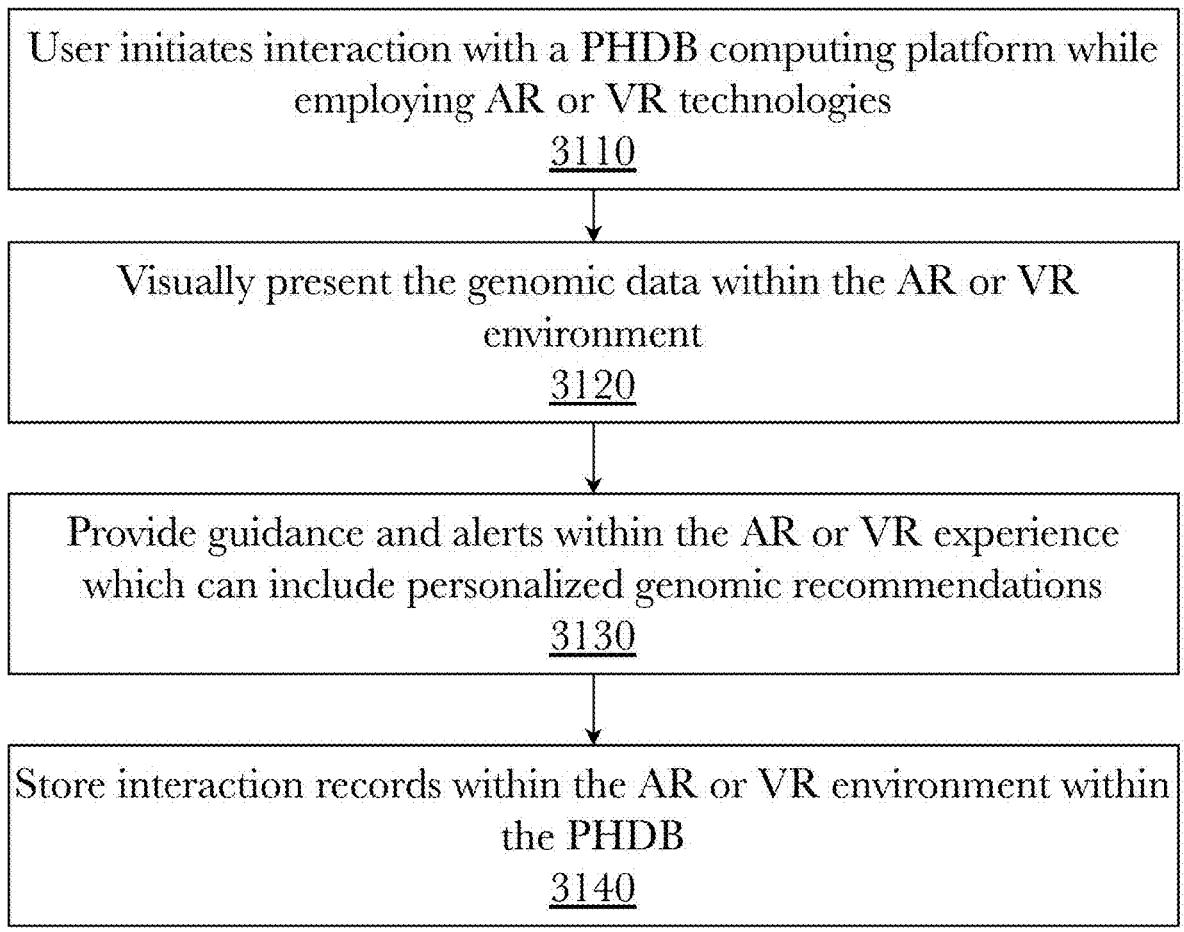
FIG. 31 is a method diagram showing exemplary steps taken for a PHDB computing platform to be utilized alongside AR or VR technologies, according to an aspect of the invention.

FIG. 31 is a method diagram showing exemplary steps taken for a PHDB computing platform to be utilized alongside AR or VR technologies, according to an aspect of the invention. According to the aspect, the process begins at step 3110 when a user initiates interaction with the PHDB computing platform 120 while employing AR or VR technologies. Initiation can occur through voice commands, gestures, or other AR/VR input methods. At step 3120 genomic data is visually presented within the AR or VR environment. This can include immersive visualizations of genomic metrics such as scanning another user that has opted into the genomic screening and them turning a color, for example, green for being clear with no issues and turning red if chances are there is not genetic compatibility.

At step 3130 PHDB computing platform provides guidance and alerts within the AR or VR experience which can include personalized genomic recommendations 3130. For example, in an augmented reality environment, PHDB computing platform 120 can overlay a virtual path which leads to a screened, genetically compatible user. Multiple paths may be overlayed, and color coordinated to indicate relative strengths of compatibility or some other matched factor. For example, a hot-cold scheme could be used wherein "cold" (low compatibility) paths may be indicated in a dark shade of blue, "hot" (high compatibility) paths may be indicated in a bright shade of red, and the range of compatibilities between low and high may be represented as color gradient shifting from dark blue to bright red. Guidance and alerts may be text-based and also displayed in the AR/VR environment As a last step 3140 interaction records within the AR or VR environment will be stored within the PHDB to ensure a comprehensive record of the user's health-related AR or VR interactions.

Figure 32:
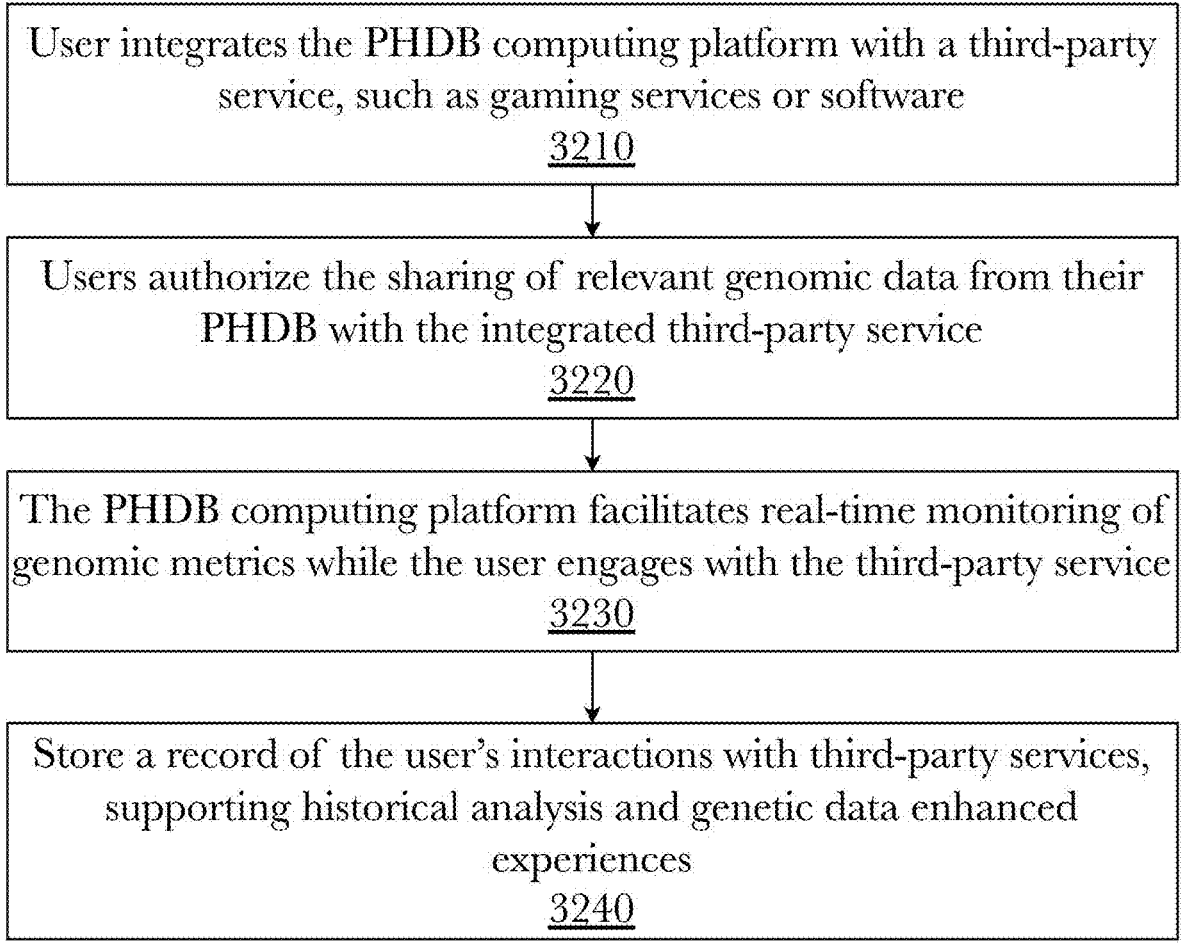
FIG. 32 is a method diagram showing exemplary steps taken for a PHDB computing platform to be used in tandem with third party services such as gaming services or software, according to an aspect of the invention.

FIG. 32 is a method diagram showing exemplary steps taken for a PHDB computing platform to be used in tandem with third party services such as gaming services or software, according to an aspect of the invention. According to the aspect, the process begins at step 3210 when a user integrates the PHDB computing platform with a third-party service, such as gaming services or software. The integration can be initiated through user preferences, app settings, or dedicated integration features. Users may authorize the sharing of relevant genomic data (or other personal information) from their PHDB with the integrated third-party service at step 3220. To ensure that only authorized devices or users can access the data, integrated third-party services can use authentication and authorization mechanisms. This can include using digital certificates, passwords, or biometric authentication. The PHDB computing platform facilitates real-time monitoring of genomic metrics while the user engages with the third-party service at step 3230. This can include adaptive gameplay based on real-time genetic and health data, personalized challenges, or dynamic content tailored to the user's genetic profile. At step 3240 interaction records and data integration details are stored within the PHDB. This ensures a comprehensive record of the user's interactions with third-party services, supporting historical analysis and genetic data enhanced experiences.

Figure 33:
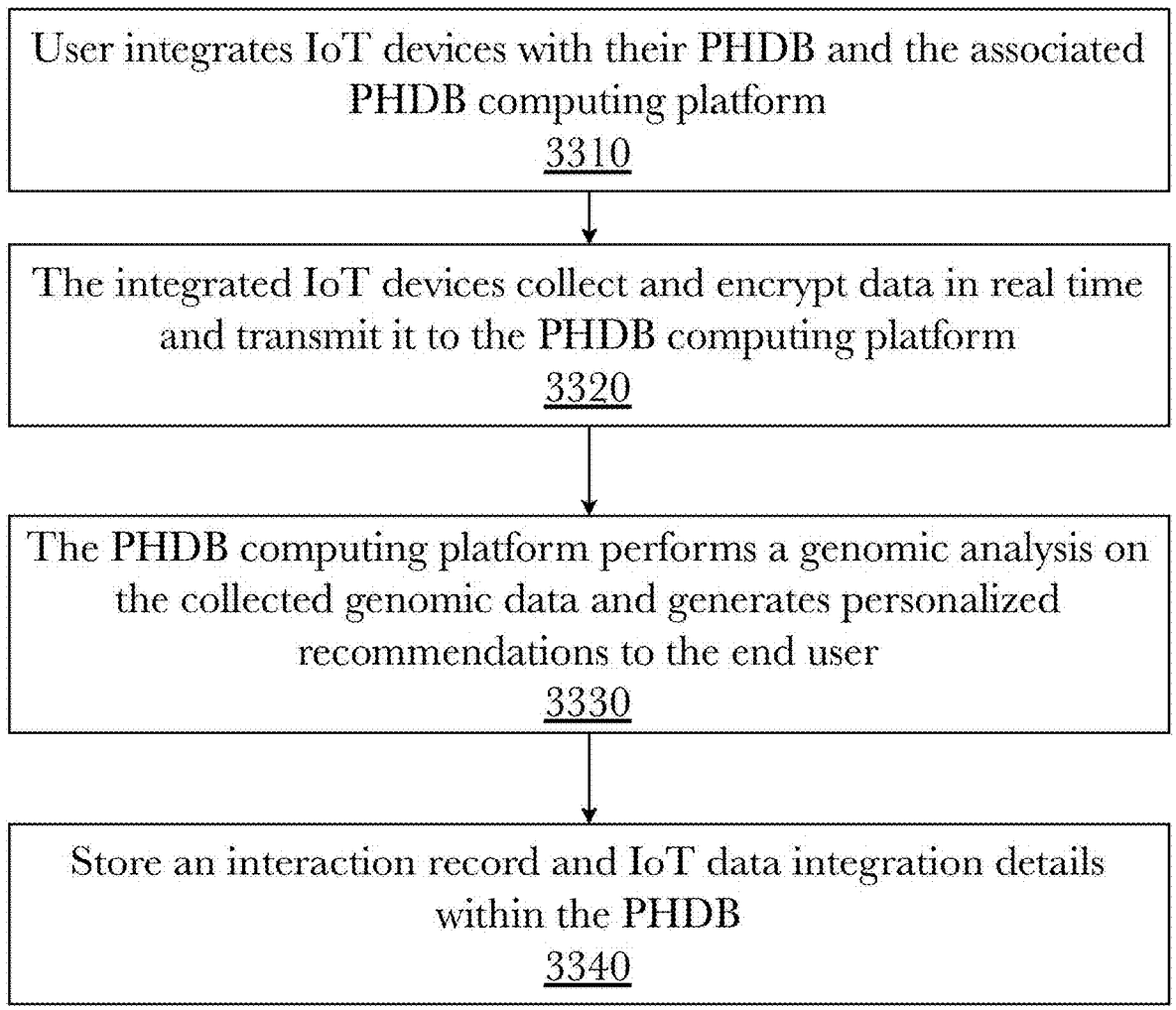
FIG. 33 is a method diagram showing exemplary steps taken for a user to enhance their diet by utilizing IoT devices with their PHDB and a PHDB computing platform, according to an aspect of the invention.

FIG. 33 is a method diagram showing exemplary steps taken for a user to integrate a plurality of IoT devices with their PHDB and a PHDB computing platform, according to an aspect of the invention. According to the aspect, the process begins at step 3310 when a user integrates IoT devices with their PHDB and the associated PHDB computing platform. The integration can be initiated through user preferences, app settings, or dedicated integration features. IoT devices may include smart kitchen appliances, wearables, or other connected devices capable of tracking information. IoT devices capture data using sensors or other data collection mechanisms. This data can include sensor readings, device status information, environmental data, and more. The integrated IoT devices may be configured to collect and encrypt data in real time and the data is transmitted to the PHDB computing platform at step 3320. Before encryption, data may undergo preprocessing to clean, filter, or format it for further processing or storage. Once the data is ready, it is encrypted to protect it from unauthorized access. There are several encryption techniques that can be used, including symmetric encryption and asymmetric encryption. For data transmission over networks, IoT devices can use TLS (transport layer security) to encrypt data in transit. TLS ensures that data is encrypted between the IoT device and the server or other devices it communicates with. To ensure that only authorized devices or users can access the data, IoT devices can use authentication and authorization mechanisms. This can include using digital certificates, passwords, or biometric authentication. The IoT devices may be configured to collect, encrypt, and transmit genomic data. The PHDB computing platform 120 performs a genomic analysis on the collected genomic data and generates personalized recommendations to the end user at step 3330. At step 3340 the system may store an interaction record and IoT data integration details within the PHDB to ensure a comprehensive record of the user's genetic information, IoT device interactions, and health-related insights.

Exemplary Computing Environment

Figure 34:
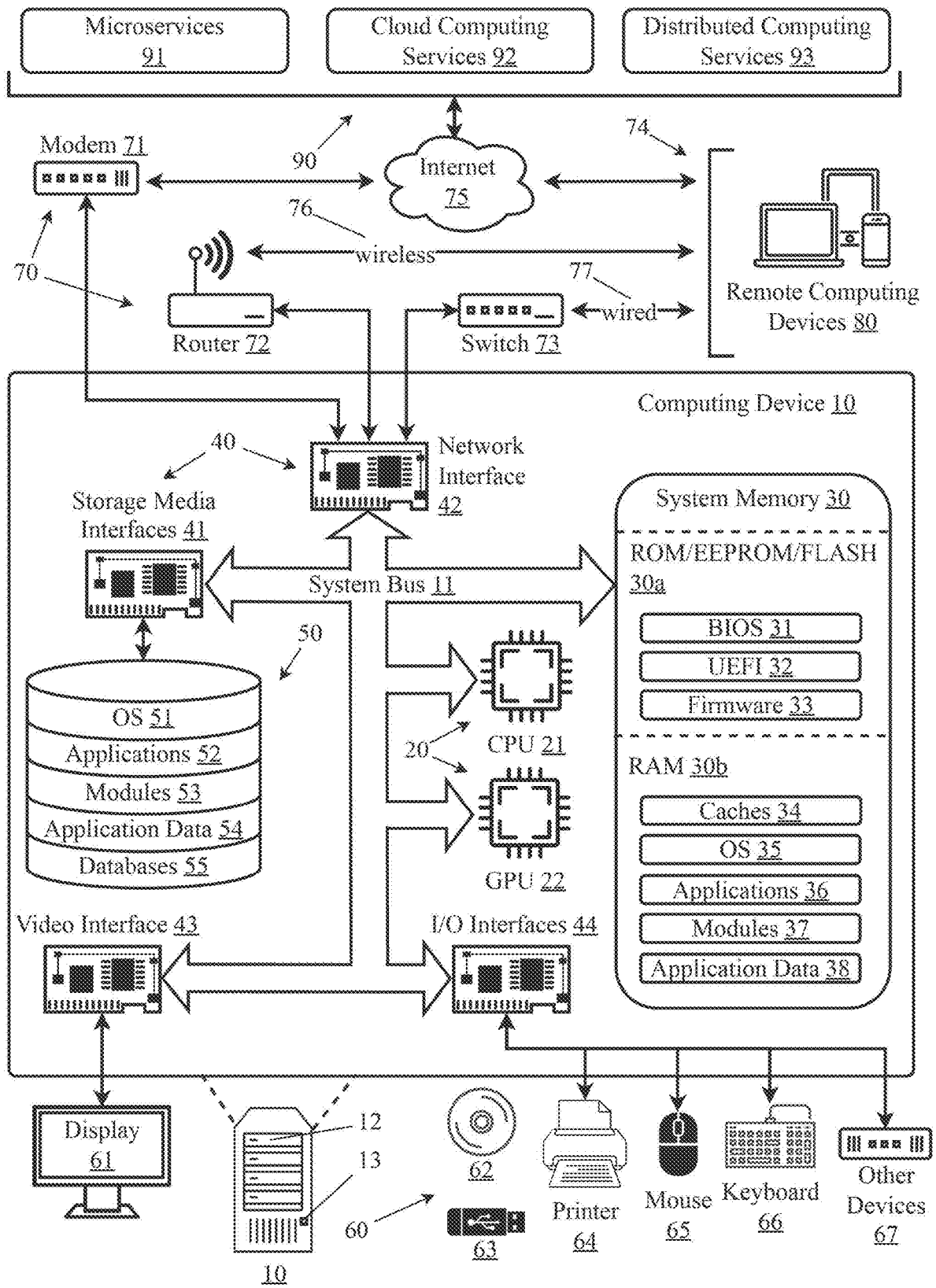
FIG. 34 illustrates an exemplary computing environment on which an embodiment described herein may be implemented.

FIG. 34 illustrates an exemplary computing environment on which an embodiment described herein may be implemented, in full or in part. This exemplary computing environment describes computer-related components and processes supporting enabling disclosure of computer-implemented embodiments. Inclusion in this exemplary computing environment of well-known processes and computer components, if any, is not a suggestion or admission that any embodiment is no more than an aggregation of such processes or components. Rather, implementation of an embodiment using processes and components described in this exemplary computing environment will involve programming or configuration of such processes and components resulting in a machine specially programmed or configured for such implementation. The exemplary computing environment described herein is only one example of such an environment and other configurations of the components and processes are possible, including other relationships between and among components, and/or absence of some processes or components described. Further, the exemplary computing environment described herein is not intended to suggest any limitation as to the scope of use or functionality of any embodiment implemented, in whole or in part, on components or processes described herein.

The exemplary computing environment described herein comprises a computing device 10 (further comprising a system bus 11, one or more processors 20, a system memory 30, one or more interfaces 40, one or more non-volatile data storage devices 50), external peripherals and accessories 60, external communication devices 70, remote computing devices 80, and cloud-based services 90.

System bus 11 couples the various system components, coordinating operation of and data transmission between those various system components. System bus 11 represents one or more of any type or combination of types of wired or wireless bus structures including, but not limited to, memory busses or memory controllers, point-to-point connections, switching fabrics, peripheral busses, accelerated graphics ports, and local busses using any of a variety of bus architectures. By way of example, such architectures include, but are not limited to, Industry Standard Architecture (ISA) busses, Micro Channel Architecture (MCA) busses, Enhanced ISA (EISA) busses, Video Electronics Standards Association (VESA) local busses, a Peripheral Component Interconnects (PCI) busses also known as a Mezzanine busses, or any selection of, or combination of, such busses. Depending on the specific physical implementation, one or more of the processors 20, system memory 30 and other components of the computing device 10 can be physically co-located or integrated into a single physical component, such as on a single chip. In such a case, some or all of system bus 11 can be electrical pathways within a single chip structure.

Computing device may further comprise externally-accessible data input and storage devices 12 such as compact disc read-only memory (CD-ROM) drives, digital versatile discs (DVD), or other optical disc storage for reading and/or writing optical discs 62; magnetic cassettes, magnetic tape, magnetic disk storage, or other magnetic storage devices; or any other medium which can be used to store the desired content and which can be accessed by the computing device 10. Computing device may further comprise externally accessible data ports or connections 12 such as serial ports, parallel ports, universal serial bus (USB) ports, and infrared ports and/or transmitter/receivers. Computing device may further comprise hardware for wireless communication with external devices such as IEEE 1394 ("Firewire") interfaces, IEEE 802.11 wireless interfaces, BLUETOOTH® wireless interfaces, and so forth. Such ports and interfaces may be used to connect any number of external peripherals and accessories 60 such as visual displays, monitors, and touch-sensitive screens 61, USB solid state memory data storage drives (commonly known as "flash drives" or "thumb drives") 63, printers 64, pointers and manipulators such as mice 65, keyboards 66, and other devices 67 such as joysticks and gaming pads, touchpads, additional displays and monitors, and external hard drives (whether solid state or disc-based), microphones, speakers, cameras, and optical scanners.

Processors 20 are logic circuitry capable of receiving programming instructions and processing (or executing) those instructions to perform computer operations such as retrieving data, storing data, and performing mathematical calculations. Processors 20 are not limited by the materials from which they are formed or the processing mechanisms employed therein, but are typically comprised of semiconductor materials into which many transistors are formed together into logic gates on a chip (i.e., an integrated circuit or IC). The term processor includes any device capable of receiving and processing instructions including, but not limited to, processors operating on the basis of quantum computing, optical computing, mechanical computing (e.g., using nanotechnology entities to transfer data), and so forth. Depending on configuration, computing device 10 may comprise more than one processor. For example, computing device 10 may comprise one or more central processing units (CPUs) 21, each of which itself has multiple processors or multiple processing cores, each capable of independently or semi-independently processing programming instructions. Further, computing device 10 may comprise one or more specialized processors such as a graphics processing unit (GPU) 22 configured to accelerate processing of computer graphics and images via a large array of specialized processing cores arranged in parallel.

System memory 30 is processor-accessible data storage in the form of volatile and/or nonvolatile memory. System memory 30 may be either or both of two types: non-volatile memory and volatile memory. Non-volatile memory 30a is not erased when power to the memory is removed and includes memory types such as read only memory (ROM), electronically-erasable programmable memory (EEPROM), and rewritable solid state memory (commonly known as "flash memory"). Non-volatile memory 30a is typically used for long-term storage of a basic input/output system (BIOS) 31, containing the basic instructions, typically loaded during computer startup, for transfer of information between components within computing device, or a unified extensible firmware interface (UEFI), which is a modern replacement for BIOS that supports larger hard drives, faster boot times, more security features, and provides native support for graphics and mouse cursors. Non-volatile memory 30a may also be used to store firmware comprising a complete operating system 35 and applications 36 for operating computer-controlled devices. The firmware approach is often used for purpose-specific computer-controlled devices such as appliances and Internet-of-Things (IoT) devices where processing power and data storage space is limited. Volatile memory 30b is erased when power to the memory is removed and is typically used for short-term storage of data for processing. Volatile memory 30b includes memory types such as random-access memory (RAM), and is normally the primary operating memory into which the operating system 35, applications 36, program modules 37, and application data 38 are loaded for execution by processors 20. Volatile memory 30b is generally faster than non-volatile memory 30a due to its electrical characteristics and is directly accessible to processors 20 for processing of instructions and data storage and retrieval. Volatile memory 30b may comprise one or more smaller cache memories which operate at a higher clock speed and are typically placed on the same IC as the processors to improve performance.

Interfaces 40 may include, but are not limited to, storage media interfaces 41, network interfaces 42, display interfaces 43, and input/output interfaces 44. Storage media interface 41 provides the necessary hardware interface for loading data from non-volatile data storage devices 50 into system memory 30 and storage data from system memory 30 to non-volatile data storage device 50. Network interface 42 provides the necessary hardware interface for computing device 10 to communicate with remote computing devices 80 and cloud-based services 90 via one or more external communication devices 70. Display interface 43 allows for connection of displays 61, monitors, touchscreens, and other visual input/output devices. Display interface 43 may include a graphics card for processing graphics-intensive calculations and for handling demanding display requirements. Typically, a graphics card includes a graphics processing unit (GPU) and video RAM (VRAM) to accelerate display of graphics. One or more input/output (I/O) interfaces 44 provide the necessary support for communications between computing device 10 and any external peripherals and accessories 60. For wireless communications, the necessary radio-frequency hardware and firmware may be connected to I/O interface 44 or may be integrated into I/O interface 44.

Non-volatile data storage devices 50 are typically used for long-term storage of data. Data on non-volatile data storage devices 50 is not erased when power to the non-volatile data storage devices 50 is removed. Non-volatile data storage devices 50 may be implemented using any technology for non-volatile storage of content including, but not limited to, CD-ROM drives, digital versatile discs (DVD), or other optical disc storage; magnetic cassettes, magnetic tape, magnetic disc storage, or other magnetic storage devices; solid state memory technologies such as EEPROM or flash memory; or other memory technology or any other medium which can be used to store data without requiring power to retain the data after it is written. Non-volatile data storage devices 50 may be non-removable from computing device 10 as in the case of internal hard drives, removable from computing device 10 as in the case of external USB hard drives, or a combination thereof, but computing device will typically comprise one or more internal, non-removable hard drives using either magnetic disc or solid-state memory technology. Non-volatile data storage devices 50 may store any type of data including, but not limited to, an operating system 51 for providing low-level and mid-level functionality of computing device 10, applications 52 for providing high-level functionality of computing device 10, program modules 53 such as containerized programs or applications, or other modular content or modular programming, application data 54, and databases 55 such as relational databases, non-relational databases, object oriented databases, BOSQL databases, and graph databases.

Applications (also known as computer software or software applications) are sets of programming instructions designed to perform specific tasks or provide specific functionality on a computer or other computing devices. Applications are typically written in high-level programming languages such as C++, Java, and Python, which are then either interpreted at runtime or compiled into low-level, binary, processor-executable instructions operable on processors 20. Applications may be containerized so that they can be run on any computer hardware running any known operating system. Containerization of computer software is a method of packaging and deploying applications along with their operating system dependencies into self-contained, isolated units known as containers. Containers provide a lightweight and consistent runtime environment that allows applications to run reliably across different computing environments, such as development, testing, and production systems.

The memories and non-volatile data storage devices described herein do not include communication media. Communication media are means of transmission of information such as modulated electromagnetic waves or modulated data signals configured to transmit, not store, information. By way of example, and not limitation, communication media includes wired communications such as sound signals transmitted to a speaker via a speaker wire, and wireless communications such as acoustic waves, radio frequency (RF) transmissions, infrared emissions, and other wireless media.

External communication devices 70 are devices that facilitate communications between computing devices and either remote computing devices 80, or cloud-based services 90, or both. External communication devices 70 include, but are not limited to, data modems 71 which facilitate data transmission between computing device and the Internet 75 via a common carrier such as a telephone company or internet service provider (ISP), routers 72 which facilitate data transmission between computing device and other devices, and switches 73 which provide direct data communications between devices on a network. Here, modem 71 is shown connecting computing device 10 to both remote computing devices 80 and cloud-based services 90 via the Internet 75. While modem 71, router 72, and switch 73 are shown here as being connected to network interface 42, many different network configurations using external communication devices 70 are possible. Using external communication devices 70, networks may be configured as local area networks (LANs) for a single location, building, or campus, wide area networks (WANs) comprising data networks that extend over a larger geographical area, and virtual private networks (VPNs) which can be of any size but connect computers via encrypted communications over public networks such as the Internet 75. As just one exemplary network configuration, network interface 42 may be connected to switch 73 which is connected to router 72 which is connected to modem 71 which provides access for computing device 10 to the Internet 75. Further, any combination of wired 77 or wireless 76 communications between and among computing device 10, external communication devices 70, remote computing devices 80, and cloud-based services 90 may be used. Remote computing devices 80, for example, may communicate with computing device through a variety of communication channels 74 such as through switch 73 via a wired 77 connection, through router 72 via a wireless connection 76, or through modem 71 via the Internet 75. Furthermore, while not shown here, other hardware that is specifically designed for servers may be employed. For example, secure socket layer (SSL) acceleration cards can be used to offload SSL encryption computations, and transmission control protocol/internet protocol (TCP/IP) offload hardware and/or packet classifiers on network interfaces 42 may be installed and used at server devices.

In a networked environment, certain components of computing device 10 may be fully or partially implemented on remote computing devices 80 or cloud-based services 90. Data stored in non-volatile data storage device 50 may be received from, shared with, duplicated on, or offloaded to a non-volatile data storage device on one or more remote computing devices 80 or in a cloud computing service 92. Processing by processors 20 may be received from, shared with, duplicated on, or offloaded to processors of one or more remote computing devices 80 or in a distributed computing service 93. By way of example, data may reside on a cloud computing service 92, but may be usable or otherwise accessible for use by computing device 10. Also, certain processing subtasks may be sent to a microservice 91 for processing with the result being transmitted to computing device 10 for incorporation into a larger processing task. Also, while components and processes of the exemplary computing environment are illustrated herein as discrete units (e.g., OS 51 being stored on non-volatile data storage device 51 and loaded into system memory 35 for use) such processes and components may reside or be processed at various times in different components of computing device 10, remote computing devices 80, and/or cloud-based services 90.

In an implementation, the disclosed systems and methods may utilize, at least in part, containerization techniques to execute one or more processes and/or steps disclosed herein. Containerization is a lightweight and efficient virtualization technique that allows you to package and run applications and their dependencies in isolated environments called containers. One of the most popular containerization platforms is Docker, which is widely used in software development and deployment. Containerization, particularly with open-source technologies like Docker and container orchestration systems like Kubernetes, is a common approach for deploying and managing applications. Containers are created from images, which are lightweight, standalone, and executable packages that include application code, libraries, dependencies, and runtime. Images are often built from a Dockerfile or similar, which contains instructions for assembling the image. Dockerfiles are configuration files that specify how to build a Docker image. Systems like Kubernetes also support containerd or CRI-O. They include commands for installing dependencies, copying files, setting environment variables, and defining runtime configurations. Docker images are stored in repositories, which can be public or private. Docker Hub is an exemplary public registry, and organizations often set up private registries for security and version control using tools such as Hub, JFrog Artifactory and Bintray, Github Packages or Container registries. Containers can communicate with each other and the external world through networking. Docker provides a bridge network by default but can be used with custom networks. Containers within the same network can communicate using container names or IP addresses.

Remote computing devices 80 are any computing devices not part of computing device 10. Remote computing devices 80 include, but are not limited to, personal computers, server computers, thin clients, thick clients, personal digital assistants (PDAs), mobile telephones, watches, tablet computers, laptop computers, multiprocessor systems, microprocessor based systems, set-top boxes, programmable consumer electronics, video game machines, game consoles, portable or handheld gaming units, network terminals, desktop personal computers (PCs), minicomputers, main frame computers, network nodes, virtual reality or augmented reality devices and wearables, and distributed or multi-processing computing environments. While remote computing devices 80 are shown for clarity as being separate from cloud-based services 90, cloud-based services 90 are implemented on collections of networked remote computing devices 80.

Cloud-based services 90 are Internet-accessible services implemented on collections of networked remote computing devices 80. Cloud-based services are typically accessed via application programming interfaces (APIs) which are software interfaces which provide access to computing services within the cloud-based service via API calls, which are pre-defined protocols for requesting a computing service and receiving the results of that computing service. While cloud-based services may comprise any type of computer processing or storage, three common categories of cloud-based services 90 are microservices 91, cloud computing services 92, and distributed computing services 93.

Microservices 91 are collections of small, loosely coupled, and independently deployable computing services. Each microservice represents a specific computing functionality and runs as a separate process or container. Microservices promote the decomposition of complex applications into smaller, manageable services that can be developed, deployed, and scaled independently. These services communicate with each other through well-defined application programming interfaces (APIs), typically using lightweight protocols like HTTP, gRPC, or message queues such as Kafka. Microservices 91 can be combined to perform more complex processing tasks.

Cloud computing services 92 are delivery of computing resources and services over the Internet 75 from a remote location. Cloud computing services 92 provide additional computer hardware and storage on as needed or subscription basis. Cloud computing services 92 can provide large amounts of scalable data storage, access to sophisticated software and powerful server-based processing, or entire computing infrastructures and platforms. For example, cloud computing services can provide virtualized computing resources such as virtual machines, storage, and networks, platforms for developing, running, and managing applications without the complexity of infrastructure management, and complete software applications over the Internet on a subscription basis.

Distributed computing services 93 provide large-scale processing using multiple interconnected computers or nodes to solve computational problems or perform tasks collectively. In distributed computing, the processing and storage capabilities of multiple machines are leveraged to work together as a unified system. Distributed computing services are designed to address problems that cannot be efficiently solved by a single computer or that require large-scale computational power. These services enable parallel processing, fault tolerance, and scalability by distributing tasks across multiple nodes.

Although described above as a physical device, computing device 10 can be a virtual computing device, in which case the functionality of the physical components herein described, such as processors 20, system memory 30, network interfaces 40, and other like components can be provided by computer-executable instructions. Such computer-executable instructions can execute on a single physical computing device, or can be distributed across multiple physical computing devices, including being distributed across multiple physical computing devices in a dynamic manner such that the specific, physical computing devices hosting such computer-executable instructions can dynamically change over time depending upon need and availability. In the situation where computing device 10 is a virtualized device, the underlying physical computing devices hosting such a virtualized computing device can, themselves, comprise physical components analogous to those described above, and operating in a like manner. Furthermore, virtual computing devices can be utilized in multiple layers with one virtual computing device executing within the construct of another virtual computing device. Thus, computing device 10 may be either a physical computing device or a virtualized computing device within which computer-executable instructions can be executed in a manner consistent with their execution by a physical computing device. Similarly, terms referring to physical components of the computing device, as utilized herein, mean either those physical components or virtualizations thereof performing the same or equivalent functions.

The skilled person will be aware of a range of possible modifications of the various aspects described above. Accordingly, the present invention is defined by the claims and their equivalents.

What is claimed is:

1. A computer-implemented method executed on a platform for discretely filtering and evaluating two or more human genomes for compatibility and risk scoring, the computer-implemented method comprising:
   upon receiving a filtering request from a device associated with a user, filter across multiple elements, activities, and platforms to connect with a prospective mate;
   providing selective opt-in screening accommodating user-specific preferences, facilitating engagement with multiple applications using common omics, environmental, and lifestyle data;
   implementing cloud-based or edge-based processing, making the invention robust to periodic or sporadic connectivity and data processing needs and types;
   adapting analysis and visibility conditions based on user preferences, regulations, laws, or application/community rules, with configurable alerts for positive or negative matches;
   incorporating a secure and privacy preserving homomorphic or regular encrypted omics data and personal lifestyle, activity, and environmental exposure into a personal health database cloud or edge-based processing system;
   utilizing a plurality of encrypted genomic and omics data within the cloud or edge-based processing system to perform screening on human omics datasets using a homomorphically encrypted algorithm, employing suitable approximations for isolated, semi-parallel, or parallel Genome Wide Association Study (GWAS);
   leveraging the complex space of homomorphic encryption methods enabling direct computations on the encrypted data, increasing the number of single nucleotide polymorphisms (SNPs), mutations, or other modifications in Deoxyribonucleic Acid (DNA), Ribonucleic Acid (RNA), mitochondrial DNA (mtDNA) of people or microbiome elements that can be packed within a ciphertext;
   calculating the genetic compatibility scores for the individuals determining susceptibility of hereditary conditions in future offspring, assessing potential genetic risks and associated life impacts, costs, and longevity considerations in progeny or prospective partner; and
   uploading the calculated results, displaying the genetic compatibility, through results or suggestions, to the end user while limiting disclosed data to user authorized information.

2. The computer-implemented method of claim 1, wherein at least a portion of genetic screening allows for user opt in prior to sharing a subset of data.

3. The computer-implemented method of claim 1, wherein at least a portion of the dataset sensitive data is removed, obfuscated, anonymized, or otherwise limited.

4. The computer-implemented method of claim 1, wherein at least a portion of screening process allows users to declare preferences including genetic factors prior to sharing data.

5. The computer-implemented method of claim 1, wherein at least a portion of screening process allows users to declare preferences including emotional factors, health concerns, medical treatment, or reproductive assistance preferences prior to sharing data.

6. The computer-implemented method of claim 1, wherein at least a portion of screening process allows users to declare medical or lifestyle preferences including religious factors prior to sharing data.

7. The computer-implemented method of claim 1, wherein at least a portion of screening process allows users to declare preferences including behavioral or environmental factors prior to sharing data.

8. The computer-implemented method of claim 1, wherein at least a portion of the ability for multiple applications, such as mobile sensors, third party applications, biometrics, and similar applications to engage with common data.

9. The computer-implemented method of claim 1, wherein at least a portion of the data includes single-nucleotide polymorphism (SNP), DNA, RNA, mtDNA, and microbiome data.

10. The computer-implemented method of claim 1, wherein at least a portion of the display is comprised of wearable devices, mobile devices, videoconferencing or holographic devices, computers, Internet-of-Things devices, gaming platforms or devices, and augmented reality or virtual reality systems.

11. A computing system for discretely filtering and evaluating two or more human genomes for compatibility and risk scoring, the computing system comprising:
   upon receiving a filtering request from a device associated with a user, filter across multiple elements, activities, and platforms to connect with a prospective mate;
   providing selective opt-in screening accommodating user-specific preferences, facilitating engagement with multiple applications using common omics, environmental, and lifestyle data;
   implementing cloud-based or edge-based processing, making the invention robust to periodic or sporadic connectivity and data processing needs and types;
   adapting analysis and visibility conditions based on user preferences, regulations, laws, or application/community rules, with configurable alerts for positive or negative matches;
   incorporating a secure and privacy preserving homomorphic or regular encrypted omics data and personal lifestyle, activity, and environmental exposure into a personal health database cloud or edge-based processing system;
   utilizing a plurality of encrypted genomic and omics data within the cloud or edge-based processing system to perform screening on human omics datasets using a homomorphically encrypted algorithm, employing suitable approximations for isolated, semi-parallel, or parallel Genome Wide Association Study (GWAS);
   leveraging the complex space of homomorphic encryption methods enabling direct computations on the encrypted data, increasing the number of single nucleotide polymorphisms (SNPs), mutations, or other modifications in Deoxyribonucleic Acid (DNA), Ribonucleic Acid (RNA), mitochondrial DNA (mtDNA) of people or microbiome elements that can be packed within a ciphertext;
   calculating the genetic compatibility scores for the individuals determining susceptibility of hereditary conditions in future offspring, assessing potential genetic risks and associated life impacts, costs, and longevity considerations in progeny or prospective partner; and
   uploading the calculated results, displaying the genetic compatibility, through results or suggestions, to the end user while limiting disclosed data to user authorized information.

12. The computing system of claim 11, wherein at least a portion of genetic screening allows for user opt in prior to sharing a subset of data.

13. The computing system of claim 11, wherein at least a portion of the dataset sensitive data is removed, obfuscated, anonymized, or otherwise limited.

14. The computing system of claim 11, wherein at least a portion of screening process allows users to declare preferences including genetic factors prior to sharing data.

15. The computing system of claim 11, wherein at least a portion of screening process allows users to declare preferences including emotional factors, health concerns, medical treatment, or reproductive assistance preferences prior to sharing data.

16. The computing system of claim 11, wherein at least a portion of screening process allows users to declare medical or lifestyle preferences including religious factors prior to sharing data.

17. The computing system of claim 11, wherein at least a portion of screening process allows users to declare preferences including behavioral or environmental factors prior to sharing data.

18. The computing system of claim 11, wherein at least a portion of the ability for multiple applications, such as mobile sensors, third party applications, biometrics, and similar applications to engage with common data.

19. The computing system of claim 11, wherein at least a portion of the data includes single-nucleotide polymorphism (SNP), DNA, RNA, mtDNA, and microbiome data.

20. The computing system of claim 11, wherein at least a portion of the display is comprised of wearable devices, mobile devices, videoconferencing or holographic devices, computers, Internet-of-Things devices, gaming platforms or devices, and augmented reality or virtual reality systems.

21. Non-transitory, computer-readable storage media having computer instructions embodied thereon that, when executed by one or more processors of a computing system employing platform for discretely filtering and evaluating two or more human genomes for compatibility and risk scoring, cause the computing system to:
   upon receiving a filtering request from a device associated with a user, filter across multiple elements, activities, and platforms to connect with a prospective mate;
   providing selective opt-in screening accommodating user-specific preferences, facilitating engagement with multiple applications using common omics, environmental, and lifestyle data;
   implementing cloud-based or edge-based processing, making the invention robust to periodic or sporadic connectivity and data processing needs and types;
   adapting analysis and visibility conditions based on user preferences, regulations, laws, or application/community rules, with configurable alerts for positive or negative matches;
   incorporating a secure and privacy preserving homomorphic or regular encrypted omics data and personal lifestyle, activity, and environmental exposure into a personal health database cloud or edge-based processing system;
   utilizing a plurality of encrypted genomic and omics data within the cloud or edge-based processing system to perform screening on human omics datasets using a homomorphically encrypted algorithm, employing suitable approximations for isolated, semi-parallel, or parallel Genome Wide Association Study (GWAS);
   leveraging the complex space of homomorphic encryption methods enabling direct computations on the encrypted data, increasing the number of single nucleotide polymorphisms (SNPs), mutations, or other modifications in Deoxyribonucleic Acid (DNA), Ribonucleic Acid (RNA), mitochondrial DNA (mtDNA) of people or microbiome elements that can be packed within a ciphertext;
   calculating the genetic compatibility scores for the individuals determining susceptibility of hereditary conditions in future offspring, assessing potential genetic risks and associated life impacts, costs, and longevity considerations in progeny or prospective partner; and
   uploading the calculated results, displaying the genetic compatibility, through results or suggestions, to the end user while limiting disclosed data to user authorized information.

22. The system of claim 21, wherein at least a portion of genetic screening allows for user opt in prior to sharing a subset of data.

23. The system of claim 21, wherein at least a portion of the dataset sensitive data is removed, obfuscated, anonymized, or otherwise limited.

24. The system of claim 21, wherein at least a portion of the data includes single-nucleotide polymorphism (SNP), DNA, RNA, mtDNA, and microbiome data.

* * * * *